(12) United States Patent
Dong et al.

(10) Patent No.: US 9,574,203 B1
(45) Date of Patent: Feb. 21, 2017

(54) TRANSGENIC GUAYULE FOR ENHANCED ISOPRENOID PRODUCTION

(71) Applicant: The United States of America, as represented by the Secretary of Agriculture, Washington, DC (US)

(72) Inventors: Niu Dong, San Pablo, CA (US); Colleen M McMahan, Sausalito, CA (US); Maureen C Whalen, El Cerrito, CA (US); Katrina Cornish, Wooster, OH (US); Terry A Coffelt, Chandler, AZ (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 133 days.

(21) Appl. No.: 14/075,761

(22) Filed: Nov. 8, 2013

Related U.S. Application Data

(60) Provisional application No. 61/724,244, filed on Nov. 8, 2012.

(51) Int. Cl.
  *C12N 15/82* (2006.01)
  *A01H 5/00* (2006.01)
(52) U.S. Cl.
  CPC ......... *C12N 15/8243* (2013.01); *A01H 5/00* (2013.01)
(58) Field of Classification Search
  None
  See application file for complete search history.

(56) References Cited

U.S. PATENT DOCUMENTS

| | | | | |
|---|---|---|---|---|
| 2003/0150008 A1* | 8/2003 | Karunanandaa | ..... | C12N 9/0006 800/278 |
| 2006/0217512 A1* | 9/2006 | Mau | ..................... | C12N 9/1085 528/1 |

OTHER PUBLICATIONS (Friesen and Rodwell, 2004, Genome Biology 5: 248.1-7.*
Benedict et al., 2011, Industrial Crops and Products 33: 89-93.*
Salvucci et al., 2010, Physiologia Plantarum 140: 368-379.*
UniProt polypeptide sequence of Q5B6L3_EMENI, EAA60025 (EMBL:EAA60025.1) of *Aspergillus nidulans*, published Apr. 26, 2005.*
NCBI/GenBank sequence of *Aspergillus nidulans* HMGR1 gene, accession No. AF479817 (ver. AF479817.1), published Apr. 2, 2003.*
Chappell, Joseph et al., "Is the Reaction Catalyzed by 3-Hydroxy-3-Methylglutaryl Coenzyme A Reductase a Rate-Limiting Step for Isoprenoid Biosynthesis in Plants?", (1995) Plant Phisiology 109:1337-1343.

Dong, N. et al., "Overexpression of 3-hydroxy-3-methylglutaryl coenzyme A reductase in *Parthenium argentatum* (guayule)", (2013) Industrial Crops and Products 46:15-24.
Dong, N. et al., "Overexpression of HMGR in guayule: Laboratory and field studies", McMahan, C.M., and Berti, M.T. Eds. (2012), 24th Annual AAIC Meeting. Industrial Crops: Developing Sustainable Solutions: Program and Abstracts. Nov. 12-15, 2012, Sonoma, CA. p. 31.
Ponciano, Grisel et al., "Transcriptome and gene expression analysis in cold-acclimated guayule (*Parthenium argentatum*) rubber-producing tissue", (2012) Phytochemistry 79:57-66.
Veatch, M.E. et al., "Growth, rubber, and resin evaluation of two-year-old transgenic guayule", (2005) Industrial Crops and Products 22:65-74.
Cornish, K., "Similarities and Differences in Rubber Biochemistry among Plant Species", (2001), Phytochemistry 57:1123-1134.
Cornish, K et al., "Methods in Enzymology", (2012), Natural Rubber Biosynthesis in Plants: Rubber Transferase, 515:63-82.
Enfissi, E. M. A. et al., "Metabolic Engineering of the Mevalonate and Nonmevalonate Isopentenyl Diphosphate-Forming Pathways for the Production of Health-Promoting Isoprenoids in Tomato", (2005), Plant Biotechnology Journal, 3:17-27.
Harker, N. et al, "Enhancement of Seed Phytosterol Levels by Expression of an N-terminal Truncated *Hevea brasiliensis* (rubber tree) 3-hydroxy-3-methylglutaryl-CoA Reductase ", (2003) Plant Biotechnology Journal 1:113-121.
Holmberg, N. et al., "Co-Expression of N-terminal Truncated 3-Hydrocy-3-Methyglutarl CoA Reductase and C24-sterol Methyltransferase Type 1 in Transgenic Tobacco Enhances Carbon Flux Towards End-Product Sterols", (2003) The Plant Journal 36: 12-20.
Ji,W. et al., "Seasonal Variations in Rubber Biosynthesis, 3-Hydroxy-3-Methylglutaryl-Coenzyme A Reductase, and Rubber Transferase Activities in *Parthenium argentatum* in the Chihuahuan Desert", (1993), Plant Physiol.103:535-542.
Sando, T. et al., "Cloning and Characterization of the 2-C Methyl-D-erythritol 4-Phosphate (MEP) Pathway Genes of a Natural-Rubber Producing Plant, *Hevea brasiliensis*", (2008), Biosci. Biotechnol. Biochem, 72(11):2903-2917.
Schaller, H. et al., "Expression of the *Hevea brasiliensis* (H.B.K.) Müll. Arg. 3-Hydroxy-3-Methylglutaryl-Coenzyme A Reductase 1 in Tobacco Results in Sterol Overproduction", (1995), The Plant Physiol., 109:761-770.
Suzuki, M. et al., "Loss of Function of 3-Hydroxy-3-Methylglutaryl Coenzyme A Reductase 1 (HMG1) in Arabidopsis Leads to Dwarfing, Early Senescenece and Male Steriltiy, and Reduced Sterol Levels", (2004), The Plant Journal, 37:750-761.
Wang, G-Y., et al., "Amplification of HMG-CoA Reductase Production Enhances Carotenoid Accumulation in *Neurospora crassa*", (2002), Metabiolic Engineering, 4:193-201.
Wentzinger, L. F. et al., "Inhibition of Squalene Synthase and Squalene Epoxidase in Tobacco Cells Triggers an Up-Regulation of 3-Hydroxy-3-Methylglutaryl Coenzyme A Reductase", (2002) Plant Physiol, 130:334-346.
Whalen, M. et al., "Development of Crops to Produce Industrially Useful Natural Rubber", T.J. Bach and M. Rohmer (eds.), Isoprenoid Synthesis in Plants and Microorganisms: New Concepts and Experimental Approaches, (2013), Springer Science+Business Media New York.

* cited by examiner

Primary Examiner — Amjad Abraham
Assistant Examiner — Bratislav Stankovic
(74) Attorney, Agent, or Firm — David L. Marks; John D. Fado

(57) ABSTRACT

The present invention relates to transgenic guayule plants that produce increased amounts of rubber uses thereof.

27 Claims, 20 Drawing Sheets

```
      cttttctctg gaccctacgc caggattcct tcttttgac ctggaccacc ggtctggtga
   61 tcttcccttc ccatatctca agcaatagtg ctgtggctcc cagcgcggca tctcattggc
  121 tcccagttct gttccttcct aatagcgtaa gtctttctag gcggcagaat tcgccggctt
  181 acttaaaact atttctttc caagggtcac gggtggctca agctctttcg ctctggttga
  241 gtgtgcttca ggggctcggt ggctgtgacg actcgactga cccgagcgtc ggtagaaata
  301 gatcaagaag accagttctg ttggcaatcg attttgggaa cagcgactgc gattcttgtg
  361 attttttttt ttttgaatta ttggtcttac accgacatat cgctcacgac attgttgcgt
  421 cttcgggtat gtctgcccca gcattggctc ttgcatcgcc tttcgtagtt gtcgccgctt
  481 ttccctagtc gcctcgctcc gctccttgct agtggctggc ccattgcagg aaatcactcg
  541 ctaacgccaa aaaatgtcag gtttctcgaa gtcccttatc cgcagaacat ataccctcct
  601 gtttcctcgc ccatgtcatt gaacttcgaa aaccggtctt gatctattgc caaccgctgt
  661 aaagacgacc tgcgcgattg aacatatcgg ataggggtctc tcgctcggtg tgacccatcc
  721 gcctcagcgc atctgttcag gcactccgag tcgtaccttt gtaccacgct cacaccgcct
  781 cccctcgta agctatcatg gcttccgtgt tgattcggag gaagtttggg acagaaggag
  841 gcagtgatgc tgaaccttcc tggctgaagc gccaggttac cggctgcctg cagtcgatct
  901 ctcgtcgcgc ctgcatccat cctatccaca caatcgtcgt gatcgccctt ctggcgagta
  961 caacatatgt cggcctgctt gagggcagct tattcgattc gttcagaaat tcgaacaatg
 1021 ttgctggcca tgtggatgtt gactcgctcc tcctcggtaa caggagtctc cggttgggcg
 1081 aaggcacatc atggaagtgg caagttgagg actcactgaa tcaggacgac caaaaggtgg
 1141 ggaatcctga actaagagg gaggtttgaa ctcatatcta atctcaacgg cttttaggtc
 1201 gaccaacatc ttgctttgac gactttgata tttccggact ctattcgaa atccgcgtcg
 1261 accgctcctg ctgccgacgc tatcccagtt cccgccaatg cctccgctca gcttctccct
 1321 catacgccta atctcttctc gccattctct cacgactcct ctcttgtctt caccttcct
 1381 ttcgaccagg ttcctcaatt tctgagagcg gtccaggagc ttcctgaccc gacgcttgaa
 1441 gatgacgaag gtgaacaaaa acgatggatt atgcgtgcta cccgcggccc ggtcagtgga
 1501 ccgaatggaa ccatcagctc ctggctgtcg gatgcgtgga gttcctttgt ggatttgatc
 1561 aaggtatccc ttgcgtgggc ttctctacat gtccgattgc taactactga tagcatgccg
 1621 aaaccatcga tatcatcatc atgactctag gttatcttgc gatgtatctt agctttgcct
 1681 ctctgttctt ctctatgaaa cagttggggt cgaagttttg gcttgctacc actgtccttt
 1741 tctcgggcat gttcgctttc ctgtttgggt ctcctcgtta ccacgaagtt ggcgttccg
 1801 atcaacattc tccttctatc agagggcctc ccgttccttg ttacgacaat gggtttgaa
 1861 aagccgatta ttctcaccag ggcagttctt agtgcgtcga tcgacaagaa acgccaaggt
 1921 tcagcgactt cgactcccag ttctattcag gattcgattc agaccgcaat ccgagaacag
 1981 ggtttcgaga ttattcgaga ctactgtatc gaaatctcca ttcttattgc aggagctgct
 2041 tctggagttc agggcggtct gagacaattt tgcttcctcg ctgcttggat ccttttcttc
 2101 gactgccttt tgctcttcac cttctacacg actatcctct gcattaagct tgagatcaca
 2161 cgtatcaggc gccatgtgac ccttcgcaag gctctggagg aagatggtat tacgcagagt
 2221 gttgccgaaa aggtcgcctc gagcaatgat tggtttggtg ccggatcgga aatagcgac
 2281 gcagatgacg ctagtgtttt tggacgaaa atcaaatcga acaatgttcg ccgcttcaag
 2341 ttcttgatgg tcggggtttt tgtgctggtc aacgtggtga atatgactgc aatcccttc
 2401 cggaattcga gcttgtcacc tctctgcaat gtcttctcgc ctacaccgat agatccctc
 2461 aaggttgctg agaacggtct ggatgccatc tacgtttccg ctaaaagcca gaagttggag
 2521 acattagtga cagttgtccc gcccatcaag tacaaacttg agtatccgtc ggtgcattat
 2581 gctaagctgg gagagagcca gtctattgaa attaatata ccgaccagct tctggatgct
 2641 gtgggcggac acgtcctcaa cggcgtttg aagagcattg aggacccagt tatcagcaag
 2701 tggatcattg cagtgttgac tttgagcata gtcctcaacg gctatctatt taacgccgca
 2761 agatggagca tcaaggaacc acaagccgcc ccgctccta aggaaccggc caagccaaag
 2821 gtctatccca aaatcgactt gaacgctggc cctaagagga gcatggagga atgtgaggca
 2881 atgctaaaag cgaaaaaggc agcctacctt agcgatgagg agctgattga actttcactc
 2941 tctggcaaac ttcctggata tgctctggag aagtcattgg aaaatgagga acttatgagc
 3001 cgtgttgatg ccttcacccg ggcagtcaaa atccgcaggg ctgtagtatc gaggaccccc
 3061 gcaacttctg cagtcaccag ctctttggaa acttctaagc tgccctataa ggattacaat
```

FIG. 1A

```
3121 tatgcgcttg tccatggtgc ttgctgtgag aacgttattg gcaccctgcc tctgcctctt
3181 ggagttgccg gtcccttgt tattgatggt caaagctatt tcattcccat ggcaacaact
3241 gaaggtgttt tggtagccag tgccagtcga ggcgccaagg ctattaacgc tggtggtggt
3301 gcagtgactg tcttaactgg cgatggcatg actcgcggtc cctgtgtcgg gtttcctaca
3361 cttgcacgcg cagctgcagc taaggtctgg ctcgactccg aggagggtaa gagcgtcatg
3421 acagcagcat tcaactctac cagccgcttt gctcgactgc agcacctgaa gactgcccCt
3481 gccggtacct acttgtatat ccggttcaag acgactactg gcgatgccat gggtatgaac
3541 atgatttcga aaggcgttga gaaagcactc catgtcatgg ctacagagtg tggattcgac
3601 gacatggcca ccatctctgt gtctggcaac ttttgtaccg acaagaaagc agctgctctc
3661 aactggattg acggccgcgg caaatcagtt gtggctgagg ctattatccc cggtgatgtt
3721 gtgcgcaatg tgctaaagag tgatgttgat gcattggtgg aattgaacac tagcaagaat
3781 ctgattggca gtgcaatggc aggtagcttg ggcggattca acgctcacgc atcaaacatt
3841 gttactgcaa tctttctcgc aactggtcaa gaccccgcgc aaaatgtgga gagcagcagc
3901 tgcattacca cgatgaagaa gtaagtagta tactttgatg tctttctctc ctggtcggcg
3961 ctaaccacgt tttagtacaa atggcaatct tcagatcgct gtgtctatgc cttcaattga
4021 ggttggcact atcggtggtg gtactatcct cgaagcgcag ggtgctatgc ttgacttact
4081 aggcgtccgt ggctctcacc ccaccaaccc cggcgacaac gcgcgtcagc tggctcgtat
4141 tgtggcagcc gcagtgcttg ctggcgaact gagtctatgc tctgcgcttg cggctggaca
4201 tcttgtcaga gcgcacatgg cccacaaccg cagtgccgct cccactcggt cagcgacccc
4261 ggtctcagcg gctgttggtg ctacgcgggg actgtccatg acgtcttcaa gatagatatc
4321 atgagtgcat gcctttctcc ttcctacctt ttacgataaa tacgatgcga ctaggctttc
4381 ttacgacggc cattctggaa ctaactgtcc ctcattcggt tcgctcaccc ggacttcttc
4441 cacttccggc acacattttc tgagcttttt tacatgtggg ttttacggcg accgtgaatc
4501 atatggtcag cctcattttt ttttgggagt ctattgaata tactggagtc tgggcatata
4561 catagaactg cgctacggat tgacctgaac aagagatata ctaaaaagca aaggagacga
4621 gcagtcgctc tttgcacaag ggcagctgtt cgtcggacta catctgaaga tgattgtttg
```

FIG. 1B

```
  1 MEECEAMLKA KKAAYLSDEE LIELSLSGKL PGYALEKSLE
    NEELMSRVDA FTRAVKIRRA VVSRTPATSA VTSSLETSKL
 81 PYKDYNYALV HGACCENVIG TLPLPLGVAG PLVIDGQSYF
    IPMATTEGVL VASASRGAKA INAGGGAVTV LTGDGMTRGP
161 CVGFPTLARA AAAKVWLDSE EGKSVMTAAF NSTSRFARLQ
    HLKTALAGTY LYIRFKTTTG DAMGMNMISK GVEKALHVMA
241 TECGFDDMAT ISVSGNFCTD KKAAALNWID GRGKSVVAEA
    IIPGDVVRNV LKSDVDALVE LNTSKNLIGS AMAGSLGGFN
321 AHASNIVTAI FLATGQDPAQ NVESSSCITT MKNTNGNLQI
    AVSMPSIEVG TIGGGTILEA QGAMLDLLGV RGSHPTNPGD
401 NARQLARIVA AAVLAGELSL CSALAAGHLV RAHMAHNRSA
    APTRSATPVS AAVGATRGLS MTSSR
```

FIG. 2 pND9 T-DNA sequence (empty vector control)
T-DNA Sequences of pND9_GUSint (LB-T$_{ocs}$-NPTII-P$_{4095}$-P$_{2x35S}$~GUSInt-T$_{nos}$-RB)

```
TGATCACAGGCAGCAACGCTCTGTCATCGTTACAATCAACATGCTACCCTCCGCGAGATCATCCGTGTTTCAAACCC
GGCAGCTTAGTTGCCGTTCTTCCGAATAGCATCGGTAACATGAGCAAAGTCTGCCGCCTTACAACGGCTCTCCCGCT
GACGCCGTCCCGGACTGATGGGCTGCCTGTATCGAGTGGTGATTTTGTGCCGAGCTGCCGGTCGGGGAGCTGTTGGC
TGGCTGGTGGCAGGATATATTGTGGTGTAAACAAATTGACGCTTAGACAACTTAATAACACATTGCGGACGTTTTTA
ATGTACTGAATTAACGCCGAATTGCTTAATTAAGTCCTGCTGAGCCTCGACATGTTGTCGCAAAATTCGCCCTGGAC
CCGCCCAACGATTTGTCGTCACTGTCAAGGTTTGACCTGCACTTCATTTGGGGCCCACATACACCAAAAAAATGCTG
CATAATTCTCGGGGCAGCAAGTCGGTTACCCGGCCGCCGTGCTGGACCGGGTTGAATGGTGCCCGTAACTTTCGGTA
GAGCGGACGGCCAATACTCAACTTCAAGGAATCTCACCCATGCGCGCCGGCGGGGAACCGGAGTTCCCTTCAGTGAA
CGTTATTAGTTCGCCGCTCGGTGTGTCGTAGATACTAGCCCCTGGGGCCTTTTGAAATTTGAATAAGATTTATGTAA
TCAGTCTTTTAGGTTTGACCGGTTCTGCCGCTTTTTTTAAAATTGGATTTGTAATAATAAAACGCAATTGTTTGTTA
TTGTGGCGCTCTATCATAGATGTCGCTATAAACCTATTCAGCACAATATATTGTTTTCATTTTAATATTGTACATAT
AAGTAGTAGGGTACAATCAGTAAATTGAACGGAGAATATATTCATAAAAATACGATAGTAACGGGTGATATATTCA
TTAGAATGAACCGAAACCGGCGGTAAGGATCTGAGCTACACATGCTCAGGTTTTTTACAACGTGCACAACAGAATTG
AAAGCAAATATCATGCGATCATAGGCGTCTCGCATATCTCATTAAAGAGCTCGAGCTTGTCGATCGACTCTAGCTAG
AGGATCGATCCGAACCCCAGAGTCCCGCTCAGAAGAACTCGTCAAGAAGGCGATAGAAGGCGATGCGCTGCGAATCG
GGAGCGGCGATACCGTAAAGCACGAGGAAGCGGTCAGCCCATTCGCCGCCAAGCTCTTCAGCAATATCACGGGTAGC
CAACGCTATGTCCTGATAGCGGTCCGCCACACCCAGCCGGCCACAGTCGATGAATCCAGAAAAGCGGCCATTTTCCA
CCATGATATTCGGCAAGCAGGCATCGCCATGTGTCACGACGAGATCCTCGCCGTCGGGCATGCGCGCCTTGAGCCTG
GCGAACAGTTCGGCTGGCGCGAGCCCCTGATGCTCTTCGTCCAGATCATCCTGATCGACAAGACCGGCTTCCATCCG
AGTACGTGCTCGCTCGATGCGATGTTTCGCTTGGTGGTCGAATGGGCAGGTAGCCGGATCAAGCGTATGCAGCCGCC
GCATTGCATCAGCCATGATGGATACTTTCTCGGCAGGAGCAAGGTGAGATGACAGGAGATCCTGCCCCGGCACTTCG
CCCAATAGCAGCCAGTCCCTTCCCGCTTCAGTGACAACGTCGAGCACAGCTGCGCAAGGAACGCCCGTCGTGGCCAG
CCACGATAGCCGCGCTGCCTCGTCCTGGAGTTCATTCAGGGCACCGGACAGGTCGGTCTTGACAAAAAGAACCGGGC
GCCCCTGCGCTGACAGCCGGAACACGGCGGCATCAGAGCAGCCGATTGTCTGTTGTGCCCAGTCATAGCCGAATAGC
CTCTCCACCCAAGCGGCCGGAGAACCTGCGTGCAATCCATCTTGTTCAATCCCCATACCACCTCTTAAGCGGAGCAC
CAAATGGAGGGTAGACTCCTTCTGGATGTTGTAGTCGGCAAGAGTACGACCATCCTCAAGCTGCTTTCCGGCGAAAA
TCAAACGCTGCTGGTCTGGGGAATCCCTTCCTTGTCCTGGATCTTGGCTTTGACATTGTCGATGGTGTCGGAAGAC
TCAACCTCTAGGGTGATCGTCTTCCCCGTTAGGGTCTTCACGAAGATCTGCATCTGCAAAGTCATAAAAACAACAWT
CAGAACAACGGAAAAAAACTCAAATTATAGGGCTTTTCACACTCCCTGATTAACTGATTCGAGAATTAAAACCAAAC
AATCTAAAACACGGGGAAAAAACTCAAATTTTAGGGCTTTTTCATCAAAACAACCGGAAAAACCTCAAATTTTAGGGC
TTTAGAATCAAACCGACGAAAAATCACAAATTCTAGGGCTTTTTCATCAAATCAACCGGAAAAAAAAATCAAATTC
AAGACCTTTTTCATCAAACCACCATAAAAAAACTCAAATTCTAGGGCATTATCATCAAATCACCCGGAAAACCCCAC
ATTTTGGGCCTTTAGAATCAAACCGACGAAAAAACTCTAATTTTAAACCTTTGGCATCAAATCGACGGAAAAAAACT
CAAATTAGGGGCTTTTTCATCAAAACAACGGAAAAAAAACTCAAATTTTAGGGCTTTAACAGCACCTGCTTAGCTAA
TTCGAGAATCTAAACAGACAAAAACCAAAAAATAGAGAAGATTTCTAACCTTGAAAGAGAAATTTAAAGGCAATTGA
GAGAAATTATAATAGAAGTCAGATAGAAGATGAAAAAATGAGGTGCAGAAAGGTTCCTTTTATAGATGGCATGGCCG
ACTCTAGACGAAACCGCCTCATAGGGTTAGCCAATTATATGATGACACGTGTAATAATGAGGTGTAGTGTAGCAAAA
CAACACGCAAAAGCTACCGTTTCTTTTTATTTATGTGGTGGGGAAAATTAGGAGAATGAGGTTGACGCTTACACGCT
CCTTTAGAAAAAACTAGAAAAATGTAGGTCATAGTAAAAAAAATATACTAAAAATAACTTAATTTTATTTTAGGTATT
```

FIG. 10B

GGCCAAAATCTGGGGAAAAAATTTGGTCTGAATTTAATTAGAATGATATTTTATTTATGTTATTTTATTTTTAAAA
TATTTTTATTCTTTTAACTTTAATACATTTTAACTAAAAAATAAAGAATATATCAATTTATTTTAAAATAAAAAAAT
ATTATAATTTTCTTAATTTTCTATCTAATTTTTTTGATCATTTAGCATTTTCTTTTTTATTAATTAATATATGCTCT
AATATAGCGCTTTTTAAGTATATTGTGAACATAACCTTAAATATAAGAGTTTAAATATTAGCAAATTAGGGTATAAT
ACTCGTTGATAATCGCACTTTAATCTTTTTTCTTATATTATGTATTGCTCCTTTTTTTTACATTATTTTTTTATTGT
TATTGACCTCATATTGATAAGTATTTGTTATCTAAATTTGATTGAAAATATTTTATTTAAATTGAGTATATATTAGA
AACACTTTTCTTTTTTATATAAGAGGTAAGTATCAAGCTTGCATGCCTGCAGGTCCGATTGAGACTTTTCAACAAA
GGGTAATATCCGGAAACCTCCTCGGATTCCATTGCCCAGCTATCTGTCACTTTATTGTGAAGATAGTGGAAAAGGAA
GGTGGCTCCTACAAATGCCATCATTGCGATAAAGGAAAGGCCATCGTTGAAGATGCCTCTGCCGACAGTGGTCCCAA
AGATGGACCCCACCCACGAGGAGCATCGTGGAAAAAGAAGACGTTCCAACCACGTCTTCAAAGCAAGTGGATTGAT
GTGATGGTCCGATTGAGACTTTTCAACAAAGGGTAATATCCGGAAACCTCCTCGGATTCCATTGCCCAGCTATCTGT
CACTTTATTGTGAAGATAGTGGAAAAGGAAGGTGGCTCCTACAAATGCCATCATTGCGATAAAGGAAAGGCCATCGT
TGAAGATGCCTCTGCCGACAGTGGTCCCAAAGATGGACCCCACCCACGAGGAGCATCGTGGAAAAAGAAGACGTTC
CAACCACGTCTTCAAAGCAAGTGGATTGATGTGATATCTCCACTGACGTAAGGGATGACGCACAATCCCACTATCCT
TCGCAAGACCCTTCCTCTATATAAGGAAGTTCATTTCATTTGGAGAGGAGATCTTTTTATTTTTAATTTTCTTTCAA
ATACTTCCACCATGGTATATATAGGAAGTTCATTTCATTTGGAATGGAcacgtgttgtcatttctCAACACAACATA
TACAAAACAAACGAATCTCAAGCAATCAAGCATTCTACCAATAACTATTTACAATTACATCTAGTTAAACAatgtca
ggcccaattacgaagaaaagggcttgtaaaaccctaataaagtggcactggcagagcttacactctcattccatcaa
caaagaaaccctaaaagccgcagcgccactgatttctctcctccaggcgaagatgcagatcttcgtgaagaccctaa
cggggaagacgatcaccctagaggttgagtcttccgacaccatcgacaatgtcaaagccaagatccaggacaaggaa
gggattcccccagaccagcagcgtttgattttcgccggaaagcagcttgaggatggtcgtactcttgccgactacaa
catccagaaggagtctaccctccatttggtgctccgcttaagaggtggtATGTTACGTCCTGTAGAAACCCCAACCC
GTGAAATCAAAAAACTCGACGGCCTGTGGGCATTCAGTCTGGATCGCGAAAACTGTGGAATTGATCAGCGTTGGTGG
GAAAGCGCGTTACAAGAAAGCCGGGCAATTGCTGTGCCAGGCAGTTTTAACGATCAGTTCGCCGATGCAGATATTCG
TAATTATGCGGGCAACGTCTGGTATCAGCGCGAAGTCTTTATACCGAAAGGTTGGGCAGGCCAGCGTATCGTGCTGC
GTTTCGATGCGGTCACTCATTACGGCAAAGTGTGGGTCAATAATCAGGAAGTGATGGAGCATCAGGGCGGCTATACG
CCATTTGAAGCCGATGTCACGCCGTATGTTATTGCCGGGAAAAGTGTACGTAAGTTTCTGCTTCTACCTTTGATATA
TATATAATAATTATCATTAATTAGTAGTAATATAATATTTCAAATATTTTTTCAAAATAAAAGAATGTAGTATATA
GCAATTGCTTTTCTGTAGTTTATAAGTGTGTATATTTTAATTTATAACTTTTCTAATATATGACCAAAATTTGTTGA
TGTGCAGGTATCACCGTTTGTGTGAACAACGAACTGAACTGGCAGACTATCCCGCCGGGAATGGTGATTACCGACGA
AAACGGCAAGAAAAAGCAGTCTTACTTCCATGATTTCTTTAACTATGCCGGAATCCATCGCAGCGTAATGCTCTACA
CCACGCCGAACACCTGGGTGGACGATATCACCGTGGTGACGCATGTCGCGCAAGACTGTAACCACGCGTCTGTTGAC
TGGCAGGTGGTGGCCAATGGTGATGTCAGCGTTGAACTGCGTGATGCGGATCAACAGGTGGTTGCAACTGGACAAGG
CACTAGCGGGACTTTGCAAGTGGTGAATCCGCACCTCTGGCAACCGGGTGAAGGTTATCTCTATGAACTGTGCGTCA
CAGCCAAAAGCCAGACAGAGTGTGATATCTACCCGCTTCGCGTCGGCATCCGGTCAGTGGCAGTGAAGGGCCAACAG
TTCCTGATTAACCACAAACCGTTCTACTTTACTGGCTTTGGTCGTCATGAAGATGCGGACTTACGTGGCAAAGGATT
CGATAACGTGCTGATGGTGCACGACCACGCATTAATGGACTGGATTGGGGCCAACTCCTACCGTACCTCGCATTACC
CTTACGCTGAAGAGATGCTCGACTGGGCAGATGAACATGGCATCGTGGTGATTGATGAAACTGCTGCTGTCGGCTTT
AACCTCTCTTTAGGCATTGGTTTCGAAGCGGGCAACAAGCCGAAAGAACTGTACAGCGAAGAGGCAGTCAACGGGGA
AACTCAGCAAGCGCACTTACAAGCGATTAAAGAGCTGATAGCGCGCGACAAAAACCACCCAAGCGTGGTGATGTGGA
GTATTGCCAACGAACCGGATACCCGTCCGCAAGTGCACGGGAATATTTCGCCACTGGCGGAAGCAACGCGTAAACTC
GACCCGACGCGTCCGATCACCTGCGTCAATGTAATGTTCTGCGACGCTCACACCGATACCATCAGCGATCTCTTTGA
TGTGCTGTGCCTGAACCGTTATTACGGATGGTATGTCCAAAGCGGCGATTTGGAAACGGCAGAGAAGGTACTGGAAA
AAGAACTTCTGGCCTGGCAGGAGAAACTGCATCAGCCGATTATCATCACCGAATACGGCGTGGATACGTTAGCCGGG
CTGCACTCAATGTACACCGACATGTGGAGTGAAGAGTATCAGTGTGCATGGCTGGATATGTATCACCGCGTCTTTGA

FIG. 10C

```
TCGCGTCAGCGCCGTCGTCGGTGAACAGGTATGGAATTTCGCCGATTTTGCGACCTCGCAAGGCATATTGCGCGTTG
GCGGTAACAAGAAAGGGATCTTCACTCGCGACCGCAAACCGAAGTCGGCGGCTTTTCTGCTGCAAAAACGCTGGACT
GGCATGAACTTCGGTGAAAAACCGCaGCAGGGAGGCAAACAAtctagccaccaccaccaccacgtg tga attac
aggtgaccGAGCTCGAATTTCCCCGATCGTTCAAACATTTGGCAATAAAGTTTCTTATAAGATTGAATCCTGTTGCC
GGTCTTGCGATGATTATCATATAATTTCTGTTGAATTACGTTAAGCATGTAATAATTAACATGTAATGCATGACGTT
ATTTATGAGATGGGTTTTTATGATTAGAGTCCCGCAATTATACATTTAATACGCGATAGAAAACAAAATATAGCGCG
CAAACTAGGATAAATTATCGCGCGCGGTGTCATCTATGTTACTAGATCGGGGAATTCGTAATCATGTCATAGCTGTT
TCCTGTGTGAAATTGTTATCCGCTCACAATTCCACACAACATACGAGCCGGAAGCATAAAGTGTAAAGCCTGGGGTG
CCTAATGAGTGAGCTAACTCACATTAATTGCGTTGCGCTCACTGCCCGCTTTCCAGTCGGGAAACCTGTCGTGCCAG
CTGCATTAATGAATCGGCCAACGCGCGGGGAAAAGGCGGTTTGCGTATTGGAGCTTGAGCTTGGATCAGATTGTCGT
TTCCCGCCTTCAGTTTAAACTATCAGTGTTTGACAGGATATATTGGCGGGTAAACCTAAGAGAAAAGAGCGTTTATT
AGAATAATCGGATATTTAAAAGGGCGTGAAAAGGTTTATCCGTTCGTCCATTTGTATGTGCATGCCAACCACAGGGT
TCCCCTCGGGATCAAAGTACT
```

FIG. 10D pND9_427P-HMGRtAN2A-FPPs_T-DNA construct (designed for overexpression of both HMGR and FPPs by a single constitutive promoter)

pND9_427P-HMGRtAN2A-FPPS_T-DNA (9472 bp)

pND9_427P-HMGRtAN2A-FPPs_T-DNA sequence (designed for overexpression of both HMGR and FPPs by a single constitutive promoter)

pND9_427P_HMGR(tAN)_2A_FPPS_NosT_T-DNA

TGATCACAGGCAGCAACGCTCTGTCATCGTTACAATCAACATGCTACCCTCCGCGAGATCATCCGTGTTTCAAACCCG
GCAGCTTAGTTGCCGTTCTTCCGAATAGCATCGGTAACATGAGCAAAGTCTGCCGCCTTACAACGGCTCTCCCGCTGA
CGCCGTCCCGGACTGATGGGCTGCCTGTATCGAGTGGTGATTTTGTGCCGAGCTGCCGGTCGGGGAGCTGTTGGCTGG
CTGGTGGCAGGATATATTGTGGTGTAAACAAATTGACGCTTAGACAACTTAATAACACATTGCGGACGTTTTTAATGT
ACTGAATTAACGCCGAATTGCTTAATTAAGTCCTGCTGAGCCTCGACATGTTGTCGCAAAATTCGCCCTGGACCCGCC
CAACGATTTGTCGTCACTGTCAAGGTTTGACCTGCACTTCATTTGGGGCCCACATACACCAAAAAAATGCTGCATAAT
TCTCGGGGCAGCAAGTCGGTTACCCGGCCGCCGTGCTGGACCGGGTTGAATGGTGCCCGTAACTTTCGGTAGAGCGGA
CGGCCAATACTCAACTTCAAGGAATCTCACCCATGCGCGCCGGCGGGGAACCGGAGTTCCCTTCAGTGAACGTTATTA
GTTCGCCGCTCGGTGTGTCGTAGATACTAGCCCCTGGGGCCTTTTGAAATTTGAATAAGATTTATGTAATCAGTCTTT
TAGGTTTGACCGGTTCTGCCGCTTTTTTTAAAATTGGATTTGTAATAATAAAACGCAATTGTTTGTTATTGTGGCGCT
CTATCATAGATGTCGCTATAAACCTATTCAGCACAATATATTGTTTTCATTTTAATATTGTACATATAAGTAGTAGGG
TACAATCAGTAAATTGAACGGAGAATATTATTCATAAAAATACGATAGTAACGGGTGATATATTCATTAGAATGAACC
GAAACCGGCGGTAAGGATCTGAGCTACACATGCTCAGGTTTTTTACAACGTGCACAACAGAATTGAAAGCAAATATCA
TGCGATCATAGGCGTCTCGCATATCTCATTAAAGAGCTCGAGcttgtcgatcgactctagctagaggatcgatccgaa
ccccagagtcccgcTCAGAAGAACTCGTCAAGAAGGCGATAGAAGGCGATGCGCTGCGAATCGGGAGCGGCGATACCG
TAAAGCACGAGGAAGCGGTCAGCCCATTCGCCGCCAAGCTCTTCAGCAATATCACGGGTAGCCAACGCTATGTCCTGA
TAGCGGTCCGCCACACCCAGCCGGCCACAGTCGATGAATCCAGAAAAGCGGCCATTTTCCACCATGATATTCGGCAAG
CAGGCATCGCCATGTGTCACGACGAGATCCTCGCCGTCGGGCATGCGCGCCTTGAGCCTGGCGAACAGTTCGGCTGGC
GCGAGCCCCTGATGCTCTTCGTCCAGATCATCCTGATCGACAAGACCGGCTTCCATCCGAGTACGTGCTCGCTCGATG
CGATGTTTCGCTTGGTGGTCGAATGGGCAGGTAGCCGGATCAAGCGTATGCAGCCGCCGCATTGCATCAGCCATGATG
GATACTTTCTCGGCAGGAGCAAGGTGAGATGACAGGAGATCCTGCCCCGGCACTTCGCCCAATAGCAGCCAGTCCCTT
CCCGCTTCAGTGACAACGTCGAGCACAGCTGCGCAAGGAACGCCCGTCGTGGCCAGCCACGATAGCCGCGCTGCCTCG
TCCTGGAGTTCATTCAGGGCACCGGACAGGTCGGTCTTGACAAAAGAACCGGGCGCCCCTGCGCTGACAGCCGGAAC
ACGGCGGCATCAGAGCAGCCGATTGTCTGTTGTGCCCAGTCATAGCCGAATAGCCTCTCCACCCAAGCGGCCGGAGAA
CCTGCGTGCAATCCATCTTGTTCAATCCCCATaccacctcttaagcggagcaccaaatggagggtagactccttctgg
atgttgtagtcggcaagagtacgaccatcctcaagctgctttccggcgaaaatcaaacgctgctggtctggggaatc
ccttccttgtcctggatcttggctttgacattgtcgatggtgtcggaagactcaacctctagggtgatcgtcttcccc
gttagggtcttcacgaagatctgcatCTGCAAAGTCATAAAAACAACAWTCAGAACAACGGAAAAAAACTCAAATTAT
AGGGCTTTTCACACTCCCTGATTAACTGATTCGAGAATTAAAACCAAACAATCTAAAACACGGGGAAAAAACTCAAAT
TTTAGGGCTTTTTCATCAAAACAACCGGAAAACCTCAAATTTTAGGGCTTTAGAATCAAACCGACGAAAAATCACAAA
TTCTAGGGCTTTTTCATCAAATCAACCGGAAAAAAAAATCAAATTCAAGACCTTTTTCATCAAACCACCATAAAAAA
ACTCAAATTCTAGGGCATTATCATCAAATCACCCGGAAAACCCCACATTTTGGGCCTTTAGAATCAAACCGACGAAAA
AACTCTAATTTTAAACCTTTGGCATCAAATCGACGGAAAAAAACTCAAATTAGGGGCTTTTTCATCAAAACAACGGAA
AAAAAACTCAAATTTTAGGGCTTTAACAGCACCTGCTTAGCTAATTCGAGAATCTAAACAGACAAAAACCAAAAAATA
GAGAAGATTTCTAACCTTGAAAGAGAAATTTAAAGGCAATTGAGAGAAATTATAATAGAAGTCAGATAGAAGATGAAA
AAATGAGGTGCAGAAAGGTTCCTTTTATAGATGGCATGGCCGACTCTAGACGAAACCGCCTCATAGGGTTAGCCAATT
ATATGATGACACGTGTAATAATGAGGTGTAGTGTAGCAAAACAACACGCAAAAGCTACCGTTTCTTTTTATTTATGTG
GTGGGGAAAATTAGGAGAATGAGGTTGACGCTTACACGCTCCTTTAGAAAAAACTAGAAAAATGTAGGTCATAGTAAA

FIG. 11B

```
AAAATATACTAAAAATAACTTAATTTTATTTTAGGTATTGGCCAAAATCTGGGGAAAAAATTTGGTCTGAATTTAATT
AGAATGATATTTTATTTATGTTATTTTATTTTTAAAATATTTTATTCTTTTAACTTTAATACATTTTAACTAAAAA
ATAAAGAATATATCAATTTATTTAAAATAAAAAAATATTATAATTTTCTTAATTTTCTATCTAATTTTTTTGATCAT
TTAGCATTTTCTTTTTTATTAATTAATATATGCTCTAATATAGCGCTTTTTAAGTATATTGTGAACATAACCTTAAAT
ATAAGAGTTAAATATTAGCAAATTAGGGTATAATACTCGTTGATAATCGCACTTTAATCTTTTTTCTTATATTATGT
ATTGCTCCTTTTTTTTACATTATTTTTTTATTGTTATTGACCTCATATTGATAAGTATTTGTTATCTAAATTTGATTG
AAAATATTTTATTTAAATTGAGTATATATTAGAAACACTTTTTCTTTTTTATATAAGAGGTAAGTATCAAGCTTGCAT
GCCTGCAGGCGGCTTGCTtGGTCTTACTTCATCGTCGAGAAAAGAAAGAAGACTTCTATCTACAAGTTTAACTCAAAC
GTAGTTCTTTTATTTTTTGGGTGTGAAGTAGTGTCAAACCAAAATACCCTTTCTAAACAACTATTGTTTGTGAATAT
AGGTTGTGTTGTTTCTCATTCGGAAGACCAAGTCCCACACCCTAACTTCACTGATGAGAACAACCTCCGCACTCTGGG
CTGTTTAAATCCCCGGTTGAAATCATCCAACCAAACTCTCTTTATTTCGAGATTGAAAAGGTCGATCAATTATGATCA
AAGATAATGCCTAGTGGCGACGAGCCCACTAGGAAGACCTTTGATTACAAAGGTTACCGTGGTCTAGGTTTATAATGG
ATTCAATTAATCAAAGTGCCTCCAACTCAAGCTCATTTTCCTATCAGGAGAAAACAATGCATAAAAAAGGGATGGCCG
TCAAAAAGCCGACCCTTCAATCCAAAAGCGTTCAAATTCCGCCTACATCAGCTCGACCTGTTTGTTCGCTCTAATTA
GGATCATCAGAATATCTTGACAGATTTTTTTGAAAAGCTTAACTTGCAAGCGGAGAATGCCGAGTCTCTACCCACTTT
TTGAGCTTGCAAAGTAGCAATATGAAATTTCTTGGGCACTTACCCGTCGTGCTTGAGATCTAAACTGCTTACAACAAC
CTTGACCTGGTCCAATGAAAAGAGAAAGACTTAAAGAGCTCCCTCTATAGGTGACTCCTCCAATAAGACTCTTAGGGT
GCATGTCAAAACCCGCTAAGTTAGGAGTATACATAAAATTTTGGCCGATATAAGGATTAATATAACCAAATAATATAA
CGAAAATAAATTTAAACAATAAAAAATAATAAAGAGATGTATCCATTCTTTTTCACTCAAATTGTATTTTTAGAAATT
ATAGTCAAATTTACTATCAAAATTTAAAAAATTAATTTTTAAAATTATACATGCCATGAATTTGAAATTTGAAAAAGG
GAAAAAGAGGAGAAGCATCTAGTAAGGCTCTAATTAATTGCGTAACCGTGTCTTCTAAAATATCCGAAGAAATTGCGT
AAGCGCTGAGCCATAGGCCCATACGTTCCCTCTCTGTGACGGCAAAGCGGTTACTATAAATACAGATCTTCCCTTTTT
CAACCAAATCCCCAAATCATCATCCTTCTCTAGCGCAACTTCTCTCGGAAAAAAGCATCTCCTCCTCCTCTCGTTTTC
TCGATAATCTCCTTGTACACTGTTTCTTCTTCTCAAGGTAATGGTCTTTTCTTCTCTCGATTCAATCGTTTGTTGAAG
TGATTTAGATTTATGCAGGTTTTTGTATTATAAATGTATGAACAGAATTATATGAACGGAATTTACCTTTGTTTCTTG
TTTATCGATCAGATCTGCACGGAATTAGTCGATTTGAGAACTTTTTGAAATCGATGATGTATGTTTTTTCTGTTGATG
ATGCTATAGCGTTTAATTTCGTTTGATTTGCTCTTGTTTTGGTTTCCATATGGTCGAATTGTTGAAGTTTCGTAGTTT
GATTAGTTTTGTATCCTATCTAGGGTTTTTTGTGATCACAATTAATCAATTTGAAATGGTGATGCTTGCTTTTTCTGT
TGATGATGTTATAGCATTGAATTTCGTTGATTTGCTTGATTTTTTGGTCACTGTTTAATAGAAATTGTTCAAGTTTCC
AGGTTTGATTAATTGTGTCCTGTGTAGGGATATTTATGATCAAAATTAATCAATTTGAAGAAAACACTATGTTTAATG
GATAATATATGCTTTTTATTTTTCTTGTTGATGATGTTATAGTCTTGTATATTCTCGTGTTGTTCCATTTTTCTGTT
TTCTATTTGCTTGAAATTGTTCAAGTTTCTAGGTTTGATTATTTGTGTGCTATCTAGGGATTTTTGTGATCAAAATTA
CAAATCTAGGTTAAATGGATGATGCATGCTTTTGCTGCTGATGATTTATAGCCTTGAATTTTGTCGATTTGCTTCATT
TTTGGTCTCTATTTAATGAAATTGTTGAAGTTTCTAGGTTTGATTAATTGTGTCTTGTCTAGGGTTTTGCGAACAAA
TTGAACTAGATTTAAATAAAATTTAGGAGTCCTCAATTTTTTTGTTTGTTAACTCTTATTGATCTGTTTTTTTAATGTA
TTTATTCTTGTGTGGGCACATTGTTATTCTCTTCTGATTATGCTACGATCGTGAACTTGATTTGATTTACAATACATC
CAATTGTGGGTTTGCATCCCTCTTAAAATGATAAGTATAGTTTGTTCTAGGTAGAATTGGATGCTTCTAGGGGCCTAC
TGATTTGTTTGTAAAAATGGTTGTTCATTGGATTGAATTTTATTAAAGAAAAAATCTGAAATTCTAATAATTCTTGT
AAATTAGGTTGATGTCAGATCTATTTATTTTCTTCTTTGTTTGGTTGACTGGTCTTCTGGTGGCTCTCTGATTAGTGT
AATTATAGTTGACTTTGGATATGTTGCTTTTGCTCTTTGTATGGTTTCTAATCAATTGGGATTCTTTTCTTATTCTCT
CCTAATTTGCCTCTGGTTTGATATATTCAATTTTAACTTCAATTGTTTCGTGGGATGACTTGTCCCAAATTAAACAAG
TTCTGAGATTTGTGTGCAAGCTATGCTATGGGTGTTCATATTATGTGGTAGTTCGCTGCTGTAAGAGGGAGATTGCAG
AACCTTTATTATATCGTCTTTTCTTTTGGACTTCCAAAGCTTGCTAGTTTGTCATCTCTGCCTGATTGAATAGAATT
TTTGACAGTTGTGTGCTTGAATATATTTCAGACCGGTCGCCACCATGGAGGAATGTGAGGCAATGCTAAAAGCGAAAA
```

FIG. 11C

```
AGGCAGCCTACCTTAGCGATGAGGAGCTGATTGAACTTTCACTCTCTGGCAAACTTCCTGGATATGCTCTGGAGAAGT
CATTGGAAAATGAGGAACTTATGAGCCGTGTTGATGCCTTCACCCGGGCAGTCAAAATCCGCAGGGCTGTAGTATCGA
GGACCCCCGCAACTTCTGCAATCACCAGCTCTTTGGAAACTTCTAAGCTGCCCTATAAGGATTACAATTATGCGCTTG
TCCATGGTGCTTGCTGTGAGAACGTTATTGGCACCCTGCCTCTGCCTCTTGGAGTTGCCGGTCCCCTTGTTATTGATG
GTCAAAGCTATTTCATTCCCATGGCAACAACTGAAGGTGTtTTGGTAGCCAGTGCCAgTCGAGGCGCCAAGGCTATTA
ACGCTGGTGGTGGTGCAGTGACTGTCTTAAcTGGCGATGGCATGACTCGCGGTCCCTGTGTCGGGTTTCCTACACTTG
CACGCGCAGCTGCAGCTAAGGTCTGGCTCGACTCCGAGGAGGGTAAGAGCGTCaTGACAGCAGCATTCAACTCTACCA
GCCGGTTTGCTCGACTGCAGCACCTGAAGACTGCCCTTGCCGGTACCTACTTGTATATCCGGTTCAAGACGACTACTG
GCGATGCCATGGGTATGAACATGATTTCGAAAGGCGTTGAGAAAGCACTCCATGTCATGGCTACAGAGTGTAGATTCG
ACGACATGGCCACCATCTCTGTGTCTGGCAACTTTTGTACCGACAAGAAAGCAGCTGCTCTCAACTGGATTGACGGCC
GCGGCAAATCAGTTGTGGCTGAGGCTATTATCCCGGTGATGTTGTGCGCAATGTGCTAAAGAGTGGTGTTGATGCAT
TGGTGGAATTGAACACTAGCAAGAATCTGATTGGCAGTGCAATGGCAGGTAGCTTGGGCGGATTCAACGCTCACGCAT
CAAACATTGTTACTGCAATCTTTCTCGAACTGGTCAAGACCCCGCGCAAAATGTGGAGAGCAGCAGCTGCATTACCA
CGATGAAGAATACAAATGGCAATCTTCAGATCGCTGTGTCTATGCCTTCAATTGAGGTTGGCACTATCGGTGGTGGTA
CTATCCTCGAAGCGCAGGGTGCTATGCTTGACTTACTAGGCGTCCGTGGCTCTCACCCCACCAACCCCGGCGATAACG
CGCGTCAGCTGGCTCGTATTGTGGCAGCCGCAGTGCTTGCTGGCGAACTGAGTCTATGCTCTGCGCTTGCGGCTGGAC
ATCTtGTCAGAGCGCACATGGCCCACAACCGCAGTGCCGCTCCCACTCGGTCAGCGAcCCCGGTCTCAGCGGCTGTTG
GTGCTACGCGGGACTGTCCATGACGTCTTCAAGATCTaggggagcctgccagctgttgaattttgaccttcttaagc
tggcgggagacgtcgagtccaaccctgggcccATGGCGCAGCTTTCAGTTGAACAGTTTCTCAACGAGCAAAAACAGG
CGGTGGAAACAGCGCTCTCCCGTTATATAGAGCGCTTAGAAGGGCCGGCGAAGCTGAAAAAGGCGATGGCGTACTCAT
TGGAGGCCGGCGGCAAACGAATCCGTCCGTTGCTGCTTCTGTCCACCGTTCGGGCGCTCGGCAAAGACCCGGCGGTCG
GATTGCCCGTCGCCTGCGCGATTGAAATGATCCATACGTACTCTTTGATCCATGATGATTTGCCGAGCATGGACAACG
ATGATTTGCGGCGCGGCAAGCCGACGAACCATAAAGTGTTCGGCGAGGCGATGGCCATCTTGGCGGGGACGGGTTGT
TGACGTACGCGTTTCAATTGATCACCGAAATCGACGATGAGCGCATCCCTCCTTCCGTCCGGCTTCGGCTCATCGAAC
GGCTGGCGAAAGCGGCCGGTCCGGAAGGGATGGTCGCCGGTCAGGCAGCCGATATGGAAGGAGAGGGGAAAACGCTGA
CGCTTTCGGAGCTCGAATACATTCATCGGCATAAAACCGGGAAAATGCTGCAATACAGCGTGCACGCCGGCGCCTTGA
TCGGCGGCGCTGATGCCCGGCAAACGCGGGAGCTTGACGAATTCGCCGCCCATCTAGGCCTTGCCTTTCAAATTCGCG
ATGATATTCTCGATATTGAAGGGGCAGAAGAAAAAATCGGCAAGCCGGTCGGCAGCGACCAAAGCAACAACAAAGCGA
CGTATCCAGCGTTGCTGTCGCTTGCCGGCGCGAAGGAAAAGTTGGCGTTCCATATCGAGGCGGCGCAGCGCCATTTAC
GGAACGCCGACGTTGACGGCGCCGCGCTCGCCTATATTTGCGAACTGGTCGCCGCCCGCGACCATTCTAGCCACCACC
ACCACCACCACGTGTGAattacaggtgaccgagctcGAATTTCCCCGATCGTTCAAACATTTGGCAATAAAGTTTCTT
ATAAGATTGAATCCTGTTGCCGGTCTTGCGATGATTATCATATAATTTCTGTTGAATTACGTTAAGCATGTAATAATT
AACATGTAATGCATGACGTTATTTATGAGATGGGTTTTTATGATTAGAGTCCCGCAATTATACATTTAATACGCGATA
GAAAACAAAATATAGCGCGCAAACTAGGATAAATTATCGCGCGCGGTGTCATCTATGTTACTAGATCGGGGAATTCgt
aatcatgtcatagctgtttcctgtgtgaaattgttatccgctcacaattccacacaacatacgagccggaagcataaa
gtgtaaagcctggggtgcctaatgagtgagctaactcacattaattgcgttgcgctcactgcccgctttccagtcggg
aaacctgtcgtgccagctgcattaatgaatcggccaacgcgcggggaaaaggcggtttgcgtattggAGCTTGAGCTT
GGATCAGATTGTCGTTTCCCGCCTTCAGTTTAAACTATCAGTGTT[TGACAGGATATATTGGCGGGTAAAC]CTAAGAGA
AAAGAGCGTTTATTAGAATAATCGGATATTTAAAAGGGCGTGAAAAGGTTTATCCGTTCGTCCATTTGTATGTGCATG
CCAACCACAGGGTTCCCCTCGGGATCAAAGTACT
```

9472 bp

FIG. 11D pND9_CBF2P-HMGRtAN2A-FPPs_T-DNA construct (designed for overexpression of both HMGR and FPPs by a single cold-inducible promoter)

pND9_CBF2P-HMGRtAN2A-FPPS T-DNA (7702 bp)

pND9_CBF2P_HMGR_2A_FPPS_NosT_T-DNA

TGATCACAGGCAGCAACGCTCTGTCATCGTTACAATCAACATGCTACCCTCCGCGAGATCATCCGTGTTTCAAACCC
GGCAGCTTAGTTGCCGTTCTTCCGAATAGCATCGGTAACATGAGCAAAGTCTGCCGCCTTACAACGGCTCTCCCGCT
GACGCCGTCCCGGACTGATGGGCTGCCTGTATCGAGTGGTGATTTTGTGCCGAGCTGCCGGTCGGGGAGCTGTTGGC
TGGCTGGTGGCAGGATATATTGTGGTGTAAACAAATTGACGCTTAGACAACTTAATAACACATTGCGGACGTTTTTA
ATGTACTGAATTAACGCCGAATTGCTTAATTAAGTCCTGCTGAGCCTCGACATGTTGTCGCAAAATTCGCCCTGGAC
CCGCCCAACGATTTGTCGTCACTGTCAAGGTTTGACCTGCACTTCATTTGGGGCCCACATACACCAAAAAAATGCTG
CATAATTCTCGGGGCAGCAAGTCGGTTACCCGGCCGCCGTGCTGGACCGGGTTGAATGGTGCCCGTAACTTTCGGTA
GAGCGGACGGCCAATACTCAACTTCAAGGAATCTCACCCATGCGCGCCGGCGGGGAACCGGAGTTCCCTTCAGTGAA
CGTTATTAGTTCGCCGCTCGGTGTGTCGTAGATACTAGCCCCTGGGGCCTTTTGAAATTTGAATAAGATTTATGTAA
TCAGTCTTTTAGGTTTGACCGGTTCTGCCGCTTTTTTAAAATTGGATTTGTAATAATAAACGCAATTGTTTGTTA
TTGTGGCGCTCTATCATAGATGTCGCTATAAACCTATTCAGCACAATATATTGTTTTCATTTTAATATTGTACATAT
AAGTAGTAGGGTACAATCAGTAAATTGAACGGAGAATATTATTCATAAAAATACGATAGTAACGGGTGATATATTCA
TTAGAATGAACCGAAACCGGCGGTAAGGATCTGAGCTACACATGCTCAGGTTTTTTACAACGTGCACAACAGAATTG
AAAGCAAATATCATGCGATCATAGGCGTCTCGCATATCTCATTAAAGAGCTCGAGCTTGTCGATCGACTCTAGCTAG
AGGATCGATCCGAACCCCAGAGTCCCGCTCAAAGAACTCGTCAAGAAGGCGATAGAAGGCGATGCGCTGCGAATCG
GGAGCGGCGATACCGTAAAGCACGAGGAAGCGGTCAGCCCATTCGCCGCCAAGCTCTTCAGCAATATCACGGGTAGC
CAACGCTATGTCCTGATAGCGGTCCGCCACACCCAGCCGGCCACAGTCGATGAATCCAGAAAAGCGGCCATTTTCCA
CCATGATATTCGGCAAGCAGGCATCGCCATGTGTCACGACGAGATCCTCGCCGTCGGGCATGCGCGCCTTGAGCCTG
GCGAACAGTTCGGCTGGCGCGAGCCCCTGATGCTCTTCGTCCAGATCATCCTGATCGACAAGACCGGCTTCCATCCG
AGTACGTGCTCGCTCGATGCGATGTTTCGCTTGGTGGTCGAATGGGCAGGTAGCCGGATCAAGCGTATGCAGCCGCC
GCATTGCATCAGCCATGATGGATACTTTCTCGGCAGGAGCAAGGTGAGATGACAGGAGATCCTGCCCCGGCACTTCG
CCCAATAGCAGCCAGTCCCTTCCCGCTTCAGTGACAACGTCGAGCACAGCTGCGCAAGGAACGCCCGTCGTGGCCAG
CCACGATAGCCGCGCTGCCTCGTCCTGGAGTTCATTCAGGGCACCGGACAGGTCGGTCTTGACAAAAAGAACCGGGC
GCCCCTGCGCTGACAGCCGGAACACGGCGGCATCAGAGCAGCCGATTGTCTGTTGTGCCCAGTCATAGCCGAATAGC
CTCTCCACCCAAGCGGCCGGAGAACCTGCGTGCAATCCATCTTGTTCAATCCCCATaccacctcttaagcggagcac
caaatggagggtagactccttctggatgttgtagtcggcaagagtacgaccatcctcaagctgctttccggcgaaaa
tcaaacgctgctggtctgggggaatcccttccttgtcctggatcttggctttgacattgtcgatggtgtcggaagac
tcaacctctagggtgatcgtcttccccgttagggtcttcacgaagatctgcatCTGCAAAGTCATAAAAACAACAWT
CAGAACAACGGAAAAAAACTCAAATTATAGGGCTTTTCACACTCCCTGATTAACTGATTCGAGAATTAAAACCAAAC
AATCTAAAACACGGGGAAAAAACTCAAATTTTAGGGCTTTTTCATCAAAACAACCGGAAAACCTCAAATTTTAGGGC
TTTAGAATCAAACCGACGAAAAATCACAAATTCTAGGGCTTTTTCATCAAATCAACCGGAAAAAAAAATCAAATTC
AAGACCTTTTCATCAAACCACCATAAAAAACTCAAATTCTAGGGCATTATCATCAAATCACCCGGAAAACCCCAC
ATTTTGGGCCTTTAGAATCAAACCGACGAAAAAACTCTAATTTTAAACCTTTGGCATCAAATCGACGGAAAAAAACT
CAAATTAGGGGCTTTTTCATCAAAACAACGGAAAAAAAACTCAAATTTTAGGGCTTTAACAGCACCTGCTTAGCTAA
TTCGAGAATCTAAACAGACAAAAACCAAAAAATAGAGAAGATTTCTAACCTTGAAAGAGAAATTTAAAGGCAATTGA
GAGAAATTATAATAGAAGTCAGATAGAAGATGAAAAAATGAGGTGCAGAAAGGTTCCTTTTATAGATGGCATGGCCG
ACTCTAGACGAAACCGCCTCATAGGGTTAGCCAATTATATGATGACACGTGTAATAATGAGGTGTAGTGTAGCAAAA
CAACACGCAAAAGCTACCGTTTCTTTTTATTTATGTGGTGGGGAAAATTAGGAGAATGAGGTTGACGCTTACACGCT
CCTTTAGAAAAAACTAGAAAAATGTAGGTCATAGTAAAAAATATACTAAAAATAACTTAATTTTATTTAGGTATT
GGCCAAAATCTGGGGAAAAAATTTGGTCTGAATTTAATTAGAATGATATTTTATTTATGTTATTTTATTTTTAAAA
TATTTTATTCTTTTAACTTTAATACATTTAACTAAAAAATAAAGAATATATCAATTTATTTTAAAATAAAAAAAT
ATTATAATTTCTTAATTTTCTATCTAATTTTTTGATCATTTAGCATTTCTTTTTATTAATTAATATATGCTCT
AATATAGCGCTTTTTAAGTATATTGTGAACATAACCTTAAATATAAGAGTTTAAATATTAGCAAATTAGGGTATAAT
ACTCGTTGATAATCGCACTTTAATCTTTTTCTTATATTATGTATTGCTCCTTTTTTTTACATTATTTTTTATTGT
TATTGACCTCATATTGATAAGTATTTGTTATCTAAATTTGATTGAAAATATTTTATTTAAATTGAGTATATATTAGA

FIG. 12B

AACACTTTTTCTTTTTTATATAAGAGGTAAGTATCAAGCTTGCATGCCTGCAGGAGATGCTGGAAATTGTGATCAAC
TACATGCAAAATGTCTTTTCGCCTAACCACTTACCATATTTGATATTTTCCTTTTGCCAAATTACACAAACCCTATC
TTGTCTCTCACATATATATCCAATTAATACACCCCTGCCACTTGTTAATTCTCGACCATGTATGTATACTTATGTAA
AGAATATCCAAAAGCTTTCTTTTTGTTCCTTCGATTTTAAGCAACTTGTGTTCTCATTTCTCAATATCTTAAAGAAA
TCCTGAGTAAAAAAGTTTATAGCCTCCGTGAATCTTAGGAAATTACTCTAGCATATTCAAATTTTTTGAAACAATAT
ATAAATTTTTCTGAATAATTAAATTTACATATCTATGCTACGAAACTTGATTAATTAAATCAAATATATATATATAT
ATATAATAATAATAATAATATAACATTTTTTTTAGGACACAAATATCTAATCTCACTATACTCTAGAAGTATTT
GCAATGCACGATATGTGAATGGAGAAAAGACAGAAAGAGCATTTGAAAATATCTCGTTTCACGGATCATTATGTCTA
ATTATTTTACCATAGAAAAGCGACAATTATAAACAATTTGTTATTCGTGGAAAAATAATATTTAATAATGGTTGTCG
TACCCTATAAACTACAGCCACACATTCATACAATAAGAAGTTAAAAAAATTCATACCCTAAAGGCATCAACCAGTGA
AGGGTCAGAAACTTCCCAAGATGGGTCAAAGGACACATGTCAGATTCTCAGTGATTGACAGCCTTGATAATTACAAA
ACCGTGGGATCGCTTAGCTGTTTCTTATCCACGTGGCATTCACAGAGACAGAAACTCCGCGTTCGACCCCACAAATA
TCCAAATATCTTCCGGCCAATATAAACAGCAAGCTCTCACTCCAACATTTCTATAACTTCAAACACTTACCTGAATT
AGAAAAGAAAGATAGATAGAGAAATAAATATTTTATCATACCATACAAAAAAAGACAGAGATCTTCTACTTACTCTA
CTCTCATAAACCTTATCCAGTTTCTTGAAACAGAGTACTCTTCTGATCAATGGAGGAATGTGAGGCAATGCTAAAAG
CGAAAAAGGCAGCCTACCTTAGCGATGAGGAGCTGATTGAACTTTCACTCTCTGGCAAACTTCCTGGATATGCTCTG
GAGAAGTCATTGGAAAATGAGGAACTTATGAGCCGTGTTGATGCCTTCACCCGGGCAGTCAAAATCCGCAGGGCTGT
AGTATCGAGGACCCCCGCAACTTCTGCAATCACCAGCTCTTTGGAAACTTCTAAGCTGCCCTATAAGGATTACAATT
ATGCGCTTGTCCATGGTGCTTGCTGTGAGAACGTTATTGGCACCCTGCCTCTGCCTCTTGGAGTTGCCGGTCCCCTT
GTTATTGATGGTCAAAGCTATTTCATTCCCATGGCAACAACTGAAGGTGTtTTGGTAGCCAGTGCCAgTCGAGGCGC
CAAGGCTATTAACGCTGGTGGTGGTGCAGTGACTGTCTTAAcTGGCGATGGCATGACTCGCGGTCCCTGTGTCGGGT
TTCCTACACTTGCACGCGCAGCTGCAGCTAAGGTCTGGCTCGACTCCGAGGAGGGTAAGAGCGTCaTGACAGCAGCA
TTCAACTCTACCAGCCGGTTTGCTCGACTGCAGCACCTGAAGACTGCCCTTGCCGGTACCTACTTGTATATCCGGTT
CAAGACGACTACTGGCGATGCCATGGGTATGAACATGATTTCGAAAGGCGTTGAGAAAGCACTCCATGTCATGGCTA
CAGAGTGTAGATTCGACGACATGGCCACCATCTCTGTGTCTGGCAACTTTTGTACCGACAAGAAAGCAGCTGCTCTC
AACTGGATTGACGGCCGCGGCAAATCAGTTGTGGCTGAGGCTATTATCCCCGGTGATGTTGTGCGCAATGTGCTAAA
GAGTGGTGTTGATGCATTGGTGGAATTGAACACTAGCAAGAATCTGATTGGCAGTGCAATGGCAGGTAGCTTGGGCG
GATTCAACGCTCACGCATCAAACATTGTTACTGCAATCTTTCTCGCAACTGGTCAAGACCCCGCGCAAAATGTGGAG
AGCAGCAGCTGCATTACCACGATGAAGAATACAAATGGCAATCTTCAGATCGCTGTGTCTATGCCTTCAATTGAGGT
TGGCACTATCGGTGGTGGTACTATCCTCGAAGCGCAGGGTGCTATGCTTGACTTACTAGGCGTCCGTGGCTCTCACC
CCACCAACCCCGGCGATAACGCGCGTCAGCTGGCTCGTATTGTGGCAGCCGCAGTGCTTGCTGGCGAACTGAGTCTA
TGCTCTGCGCTTGCGGCTGGACATCTtGTCAGAGCGCACATGGCCCACAACCGCAGTGCCGCTCCCACTCGGTCAGC
GAcCCCGGTCTCAGCGGCTGTTGGTGCTACGCGGGACTGTCCATGACGTCTTCAAGATCTagggagcctgccagc
tgttgaattttgaccttcttaagctggcgggagacgtcgagtccaaccctgggcccatggcgcagctttcagttgaa
cagtttctcaacgagcaaaaacaggcggtggaaacagcgctctccgttatatagagcgcttagaagggccggcgaa
gctgaaaaaggcgatggcgtactcattggaggccggcggcaaacgaatccgtccgttgctgcttctgtccaccgttc
gggcgctcggcaaagacccggcggtcggattgcccgtcgcctgcgcgattgaaatgatccatacgtactctttgatc
catgatgatttgccgagcatggacaacgatgatttgcggcgcggcaagccgacgaaccataaagtgttcggcgaggc
gatggccatcttggcggggacgggttgttgacgtacgcgtttcaattgatcaccgaaatcgacgatgagcgcatcc
ctccttccgtccggcttcggctcatcgaacggctggcgaaagcggccggtccggaagggatggtcgccggtcaggca
gccgatatggaaggagaggggaaaacgctgacgctttcggagctcgaatacattcatcggcataaaaccgggaaaat
gctgcaatacagcgtgcacgccggcgccttgatcggcggcgctgatgcccggcaaacgcgggagcttgacgaattcg
ccgcccatctaggccttgcctttcaaattcgcgatgatattctcgatattgaaggggcagaagaaaaaatcggcaag
ccggtcggcagcgaccaaagcaacaacaaagcgacgtatccagcgttgctgtcgcttgccggcgcgaaggaaaagtt
ggcgttccatatcgaggcggcgcagcgccatttacggaacgccgacgttgacggcgccgcgctcgcctatatttgcg

FIG. 12C

```
aactggtcgccgcccgcgaccatTCTAGCcaccaccaccaccaccacgtgtgaattacaggtgaccgagctcGAATT
TCCCCGATCGTTCAAACATTTGGCAATAAAGTTTCTTATAAGATTGAATCCTGTTGCCGGTCTTGCGATGATTATCA
TATAATTTCTGTTGAATTACGTTAAGCATGTAATAATTAACATGTAATGCATGACGTTATTTATGAGATGGGTTTTT
ATGATTAGAGTCCCGCAATTATACATTTAATACGCGATAGAAAACAAAATATAGCGCGCAAACTAGGATAAATTATC
GCGCGCGGTGTCATCTATGTTACTAGATCGGGGAATTCgtaatcatgtcatagctgtttcctgtgtgaaattgttat
ccgctcacaattccacacaacatacgagccggaagcataaagtgtaaagcctggggtgcctaatgagtgagctaact
cacattaattgcgttgcgctcactgcccgctttccagtcgggaaacctgtcgtgccagctgcattaatgaatcggcc
aacgcgcggggaaaaggcggtttgcgtattggAGCTTGAGCTTGGATCAGATTGTCGTTTCCCGCCTTCAGTTTAAA
CTATCAGTGTTTGACAGGATATATTGGCGGGTAAACCTAAGAGAAAAGAGCGTTTATTAGAATAATCGGATATTTAA
AAGGGCGTGAAAAGGTTTATCCGTTCGTCCATTTGTATGTGCATGCCAACCACAGGGTTCCCCTCGGGATCAAAGTA
CT 7702 bp
```

FIG. 12D

SEQUENCE LISTING

```
<160> NUMBER OF SEQ ID NOS: 13

<210> SEQ ID NO 1
<211> LENGTH: 4680
<212> TYPE: DNA
<213> ORGANISM: Aspergillus nidulans

<400> SEQUENCE: 1
cttttctctg gaccctacgc caggattcct tcttttgac ctggaccacc ggtctggtga      60
tcttcccttc ccatatctca agcaatagtg ctgtggctcc cagcgcggca tctcattggc     120
tcccagttct gttccttcct aatagcgtaa gtctttctag gcggcagaat tcgccggctt     180
acttaaaact atttcttttc caagggtcac gggtggctca agctctttcg ctctggttga     240
gtgtgcttca ggggctcggt ggctgtgacg actcgactga cccgagcgtc ggtagaaata     300
gatcaagaag accagttctg ttggcaatcg attttgggaa cagcgactgc gattcttgtg     360
```

```
atttttttttt ttttgaatta ttggtcttac accgacatat cgctcacgac attgttgcgt     420
cttcgggtat gtctgcccca gcattggctc ttgcatcgcc tttcgtagtt gtcgccgctt     480
ttccctagtc gcctcgctcc gctccttgct agtggctggc ccattgcagg aaatcactcg     540
ctaacgccaa aaaatgtcag gtttctcgaa gtcccttatc cgcagaacat ataccctcct     600
gtttcctcgc ccatgtcatt gaacttcgaa aaccggtctt gatctattgc caaccgctgt     660
aaagacgacc tgcgcgattg aacatatcgg atagggtctc tcgctcggtg tgacccatcc     720
gcctcagcgc atctgttcag gcactccgag tcgtaccttt gtaccacgct cacaccgcct     780 cccccctcgta agctatcatg gcttccgtgt tgattcggag gaagtttggg acagaaggag     840
gcagtgatgc tgaaccttcc tggctgaagc gccaggttac cggctgcctg cagtcgatct     900
ctcgtcgcgc ctgcatccat cctatccaca caatcgtcgt gatcgccctt ctggcgagta     960
caacatatgt cggcctgctt gagggcagct tattcgattc gttcagaaat cgaacaatg    1020 ttgctggcca tgtggatgtt gactcgctcc tcctcggtaa caggagtctc cggttgggcg    1080
aaggcacatc atggaagtgg caagttgagg actcactgaa tcaggacgac caaaaggtgg    1140
ggaatcctga actaaagagg gagggtttgaa ctcatatcta atctcaacgg ctttttaggtc    1200 gaccaacatc ttgctttgac gactttgata tttccggact ctatttcgaa atccgcgtcg    1260
accgctcctg ctgccgacgc tatcccagtt cccgccaatg cctccgctca gcttctccct    1320
catacgccta atctcttctc gccattctct cacgactcct ctcttgtctt cacccttcct    1380
ttcgaccagg ttcctcaatt tctgagagcg gtccaggagc ttcctgaccc gacgcttgaa    1440
gatgacgaag gtgaacaaaa acgatggatt atgcgtgcta cccgcggccc ggtcagtgga    1500
ccgaatggaa ccatcagctc ctggctgtcg gatgcgtgga gttcctttgt ggatttgatc    1560
aaggtatccc ttgcgtgggc ttctctacat gtccgattgc taactactga tagcatgccg    1620
aaaccatcga tatcatcatc atgactctag gttatcttgc gatgtatctt agctttgcct    1680
ctctgttctt ctctatgaaa cagttggggt cgaagttttg gcttgctacc actgtccttt    1740
tctcgggcat gttcgctttc ctgtttgggt ctccctcgtta ccacgaagtt tggcgttccg    1800
atcaacattc tccttctatc agagggcctc ccgttccttg ttacgacaat tgggtttgaa    1860
aagccgatta ttctcaccag ggcagttctt agtgcgtcga tcgacaagaa acgccaaggt    1920
tcagcgactt cgactcccag ttctattcag gattcgattc agaccgcaat ccgagaacag    1980
ggtttcgaga ttattcgaga ctactgtatc gaaatctcca ttcttattgc aggagctgct    2040 tctgagttc agggcggtct gagacaattt tgcttcctcg ctgcttggat ccttttcttc    2100
gactgccttt tgctcttcac cttctacacg actatcctct gcattaagct tgagatcaca    2160
cgtatcaggc gccatgtgac ccttcgcaag gctctggagg aagatggtat tacgcagagt    2220
gttgccgaaa aggtcgcctc gagcaatgat tggtttggtg ccggatcgga caatagcgac    2280
gcagatgacg ctagtgtttt tggacggaaa atcaaatcga acaatgttcg ccgcttcaag    2340
ttcttgatgg tcggggtttt tgtgctggtc aacgtggtga atatgactgc aatccctttc    2400
cggaattcga gcttgtcacc tctctgcaat gtcttctcgc ctacaccgat agatcccttc    2460
aaggttgcta gaacggtct ggatgccatc tacgtttccg ctaaaagcca gaagttggag    2520
acattagtga cagttgtccc gcccatcaag tacaaacttg agtatccgtc ggtgcattat    2580
gctaagctgg gagagagcca gtctattgaa attgaatata ccgaccagct tctggatgct    2640
gtgggcggac acgtcctcaa cggcgttttg aagagcattg aggacccagt tatcagcaag    2700
```

```
tggatcattg cagtgttgac tttgagcata gtcctcaacg gctatctatt taacgccgca    2760
agatggagca tcaaggaacc acaagccgcc cccgctccta aggaaccggc caagccaaag    2820
gtctatccca aaatcgactt gaacgctggc cctaaggaga gcatggagga atgtgaggca    2880
atgctaaaag cgaaaaaggc agcctacctt agcgatgagg agctgattga actttcactc    2940
tctggcaaac ttcctggata tgctctggag aagtcattgg aaaatgagga acttatgagc    3000
cgtgttgatg ccttcacccg ggcagtcaaa atccgcaggg ctgtagtatc gaggaccccc    3060
gcaacttctg cagtcaccag ctctttggaa acttctaagc tgccctataa ggattacaat    3120
tatgcgcttg tccatggtgc ttgctgtgag aacgttattg caccctgcc tctgcctctt    3180
ggagttgccg gtccccttgt tattgatggt caaagctatt tcattcccat ggcaacaact    3240
gaaggtgttt tggtagccag tgccagtcga ggcgccaagg ctattaacgc tggtggtggt    3300
gcagtgactg tcttaactgg cgatggcatg actcgcggtc cctgtgtcgg gtttcctaca    3360
cttgcacgcg cagctgcagc taaggtctgg ctcgactccg aggagggtaa gagcgtcatg    3420
acagcagcat tcaactctac cagccgcttt gctcgactgc agcacctgaa gactgccctt    3480
gccggtacct acttgtatat ccggttcaag acgactactg gcgatgccat gggtatgaac    3540
atgatttcga aaggcgttga gaaagcactc catgtcatgg ctacagagtg tggattcgac    3600
gacatggcca ccatctctgt gtctggcaac ttttgtaccg acaagaaagc agctgctctc    3660
aactggattg acgccgcgg caaatcagtt gtggctgagg ctattatccc cggtgatgtt    3720
gtgcgcaatg tgctaaagag tgatgttgat gcattggtgg aattgaacac tagcaagaat    3780
ctgattggca gtgcaatggc aggtagcttg ggcggattca acgctcacgc atcaaacatt    3840
gttactgcaa tctttctcgc aactggtcaa gaccccgcgc aaaatgtgga gagcagcagc    3900
tgcattacca cgatgaagaa gtaagtagta tactttgatg tctttctctc ctggtcggcg    3960
ctaaccacgt tttagtacaa atggcaatct tcagatcgct gtgtctatgc cttcaattga    4020
ggttggcact atcggtggtg gtactatcct cgaagcgcag ggtgctatgc ttgacttact    4080
aggcgtccgt ggctctcacc ccaccaaccc cggcgacaac gcgcgtcagc tggctcgtat    4140
tgtggcagcc gcagtgcttg ctggcgaact gagtctatgc tctgcgcttg cggctggaca    4200
tcttgtcaga gcgcacatgg cccacaaccg cagtgccgct cccactcggt cagcgacccc    4260
ggtctcagcg gctgttggtg ctacgcgggg actgtccatg acgtcttcaa gatagatatc    4320
atgagtgcat gcctttctcc ttcctacctt ttacgataaa tacgatgcga ctaggctttc    4380
ttacgacggc cattctggaa ctaactgtcc ctcattcggt tcgctcaccc ggacttcttc    4440
cacttccggc acacattttc tgagctttt tacatgtggg ttttacggcg accgtgaatc    4500
atatggtcag cctcatttt ttttgggagt ctattgaata tactggagtc tgggcatata    4560
catagaactg cgctacggat tgacctgaac aagagatata ctaaaaagca aaggagacga    4620
gcagtcgctc tttgcacaag ggcagctgtt cgtcggacta catctgaaga tgattgtttg    4680
```

<210> SEQ ID NO 2
<211> LENGTH: 465
<212> TYPE: PRT
<213> ORGANISM: Aspergillus nidulans

<400> SEQUENCE: 2

Met Glu Glu Cys Glu Ala Met Leu Lys Ala Lys Lys Ala Ala Tyr Leu
1               5                   10                  15

Ser Asp Glu Glu Leu Ile Glu Leu Ser Leu Ser Gly Lys Leu Pro Gly
            20                  25                  30

-continued

```
Tyr Ala Leu Glu Lys Ser Leu Glu Asn Glu Leu Met Ser Arg Val
            35                  40                  45

Asp Ala Phe Thr Arg Ala Val Lys Ile Arg Arg Ala Val Val Ser Arg
 50                  55                  60

Thr Pro Ala Thr Ser Ala Val Thr Ser Ser Leu Glu Thr Ser Lys Leu
 65                  70                  75                  80

Pro Tyr Lys Asp Tyr Asn Tyr Ala Leu Val His Gly Ala Cys Cys Glu
                85                  90                  95

Asn Val Ile Gly Thr Leu Pro Leu Pro Leu Gly Val Ala Gly Pro Leu
            100                 105                 110

Val Ile Asp Gly Gln Ser Tyr Phe Ile Pro Met Ala Thr Thr Glu Gly
            115                 120                 125

Val Leu Val Ala Ser Ala Ser Arg Gly Ala Lys Ala Ile Asn Ala Gly
            130                 135                 140

Gly Gly Ala Val Thr Val Leu Thr Gly Asp Gly Met Thr Arg Gly Pro
145                 150                 155                 160

Cys Val Gly Phe Pro Thr Leu Ala Arg Ala Ala Ala Lys Val Trp
                165                 170                 175

Leu Asp Ser Glu Glu Gly Lys Ser Val Met Thr Ala Ala Phe Asn Ser
            180                 185                 190

Thr Ser Arg Phe Ala Arg Leu Gln His Leu Lys Thr Ala Leu Ala Gly
            195                 200                 205

Thr Tyr Leu Tyr Ile Arg Phe Lys Thr Thr Thr Gly Asp Ala Met Gly
            210                 215                 220

Met Asn Met Ile Ser Lys Gly Val Glu Lys Ala Leu His Val Met Ala
225                 230                 235                 240

Thr Glu Cys Gly Phe Asp Asp Met Ala Thr Ile Ser Val Ser Gly Asn
                245                 250                 255

Phe Cys Thr Asp Lys Lys Ala Ala Ala Leu Asn Trp Ile Asp Gly Arg
                260                 265                 270

Gly Lys Ser Val Val Ala Glu Ala Ile Ile Pro Gly Asp Val Val Arg
            275                 280                 285

Asn Val Leu Lys Ser Asp Val Asp Ala Leu Val Glu Leu Asn Thr Ser
            290                 295                 300

Lys Asn Leu Ile Gly Ser Ala Met Ala Gly Ser Leu Gly Gly Phe Asn
305                 310                 315                 320

Ala His Ala Ser Asn Ile Val Thr Ala Ile Phe Leu Ala Thr Gly Gln
                325                 330                 335

Asp Pro Ala Gln Asn Val Glu Ser Ser Cys Ile Thr Thr Met Lys
                340                 345                 350

Asn Thr Asn Gly Asn Leu Gln Ile Ala Val Ser Met Pro Ser Ile Glu
            355                 360                 365

Val Gly Thr Ile Gly Gly Gly Thr Ile Leu Glu Ala Gln Gly Ala Met
 370                 375                 380

Leu Asp Leu Leu Gly Val Arg Gly Ser His Pro Thr Asn Pro Gly Asp
385                 390                 395                 400

Asn Ala Arg Gln Leu Ala Arg Ile Val Ala Ala Val Leu Ala Gly
                405                 410                 415

Glu Leu Ser Leu Cys Ser Ala Leu Ala Ala Gly His Leu Val Arg Ala
                420                 425                 430

His Met Ala His Asn Arg Ser Ala Ala Pro Thr Arg Ser Ala Thr Pro
            435                 440                 445
```

Val Ser Ala Ala Val Gly Ala Thr Arg Gly Leu Ser Met Thr Ser Ser
    450                 455                 460

Arg
465

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
agaacgttat tggcaccctg                                                    20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gtgctttctc aacgcctttc                                                    20

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
gaggagggta agagcgtcat ga                                                 22

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
gtaccggcaa gggcagtct                                                     19

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ttgaatgcca ggctttggtt                                                    20

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
gcgcgcatga ccttctca                                                      18

-continued

```
<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
catcttgtca gagcgcacat                                             20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
caaatcatcg ttgtccatgc                                             20

<210> SEQ ID NO 11
<211> LENGTH: 7413
<212> TYPE: DNA
<213> ORGANISM: Artificial Sequence
<220> FEATURE:
<223> OTHER INFORMATION: pND9 T-DNA sequence
<220> FEATURE:
<221> NAME/KEY: misc_feature
<222> LOCATION: (1)..(333)
<223> OTHER INFORMATION: Left Board
<220> FEATURE:
<221> NAME/KEY: terminator
<222> LOCATION: (334)..(1047)
<220> FEATURE:
<221> NAME/KEY: gene
<222> LOCATION: (1107)..(1904)
<220> FEATURE:
<221> NAME/KEY: gene
<222> LOCATION: (1905)..(2132)
<220> FEATURE:
<221> NAME/KEY: promoter
<222> LOCATION: (2133)..(3500)
<220> FEATURE:
<221> NAME/KEY: promoter
<222> LOCATION: (3501)..(4441)
<220> FEATURE:
<221> NAME/KEY: gene
<222> LOCATION: (4442)..(4669)
<220> FEATURE:
<221> NAME/KEY: gene
<222> LOCATION: (4670)..(6694)
<220> FEATURE:
<221> NAME/KEY: terminator
<222> LOCATION: (6714)..(6987)
<220> FEATURE:
<221> NAME/KEY: misc_feature
<222> LOCATION: (7213)..(7413)
<223> OTHER INFORMATION: Right Board

<400> SEQUENCE: 11
tgatcacagg cagcaacgct ctgtcatcgt tacaatcaac atgctaccct ccgcgagatc      60
atccgtgttt caaacccggc agcttagttg ccgttcttcc gaatagcatc ggtaacatga     120
gcaaagtctg ccgccttaca acggctctcc cgctgacgcc gtcccggact gatgggctgc     180
ctgtatcgag tggtgatttt gtgccgagct gccggtcggg gagctgttgg ctggctggtg     240
gcaggatata ttgtggtgta aacaaattga cgcttagaca acttaataac acattgcgga     300
cgtttttaat gtactgaatt aacgccgaat tgcttaatta agtcctgctg agcctcgaca     360
tgttgtcgca aaattcgccc tggacccgcc aacgatttg tcgtcactgt caaggtttga     420
```

```
cctgcacttc atttggggcc cacatacacc aaaaaaatgc tgcataattc tcggggcagc      480
aagtcggtta cccggccgcc gtgctggacc gggttgaatg gtgcccgtaa ctttcggtag      540
agcggacggc caatactcaa cttcaaggaa tctcacccat gcgcgccggc ggggaaccgg      600
agttcccttc agtgaacgtt attagttcgc cgctcggtgt gtcgtagata ctagcccctg      660
gggccttttg aaatttgaat aagatttatg taatcagtct tttaggtttg accggttctg      720 ccgcttttt taaaattgga tttgtaataa taaaacgcaa ttgttgtta ttgtggcgct        780 ctatcataga tgtcgctata aacctattca gcacaatata ttgttttcat tttaatattg      840
tacatataag tagtagggta caatcagtaa attgaacgga gaatattatt cataaaaata      900
cgatagtaac gggtgatata ttcattagaa tgaaccgaaa ccggcggtaa ggatctgagc      960
tacacatgct caggtttttt acaacgtgca caacagaatt gaaagcaaat atcatgcgat     1020
cataggcgtc tcgcatatct cattaaagag ctcgagcttg tcgatcgact ctagctagag     1080
gatcgatccg aacccagag tcccgctcag aagaactcgt caagaaggcg atagaaggcg      1140
atgcgctgcg aatcggagc ggcgataccg taaagcacga ggaagcggtc agcccattcg      1200
ccgccaagct cttcagcaat atcacgggta gccaacgcta tgtcctgata gcggtccgcc     1260
acacccagcc ggcacagtc gatgaatcca gaaaagcggc cattttccac catgatattc      1320
ggcaagcagg catcgccatg tgtcacgacg agatcctcgc cgtcgggcat gcgcgccttg     1380
agcctggcga acagttcggc tggcgcgagc cctgatgct cttcgtccag atcatcctga      1440
tcgacaagac cggcttccat ccgagtacgt gctcgctcga tgcgatgttt cgcttggtgg     1500
tcgaatggga aggtagccgg atcaagcgta tgcagccgcc gcattgcatc agccatgatg     1560
gatactttct cggcaggagc aaggtgagat gacaggagat cctgccccgg cacttcgccc     1620
aatagcagcc agtcccttcc cgcttcagtg acaacgtcga gcacagctgc gcaaggaacg     1680
cccgtcgtgg ccagccacga tagccgcgct gcctcgtcct ggagttcatt cagggcaccg     1740
gacaggtcgg tcttgacaaa aagaaccggg cgccccctgcg ctgacagccg gaacacggcg     1800
gcatcagagc agccgattgt ctgttgtgcc cagtcatagc cgaatagcct ctccacccaa     1860
gcggccggag aacctgcgtg caatccatct tgttcaatcc ccataccacc tcttaagcgg     1920
agcaccaaat ggagggtaga ctccttctgg atgttgtagt cggcaagagt acgaccatcc     1980
tcaagctgct ttccggcgaa aatcaaacgc tgctggtctg ggggaatccc ttccttgtcc     2040
tggatcttgg ctttgacatt gtcgatggtg tcggaagact caacctctag ggtgatcgtc     2100 ttcccgtta gggtcttcac gaagatctgc atctgcaaag tcataaaaac aacawtcaga      2160
acaacggaaa aaaactcaaa ttatagggct tttcacactc cctgattaac tgattcgaga     2220
attaaaacca aacaatctaa aacacggga aaaaactcaa attttagggc ttttcatca       2280 aaacaaccgg aaaacctcaa attttagggc tttagaatca aaccgacgaa aaatcacaaa     2340
ttctagggct ttttcatcaa atcaaccgga aaaaaaaat caaattcaag accttttca       2400 tcaaaccacc ataaaaaaac tcaaattcta gggcattatc atcaaatcac ccggaaaacc     2460
ccacattttg ggcctttaga atcaaaccga cgaaaaaact ctaattttaa acctttggca     2520
tcaaatcgac ggaaaaaaac tcaaattagg ggctttttca tcaaaacaac ggaaaaaaaa     2580
ctcaaatttt agggctttaa cagcacctgc ttagctaatt cgagaatcta aacagacaaa     2640
aaccaaaaaa tagagaagat ttctaacctt gaaagagaaa tttaaaggca attgagagaa     2700
attataatag aagtcagata gaagatgaaa aaatgaggtg cagaaaggtt cctttatag      2760 atggcatggc cgactctaga cgaaaccgcc tcatagggtt agccaattat atgatgacac     2820
```

```
gtgtaataat gaggtgtagt gtagcaaaac aacacgcaaa agctaccgtt tcttttttatt      2880 tatgtggtgg ggaaaattag gagaatgagg ttgacgctta cacgctcctt tagaaaaaac      2940
tagaaaaatg taggtcatag taaaaaaata tactaaaaat aacttaattt tattttaggt      3000
attggccaaa atctggggaa aaaatttggt ctgaatttaa ttagaatgat attttattta      3060
tgttatttta ttttttaaaa tattttttatt cttttaactt taatacattt taactaaaaa      3120
ataaagaata tatcaattta ttttaaaata aaaaaatatt ataattttct taattttcta      3180
tctaattttt ttgatcattt agcatttttct tttttattaa ttaatatatg ctctaatata      3240
gcgcttttta agtatattgt gaacataacc ttaaatataa gagtttaaat attagcaaat      3300
tagggtataa tactcgttga taatcgcact ttaatctttt ttcttatatt atgtattgct      3360
cctttttttt acattatttt tttattgtta ttgacctcat attgataagt atttgttatc      3420
taaatttgat tgaaaatatt ttatttaaat tgagtatata ttagaaacac ttttttcttt      3480
ttatataaga ggtaagtatc aagcttgcat gcctgcaggt ccgattgaga cttttcaaca      3540
aagggtaata tccggaaacc tcctcggatt ccattgccca gctatctgtc actttattgt      3600
gaagatagtg gaaaggaag gtggctccta caaatgccat cattgcgata aaggaaaggc      3660
catcgttgaa gatgcctctg ccgacagtgg tcccaaagat ggaccccac ccacgaggag      3720 catcgtggaa aaagaagacg ttccaaccac gtcttcaaag caagtggatt gatgtgatgg      3780
tccgattgag acttttcaac aaagggtaat atccggaaac ctcctcggat tccattgccc      3840
agctatctgt cactttattg tgaagatagt ggaaaggaa ggtggctcct acaaatgcca      3900
tcattgcgat aaaggaaagg ccatcgttga agatgcctct gccgacagtg gtcccaaaga      3960
tggaccccca cccacgagga gcatcgtgga aaagaagac gttccaacca cgtcttcaaa      4020
gcaagtggat tgatgtgata tctccactga cgtaagggat gacgcacaat cccactatcc      4080
ttcgcaagac ccttcctcta tataaggaag ttcatttcat ttggagagga gatctttta      4140 ttttttaattt tctttcaaat acttccacca tggtatatat aggaagttca tttcatttgg      4200
aatggacacg tgttgtcatt tctcaacaca acatatacaa aacaaacgaa tctcaagcaa      4260
tcaagcattc taccaataac tatttacaat tacatctagt taaacaatgt caggcccaat      4320
tacgaagaaa agggcttgta aaaccctaat aaagtggcac tggcagagct tacactctca      4380
ttccatcaac aaagaaaccc taaaagccgc agcgccactg atttctctcc tccaggcgaa      4440
gatgcagatc ttcgtgaaga ccctaacggg gaagacgatc accctagagg ttgagtcttc      4500
cgacaccatc gacaatgtca aagccaagat ccaggacaag gaagggattc ccccagacca      4560
gcagcgtttg attttcgccg gaaagcagct tgaggatggt cgtactcttg ccgactacaa      4620
catccagaag gagtctaccc tccatttggt gctccgctta agaggtggta tgttacgtcc      4680
tgtagaaacc ccaacccgtg aaatcaaaaa actcgacggc ctgtgggcat tcagtctgga      4740
tcgcgaaaac tgtggaattg atcagcgttg gtgggaaagc gcgttacaag aaagccgggc      4800
aattgctgtg ccaggcagtt ttaacgatca gttcgccgat gcagatattc gtaattatgc      4860
gggcaacgtc tggtatcagc gcgaagtctt tataccgaaa ggttgggcag gccagcgtat      4920
cgtgctgcgt ttcgatgcgg tcactcatta cggcaaagtg tgggtcaata atcaggaagt      4980
gatggagcat cagggcggct atacgccatt tgaagccgat gtcacgccgt atgttattgc      5040
cgggaaaagt gtacgtaagt ttctgcttct acctttgata tatatataat aattatcatt      5100
aattagtagt aatataatat ttcaaatatt ttttcaaaa taaagaatg tagtatatag      5160
```

```
caattgcttt tctgtagttt ataagtgtgt atattttaat ttataacttt tctaatatat   5220
gaccaaaatt tgttgatgtg caggtatcac cgtttgtgtg aacaacgaac tgaactggca   5280
gactatcccg ccgggaatgg tgattaccga cgaaaacggc aagaaaaagc agtcttactt   5340
ccatgatttc tttaactatg ccggaatcca tcgcagcgta atgctctaca ccacgccgaa   5400
cacctgggtg gacgatatca ccgtggtgac gcatgtcgcg caagactgta accacgcgtc   5460
tgttgactgg caggtggtgg ccaatggtga tgtcagcgtt gaactgcgtg atgcggatca   5520
acaggtggtt gcaactggac aaggcactag cgggactttg caagtggtga atccgcacct   5580
ctggcaaccg ggtgaaggtt atctctatga actgtgcgtc acagccaaaa gccagacaga   5640
gtgtgatatc tacccgcttc gcgtcggcat ccggtcagtg gcagtgaagg gccaacagtt   5700
cctgattaac cacaaaccgt tctactttac tggctttggt cgtcatgaag atgcggactt   5760
acgtggcaaa ggattcgata acgtgctgat ggtgcacgac cacgcattaa tggactggat   5820
tggggccaac tcctaccgta cctcgcatta cccttacgct gaagagatgc tcgactgggc   5880
agatgaacat ggcatcgtgg tgattgatga aactgctgct gtcggcttta acctctcttt   5940
aggcattggt ttcgaagcgg gcaacaagcc gaaagaactg tacagcgaag aggcagtcaa   6000
cggggaaact cagcaagcgc acttacaagc gattaaagag ctgatagcgc gcgacaaaaa   6060
ccacccaagc gtggtgatgt ggagtattgc caacgaaccg gatacccgtc cgcaagtgca   6120
cgggaatatt tcgccactgg cggaagcaac gcgtaaactc gacccgacgc gtccgatcac   6180
ctgcgtcaat gtaatgttct gcgacgctca caccgatacc atcagcgatc tctttgatgt   6240
gctgtgcctg aaccgttatt acggatggta tgtccaaagc ggcgatttgg aaacggcaga   6300
gaaggtactg gaaaaagaac ttctggcctg gcaggagaaa ctgcatcagc cgattatcat   6360
caccgaatac ggcgtggata cgttagccgg gctgcactca atgtacaccg acatgtggag   6420
tgaagagtat cagtgtgcat ggctggatat gtatcaccgc gtctttgatc gcgtcagcgc   6480
cgtcgtcggt gaacaggtat ggaatttcgc cgattttgcg acctcgcaag gcatattgcg   6540
cgttggcggt aacaagaaag ggatcttcac tcgcgaccgc aaaccgaagt cggcggcttt   6600
tctgctgcaa aaacgctgga ctggcatgaa cttcggtgaa aaaccgcagc agggaggcaa   6660
acaatctagc caccaccacc accaccacgt gtgaattaca ggtgaccgag ctcgaatttc   6720
cccgatcgtt caaacatttg gcaataaagt ttcttataag attgaatcct gttgccggtc   6780
ttgcgatgat tatcatataa tttctgttga attacgttaa gcatgtaata attaacatgt   6840
aatgcatgac gttatttatg agatgggttt ttatgattag agtcccgcaa ttatacattt   6900
aatacgcgat agaaaacaaa atatagcgcg caaactagga taaattatcg cgcgcggtgt   6960
catctatgtt actagatcgg ggaattcgta atcatgtcat agctgtttcc tgtgtgaaat   7020
tgttatccgc tcacaattcc acacaacata cgagccggaa gcataaagtg taaagcctgg   7080
ggtgcctaat gagtgagcta actcacatta attgcgttgc gctcactgcc cgctttccag   7140
tcgggaaacc tgtcgtgcca gctgcattaa tgaatcggcc aacgcgcggg gaaaggcgg    7200
tttgcgtatt ggagcttgag cttggatcag attgtcgttt cccgccttca gtttaaacta   7260
tcagtgtttg acaggatata ttggcgggta aacctaagag aaaagagcgt ttattagaat   7320
aatcggatat ttaaaagggc gtgaaaaggt ttatccgttc gtccatttgt atgtgcatgc   7380
caaccacagg gttcccctcg ggatcaaagt act                                7413

<210> SEQ ID NO 12
<211> LENGTH: 9472
```

```
<212> TYPE: DNA
<213> ORGANISM: Artificial Sequence
<220> FEATURE:
<223> OTHER INFORMATION: pND9_427P-HMGR-2A-FPPS_T-DNA
<220> FEATURE:
<221> NAME/KEY: misc_feature
<222> LOCATION: (1)..(333)
<223> OTHER INFORMATION: Left Board
<220> FEATURE:
<221> NAME/KEY: terminator
<222> LOCATION: (334)..(1047)
<220> FEATURE:
<221> NAME/KEY: gene
<222> LOCATION: (1107)..(1904)
<220> FEATURE:
<221> NAME/KEY: gene
<222> LOCATION: (1905)..(2132)
<220> FEATURE:
<221> NAME/KEY: promoter
<222> LOCATION: (2133)..(3500)
<220> FEATURE:
<221> NAME/KEY: promoter
<222> LOCATION: (3501)..(6362)
<220> FEATURE:
<221> NAME/KEY: gene
<222> LOCATION: (6363)..(7760)
<220> FEATURE:
<221> NAME/KEY: gene
<222> LOCATION: (7761)..(7832)
<220> FEATURE:
<221> NAME/KEY: gene
<222> LOCATION: (7833)..(8753)
<220> FEATURE:
<221> NAME/KEY: terminator
<222> LOCATION: (8773)..(9046)
<220> FEATURE:
<221> NAME/KEY: misc_feature
<222> LOCATION: (9272)..(9472)
<223> OTHER INFORMATION: Right Board

<400> SEQUENCE: 12
tgatcacagg cagcaacgct ctgtcatcgt tacaatcaac atgctaccct ccgcgagatc      60
atccgtgttt caaacccggc agcttagttg ccgttcttcc gaatagcatc ggtaacatga     120
gcaaagtctg ccgccttaca acggctctcc cgctgacgcc gtcccggact gatgggctgc     180
ctgtatcgag tggtgatttt tgtgccgagc tgccggtcgg gagctgttgg ctggctggtg     240
gcaggatata ttgtggtgta aacaaattga cgcttagaca acttaataac acattgcgga     300
cgtttttaat gtactgaatt aacgccgaat tgcttaatta agtcctgctg agcctcgaca     360
tgttgtcgca aaattcgccc tggacccgcc aacgatttg tcgtcactgt caaggtttga      420
cctgcacttc atttgggcc cacatacacc aaaaaaatgc tgcataattc tcggggcagc     480
aagtcggtta cccggccgcc gtgctggacc gggttgaatg gtgcccgtaa ctttcggtag     540
agcggacggc caatactcaa cttcaaggaa tctcacccat gcgcgccggc ggggaaccgg     600
agttcccttc agtgaacgtt attagttcgc cgctcggtgt gtcgtagata ctagcccctg     660
gggccttttg aaatttgaat aagatttatg taatcagtct tttaggtttg accggttctg     720 ccgcttttt taaaattgga tttgtaataa taaaacgcaa ttgttgtta ttgtggcgct       780 ctatcataga tgtcgctata aacctattca gcacaatata ttgttttcat tttaatattg     840
tacatataag tagtagggta caatcagtaa attgaacgga gaatattatt cataaaaata     900
cgatagtaac gggtgatata ttcattagaa tgaaccgaaa ccggcggtaa ggatctgagc     960
tacacatgct caggtttttt acaacgtgca caacagaatt gaaagcaaat atcatgcgat    1020
cataggcgtc tcgcatatct cattaaagag ctcgagcttg tcgatcgact ctagctagag    1080
gatcgatccg aaccccagag tccgctcag aagaactcgt caagaaggcg atagaaggcg    1140
```

```
atgcgctgcg aatcgggagc ggcgataccg taaagcacga ggaagcggtc agcccattcg    1200
ccgccaagct cttcagcaat atcacgggta gccaacgcta tgtcctgata gcggtccgcc    1260
acacccagcc ggccacagtc gatgaatcca gaaaagcggc cattttccac catgatattc    1320
ggcaagcagg catcgccatg tgtcacgacg agatcctcgc cgtcgggcat gcgcgccttg    1380
agcctggcga acagttcggc tggcgcgagc ccctgatgct cttcgtccag atcatcctga    1440
tcgacaagac cggcttccat ccgagtacgt gctcgctcga tgcgatgttt cgcttggtgg    1500
tcgaatgggc aggtagccgg atcaagcgta tgcagccgcc gcattgcatc agccatgatg    1560
gatactttct cggcaggagc aaggtgagat gacaggagat cctgccccgg cacttcgccc    1620
aatagcagcc agtcccttcc cgcttcagtg acaacgtcga gcacagctgc gcaaggaacg    1680
cccgtcgtgg ccagccacga tagccgcgct gcctcgtcct ggagttcatt cagggcaccg    1740
gacaggtcgg tcttgacaaa agaaccgggc gcccctgcg ctgacagccg gaacacggcg    1800
gcatcagagc agccgattgt ctgttgtgcc cagtcatagc cgaatagcct ctccacccaa    1860
gcggccggag aacctgcgtg caatccatct tgttcaatcc ccataccacc tcttaagcgg    1920
agcaccaaat ggagggtaga ctccttctgg atgttgtagt cggcaagagt acgaccatcc    1980
tcaagctgct ttccggcgaa atcaaacgc tgctggtctg ggggaatccc ttccttgtcc      2040
tggatcttgg ctttgacatt gtcgatggtg tcggaagact caacctctag ggtgatcgtc    2100
ttccccgtta gggtcttcac gaagatctgc atctgcaaag tcataaaaac aacawtcaga    2160 acaacgaaa aaaactcaaa ttatagggct tttcacactc cctgattaac tgattcgaga     2220
attaaaacca acaatctaa aacacgggga aaaaactcaa attttagggc ttttcatca      2280 aaacaaccgg aaaacctcaa attttagggc tttagaatca aaccgacgaa aaatcacaaa    2340
ttctagggct ttttcatcaa atcaaccgga aaaaaaaaat caaattcaag acctttttca    2400
tcaaaccacc ataaaaaaac tcaaattcta gggcattatc atcaaatcac ccggaaaacc    2460
ccacattttg ggcctttaga atcaaaccga cgaaaaaact ctaattttaa accttggca    2520 tcaaatcgac ggaaaaaaac tcaaattagg ggcttttttca tcaaaacaac ggaaaaaaaa   2580 ctcaaattt agggctttaa cagcacctgc ttagctaatt cgagaatcta aacagacaaa     2640
aaccaaaaaa tagagaagat ttctaacctt gaaagagaaa tttaaaggca attgagagaa    2700
attataatag aagtcagata gaagatgaaa aaatgaggtg cagaaaggtt cctttatag     2760 atggcatggc cgactctaga cgaaaccgcc tcatagggtt agccaattat atgatgacac    2820
gtgtaataat gaggtgtagt gtagcaaaac aacacgcaaa agctaccgtt tcttttatt    2880 tatgtggtgg ggaaattag gagaatgagg ttgacgctta cacgctcctt tagaaaaaac    2940 tagaaaatg taggtcatag taaaaaaata tactaaaaat aacttaattt tattttaggt    3000
attggccaaa atctggggaa aaaatttggt ctgaatttaa ttagaatgat attttattta     3060
tgttatttta ttttttaaaa tattttattt cttttaactt taatacattt taactaaaaa    3120
ataaagaata tatcaattta ttttaaaata aaaaaatatt ataatttct taattttcta     3180 tctaattttt ttgatcattt agcattttct ttttttattaa ttaatatatg ctctaatata   3240
gcgcttttta agtatattgt gaacataacc ttaaatataa gagtttaaat attagcaaat    3300
tagggtataa tactcgttga taatcgcact ttaatctttt ttcttatatt atgtattgct    3360 ccttttttt acattatttt tttattgtta ttgacctcat attgataagt atttgttatc     3420 taaattgat tgaaaatatt ttatttaaat tgagtatata ttagaaacac ttttctttt      3480
```

```
ttatataaga ggtaagtatc aagcttgcat gcctgcaggc ggcttgcttg gtcttacttc    3540
atcgtcgaga aaagaaagaa gacttctatc tacaagtttta actcaaacgt agttctttta    3600
tttttttggg tgtgaagtag tgtcaaacca aatacccctt tctaaacaac tattgtttgt    3660
gaatataggt tgtgttgttt ctcattcgga agaccaagtc ccacacccta acttcactga    3720
tgagaacaac ctccgcactc tgggctgttt aaatccccgg ttgaaatcat ccaaccaaac    3780
tctctttatt tcgagattga aaaggtcgat caattatgat caaagataat gcctagtggc    3840
gacgagccca ctaggaagac ctttgattac aaaggttacc gtggtctagg tttataatgg    3900
attcaattaa tcaaagtgcc tccaactcaa gctcattttc ctatcaggag aaaacaatgc    3960
ataaaaaagg gatggccgtc aaaaagccga cccttcaatc caaaagcgtt caaattcccg    4020
cctacatcag ctcgacctgt tgttcgctc taattaggat catcagaata tcttgacaga    4080
tttttttgaa aagcttaact tgcaagcgga gaatgccgag tctctaccca cttttttgagc    4140 ttgcaaagta gcaatatgaa atttcttggg cacttacccg tcgtgcttga gatctaaact    4200
gcttacaaca accttgacct ggtccaatga aaagagaaag acttaaagag ctccctctat    4260
aggtgactcc tccaataaga ctcttagggt gcatgtcaaa acccgctaag ttaggagtat    4320
acataaaatt ttggccgata taaggattaa ataaccaaa taatataacg aaaataaatt    4380
taaacaataa aaaataataa agagatgtat ccattctttt tcactcaaat tgtattttta    4440
gaaattatag tcaaatttac tatcaaaatt taaaaaatta attttaaaa ttatacatgc    4500 catgaatttg aaatttgaaa aagggaaaaa gaggagaagc atctagtaag gctctaatta    4560
attgcgtaac cgtgtcttct aaaatatccg aagaaattgc gtaagcgctg agccataggc    4620
ccatacgttc cctctctgtg acggcaaagc ggttactata aatacagatc ttccctttttt    4680 caaccaaatc cccaaatcat catccttctc tagcgcaact tctctcggaa aaagcatct    4740 cctcctcctc tcgttttctc gataatctcc ttgtacactg tttcttcttc tcaaggtaat    4800
ggtcttttct tctctcgatt caatcgtttg ttgaagtgat ttagatttat gcaggttttt    4860
gtattataaa tgtatgaaca gaattatatg aacggaattt acctttgttt cttgtttatc    4920
gatcagatct gcacggaatt agtcgatttg agaactttt gaaatcgatg atgtatgttt    4980
tttctgttga tgatgctata gcgtttaatt tcgtttgatt tgctcttgtt ttggtttcca    5040
tatggtcgaa ttgttgaagt ttcgtagttt gattagtttt gtatcctatc tagggttttt    5100
tgtgatcaca attaatcaat ttgaaatggt gatgcttgct ttttctgttg atgatgttat    5160
agcattgaat ttcgttgatt tgcttgattt ttttggtcact gtttaataga aattgttcaa    5220
gtttccaggt ttgattaatt gtgtcctgtg tagggatatt tatgatcaaa attaatcaat    5280
ttgaagaaaa cactatgttt aatggataat atatgctttt ttattttttct tgttgatgat    5340 gttatagtct tgtatattct cgtgttgttc catttttctg ttttctattt gcttgaaatt    5400
gttcaagttt ctaggtttga ttatttgtgt gctatctagg gattttttgtg atcaaaatta    5460 caaatctagg ttaaatggat gatgcatgct tttgctgctg atgatttata gccttgaatt    5520
ttgtcgattt gcttcatttt tggtctctat ttaatgaaat tgttgaagtt tctaggtttg    5580
attaattgtg tcttgtctag gtttttttgcg aacaaattga actagattta aataaattta    5640
ggagtcctca atttttttgt ttgttaactc ttattgatct gttttttttaa tgtatttatt    5700 cttgtgtggg cacattgtta ttctcttctg attatgctac gatcgtgaac ttgatttgat    5760
ttacaataca tccaattgtg ggtttgcatc cctcttaaaa tgataagtat agttgttct    5820 aggtagaatt ggatgcttct aggggcctac tgatttgttt gtaaaaatgg ttgttcattg    5880
```

```
gattgaattt ttattaaaga aaaaatctga aattctaata attcttgtaa attaggttga    5940
tgtcagatct atttattttc ttctttgttt ggttgactgg tcttctggtg gctctctgat    6000
tagtgtaatt atagttgact ttggatatgt tgcttttgct ctttgtatgg tttctaatca    6060
attgggattc ttttcttatt ctctcctaat ttgcctctgg tttgatatat tcaatttaa    6120 cttcaattgt ttcgtgggat gacttgtccc aaattaaaca agttctgaga tttgtgtgca    6180
agctatgcta tgggtgttca tattatgtgg tagttcgctg ctgtaagagg gagattgcag    6240
aacctttatt atatcgtctt ttcttttggg acttccaaag cttgctagtt tgtcatctct    6300
gcctgattga atagaatttt tgacagttgt gtgcttgaat atatttcaga ccggtcgcca    6360
ccatggagga atgtgaggca atgctaaaag cgaaaaggc agcctacctt agcgatgagg    6420
agctgattga actttcactc tctggcaaac ttcctggata tgctctggag aagtcattgg    6480
aaaatgagga acttatgagc cgtgttgatg ccttcacccg ggcagtcaaa atccgcaggg    6540
ctgtagtatc gaggaccccc gcaacttctg caatcaccag ctctttggaa acttctaagc    6600
tgccctataa ggattacaat tatgcgcttg tccatggtgc ttgctgtgag aacgttattg    6660
gcaccctgcc tctgcctctt ggagttgccg gtccccttgt tattgatggt caaagctatt    6720
tcattcccat ggcaacaact gaaggtgttt tggtagccag tgccagtcga ggcgccaagg    6780
ctattaacgc tggtggtggt gcagtgactg tcttaactgg cgatggcatg actcgcggtc    6840
cctgtgtcgg gtttcctaca cttgcacgcg cagctgcagc taaggtctgg ctcgactccg    6900
aggagggtaa gagcgtcatg acagcagcat tcaactctac cagccggttt gctcgactgc    6960
agcacctgaa gactgcccctt gccggtacct acttgtatat ccggttcaag acgactactg    7020
gcgatgccat gggtatgaac atgatttcga aaggcgttga gaaagcactc catgtcatgg    7080
ctacagagtg tagattcgac gacatggcca ccatctctgt gtctggcaac ttttgtaccg    7140
acaagaaagc agctgctctc aactggattg acggccgcgg caaatcagtt gtggctgagg    7200
ctattatccc cggtgatgtt gtgcgcaatg tgctaaagag tggtgttgat gcattggtgg    7260
aattgaacac tagcaagaat ctgattggca gtgcaatggc aggtagcttg ggcggattca    7320
acgctcacgc atcaaacatt gttactgcaa tctttctcgc aactggtcaa gaccccgcgc    7380
aaaatgtgga gagcagcagc tgcattacca cgatgaagaa tacaaatggc aatcttcaga    7440
tcgctgtgtc tatgccttca attgaggttg gcactatcgg tggtggtact atcctcgaag    7500
cgcagggtgc tatgcttgac ttactaggcg tccgtggctc tcaccccacc aaccccggcg    7560
ataacgcgcg tcagctggct cgtattgtgg cagccgcagt gcttgctggc gaactgagtc    7620
tatgctctgc gcttgcggct ggacatcttg tcagagcgca catggcccac aaccgcagtg    7680
ccgctcccac tcggtcagcg accccggtct cagcggctgt tggtgctacg cggggactgt    7740
ccatgacgtc ttcaagatct aggggagcct gccagctgtt gaattttgac cttcttaagc    7800
tggcgggaga cgtcgagtcc aaccctgggc ccatggcgca gctttcagtt gaacagtttc    7860
tcaacgagca aaaacaggcg gtggaaacag cgctctcccg ttatatagag cgcttagaag    7920
ggccggcgaa gctgaaaaag gcgatggcgt actcattgga ggccggcggc aaacgaatcc    7980
gtccgttgct gcttctgtcc accgttcggg cgctcggcaa agaccggcg gtcggattgc    8040 ccgtcgcctg cgcgattgaa atgatccata cgtactcttt gatccatgat gatttgccga    8100
gcatggacaa cgatgatttg cggcgcggca agccgacgaa ccataaagtg ttcggcgagg    8160
cgatggccat cttggcgggg gacggggttgt tgacgtacgc gtttcaattg atcaccgaaa    8220
```

-continued

```
tcgacgatga gcgcatccct ccttccgtcc ggcttcggct catcgaacgg ctggcgaaag    8280
cggccggtcc ggaagggatg gtcgccggtc aggcagccga tatggaagga gaggggaaaa    8340
cgctgacgct ttcggagctc gaatacattc atcggcataa aaccgggaaa atgctgcaat    8400
acagcgtgca cgccggcgcc ttgatcggcg gcgctgatgc ccggcaaacg cgggagcttg    8460
acgaattcgc cgcccatcta ggccttgcct ttcaaattcg cgatgatatt ctcgatattg    8520
aaggggcaga agaaaaaatc ggcaagccgg tcggcagcga ccaaagcaac aacaaagcga    8580
cgtatccagc gttgctgtcg cttgccggcg cgaaggaaaa gttggcgttc catatcgagg    8640
cggcgcagcg ccatttacgg aacgccgacg ttgacggcgc cgcgctcgcc tatatttgcg    8700
aactggtcgc cgcccgcgac cattctagcc accaccacca ccaccacgtg tgaattacag    8760
gtgaccgagc tcgaatttcc ccgatcgttc aaacatttgg caataaagtt tcttataaga    8820
ttgaatcctg ttgccggtct tgcgatgatt atcatataat ttctgttgaa ttacgttaag    8880
catgtaataa ttaacatgta atgcatgacg ttatttatga gatgggtttt tatgattaga    8940
gtcccgcaat tatacattta atacgcgata gaaaacaaaa tatagcgcgc aaactaggat    9000
aaattatcgc gcgcggtgtc atctatgtta ctagatcggg gaattcgtaa tcatgtcata    9060
gctgtttcct gtgtgaaatt gttatccgct cacaattcca cacaacatac gagccggaag    9120
cataaagtgt aaagcctggg gtgcctaatg agtgagctaa ctcacattaa ttgcgttgcg    9180
ctcactgccc gctttccagt cgggaaacct gtcgtgccag ctgcattaat gaatcggcca    9240
acgcgcgggg aaaaggcggt ttgcgtattg gagcttgagc ttggatcaga ttgtcgtttc    9300
ccgccttcag tttaaactat cagtgtttga caggatatat tggcgggtaa acctaagaga    9360
aaagagcgtt tattagaata atcggatatt taaagggcg tgaaaaggtt tatccgttcg    9420
tccatttgta tgtgcatgcc aaccacaggg ttcccctcgg gatcaaagta ct             9472
```

```
<210> SEQ ID NO 13
<211> LENGTH: 7702
<212> TYPE: DNA
<213> ORGANISM: Artificial Sequence
<220> FEATURE:
<223> OTHER INFORMATION: pND9_427P-HMGR-2A-FPPS_T-DNA
<220> FEATURE:
<221> NAME/KEY: misc_feature
<222> LOCATION: (1)..(333)
<223> OTHER INFORMATION: Left Board
<220> FEATURE:
<221> NAME/KEY: terminator
<222> LOCATION: (334)..(1047)
<220> FEATURE:
<221> NAME/KEY: gene
<222> LOCATION: (1107)..(1904)
<220> FEATURE:
<221> NAME/KEY: gene
<222> LOCATION: (1905)..(2132)
<220> FEATURE:
<221> NAME/KEY: promoter
<222> LOCATION: (2133)..(3500)
<220> FEATURE:
<221> NAME/KEY: promoter
<222> LOCATION: (3501)..(4592)
<220> FEATURE:
<221> NAME/KEY: gene
<222> LOCATION: (4593)..(5990)
<220> FEATURE:
<221> NAME/KEY: gene
<222> LOCATION: (5991)..(6062)
<220> FEATURE:
<221> NAME/KEY: gene
<222> LOCATION: (6063)..(6983)
<220> FEATURE:
<221> NAME/KEY: terminator
```

<222> LOCATION: (7003)..(7276)
<220> FEATURE:
<221> NAME/KEY: misc_feature
<222> LOCATION: (7502)..(7702)
<223> OTHER INFORMATION: Right Board

<400> SEQUENCE: 13

| | | |
|---|---|---|
| tgatcacagg cagcaacgct ctgtcatcgt tacaatcaac atgctaccct ccgcgagatc | 60 |
| atccgtgttt caaacccggc agcttagttg ccgttcttcc gaatagcatc ggtaacatga | 120 |
| gcaaagtctg ccgccttaca acggctctcc cgctgacgcc gtcccggact gatgggctgc | 180 |
| ctgtatcgag tggtgatttt gtgccgagct gccggtcggg gagctgttgg ctggctggtg | 240 |
| gcaggatata ttgtggtgta aacaaattga cgcttagaca acttaataac acattgcgga | 300 |
| cgttttaat gtactgaatt aacgccgaat tgcttaatta agtcctgctg agcctcgaca | 360 |
| tgttgtcgca aaattcgccc tggacccgcc caacgatttg tcgtcactgt caaggtttga | 420 |
| cctgcacttc atttgggggcc cacatacacc aaaaaaatgc tgcataattc tcggggcagc | 480 |
| aagtcggtta cccggccgcc gtgctggacc gggttgaatg gtgcccgtaa ctttcggtag | 540 |
| agcggacggc caatactcaa cttcaaggaa tctcacccat gcgcgccggc ggggaaccgg | 600 |
| agttcccttc agtgaacgtt attagttcgc cgctcggtgt gtcgtagata ctagcccctg | 660 |
| gggcctttg aaatttgaat aagatttatg taatcagtct tttaggtttg accggttctg | 720 |
| ccgctttttt taaaattgga tttgtaataa taaaacgcaa ttgtttgtta ttgtggcgct | 780 |
| ctatcataga tgtcgctata aacctattca gcacaatata ttgttttcat tttaatattg | 840 |
| tacatataag tagtagggta caatcagtaa attgaacgga gaatattatt cataaaaata | 900 |
| cgatagtaac gggtgatata ttcattagaa tgaaccgaaa ccggcggtaa ggatctgagc | 960 |
| tacacatgct caggtttttt acaacgtgca caacagaatt gaaagcaaat atcatgcgat | 1020 |
| cataggcgtc tcgcatatct cattaaagag ctcgagcttg tcgatcgact ctagctagag | 1080 |
| gatcgatccg aacccagag tcccgctcag aagaactcgt caagaaggcg atagaaggcg | 1140 |
| atgcgctgcg aatcgggagc ggcgataccg taaagcacga ggaagcggtc agcccattcg | 1200 |
| ccgccaagct cttcagcaat atcacgggta gccaacgcta tgtcctgata gcggtccgcc | 1260 |
| acacccagcc ggccacagtc gatgaatcca gaaaagcggc cattttccac catgatattc | 1320 |
| ggcaagcagg catcgccatg tgtcacgacg agatcctcgc cgtcgggcat gcgcgccttg | 1380 |
| agcctggcga acagttcggc tggcgcgagc ccctgatgct cttcgtccag atcatcctga | 1440 |
| tcgacaagac cggcttccat ccgagtacgt gctcgctcga tgcgatgttt cgcttggtgg | 1500 |
| tcgaatgggc aggtagccgg atcaagcgta tgcagccgcc gcattgcatc agccatgatg | 1560 |
| gatactttct cggcaggagc aaggtgagat gacaggagat cctgccccgg cacttcgccc | 1620 |
| aatagcagcc agtcccttcc cgcttcagtg acaacgtcga gcacagctgc gcaaggaacg | 1680 |
| cccgtcgtgg ccagccacga tagccgcgct gcctcgtcct ggagttcatt cagggcaccg | 1740 |
| gacaggtcgg tcttgacaaa aagaaccggg cgcccctgcg ctgacagccg gaacacggcg | 1800 |
| gcatcagagc agccgattgt ctgttgtgcc cagtcatagc cgaatagcct ctccacccaa | 1860 |
| gcggccggag aacctgcgtg caatccatct tgttcaatcc ccataccacc tcttaagcgg | 1920 |
| agcaccaaat ggagggtaga ctccttctgg atgttgtagt cggcaagagt acgaccatcc | 1980 |
| tcaagctgct ttccggcgaa aatcaaacgc tgctggtctg ggggaatccc ttccttgtcc | 2040 |
| tggatcttgg ctttgacatt gtcgatggtg tcggaagact caacctctag ggtgatcgtc | 2100 |
| ttccccgtta gggtcttcac gaagatctgc atctgcaaag tcataaaaac aacawtcaga | 2160 |

```
acaacggaaa aaaactcaaa ttatagggct tttcacactc cctgattaac tgattcgaga    2220
attaaaacca aacaatctaa aacacgggga aaaaactcaa attttagggc tttttcatca    2280
aaacaaccgg aaaacctcaa attttagggc tttagaatca aaccgacgaa aaatcacaaa    2340
ttctagggct ttttcatcaa atcaaccgga aaaaaaaat caaattcaag accttttca     2400 tcaaaccacc ataaaaaaac tcaaattcta gggcattatc atcaaatcac ccggaaaacc    2460
ccacattttg ggcctttaga atcaaaccga cgaaaaaact ctaattttaa accttttggca   2520 tcaaatcgac ggaaaaaaac tcaaattagg ggcttttttca tcaaaacaac ggaaaaaaaa   2580
ctcaaatttt agggctttaa cagcacctgc ttagctaatt cgagaatcta aacagacaaa   2640
aaccaaaaaa tagagaagat ttctaaccct gaaagagaaa tttaaaggca attgagagaa   2700
attataatag aagtcagata gaagatgaaa aaatgaggtg cagaaaggtt ccttttatag   2760
atggcatggc cgactctaga cgaaaccgcc tcatagggtt agccaattat atgatgacac   2820
gtgtaataat gaggtgtagt gtagcaaaac aacacgcaaa agctaccgtt tcttttatt    2880 tatgtggtgg ggaaaattag gagaatgagg ttgacgctta cacgctcctt tagaaaaaac   2940 tagaaaatg taggtcatag taaaaaaata tactaaaaat aacttaattt tattttaggt    3000
attggccaaa atctggggaa aaaatttggt ctgaatttaa ttagaatgat attttattta    3060
tgttatttta tttttaaaa tatttttatt cttttaactt taatacattt taactaaaaa    3120
ataaagaata tatcaattta ttttaaaata aaaaaatatt ataattttct taattttcta   3180
tctaattttt ttgatcattt agcattttct tttttattaa ttaatatatg ctctaatata   3240
gcgcttttta agtatattgt gaacataacc ttaaatataa gagtttaaat attagcaaat   3300
tagggtataa tactcgttga taatcgcact ttaatctttt ttcttatatt atgtattgct   3360 ccttttttttt acattatttt tttattgtta ttgacctcat attgataagt atttgttatc   3420
taaatttgat tgaaaatatt ttattaat tgagtatata ttagaaacac ttttctttt     3480 ttatataaga ggtaagtatc aagcttgcat gcctgcagga gatgctggaa attgtgatca   3540
actacatgca aaatgtcttt tcgcctaacc acttaccata tttgatattt tccttttgcc   3600
aaattacaca aaccctatct tgtctctcac atatatatcc aattaataca cccctgccac   3660
ttgttaattc tcgaccatgt atgtatactt atgtaaagaa tatccaaaag ctttcttttt   3720
gttccttcga ttttaagcaa cttgtgttct catttctcaa tatcttaaag aaatcctgag   3780
taaaaaagtt tatagcctcc gtgaatctta ggaaattact ctagcatatt caatttttt    3840 gaaacaatat ataaatttt ctgaataatt aaatttacat atctatgcta cgaaacttga    3900
ttaattaaat caaatatata tatatatata taataataat aataataata taacatttt    3960 tttaggacac aaatatctaa tctcactata ctctagaagt atttgcaatg cacgatatgt   4020
gaatggagaa aagacagaaa gagcatttga aaatatctcg tttcacggat cattatgtct   4080
aattatttta ccatagaaaa gcgacaatta taaacaattt gttattcgtg aaaaataat    4140 atttaataat ggttgtcgta ccctataaac tacagccaca cattcataca ataagaagtt   4200
aaaaaaattc atacccctaaa ggcatcaacc agtgaagggt cagaaacttc ccaagatggg   4260
tcaaaggaca catgtcagat tctcagtgat tgacagcctt gataattaca aaaccgtggg   4320
atcgcttagc tgtttcttat ccacgtggca ttcacagaga cagaaactcc gcgttcgacc   4380 ccacaaaatat ccaaatatct tccggccaat ataaacagca agctctcact ccaacatttc   4440
tataacttca aacacttacc tgaattagaa aagaaagata gatagagaaa taaatatttt   4500
```

```
atcataccat acaaaaaaag acagagatct tctacttact ctactctcat aaaccttatc    4560
cagtttcttg aaacagagta ctcttctgat caatggagga atgtgaggca atgctaaaag    4620
cgaaaaaggc agcctacctt agcgatgagg agctgattga actttcactc tctggcaaac    4680
ttcctggata tgctctggag aagtcattgg aaaatgagga acttatgagc cgtgttgatg    4740
ccttcacccg ggcagtcaaa atccgcaggg ctgtagtatc gaggaccccc gcaacttctg    4800
caatcaccag ctctttggaa acttctaagc tgccctataa ggattacaat tatgcgcttg    4860
tccatggtgc ttgctgtgag aacgttattg gcaccctgcc tctgcctctt ggagttgccg    4920
gtccccttgt tattgatggt caaagctatt tcattcccat ggcaacaact gaaggtgttt    4980
tggtagccag tgccagtcga ggcgccaagg ctattaacgc tggtggtggt gcagtgactg    5040
tcttaactgg cgatggcatg actcgcggtc cctgtgtcgg gtttcctaca cttgcacgcg    5100
cagctgcagc taaggtctgg ctcgactccg aggagggtaa gagcgtcatg acagcagcat    5160
tcaactctac cagccggttt gctcgactgc agcacctgaa gactgccctt gccggtacct    5220
acttgtatat ccggttcaag acgactactg gcgatgccat gggtatgaac atgatttcga    5280
aaggcgttga gaaagcactc catgtcatgg ctacagagtg tagattcgac gacatggcca    5340
ccatctctgt gtctggcaac ttttgtaccg acaagaaagc agctgctctc aactggattg    5400
acggccgcgg caaatcagtt gtggctgagg ctattatccc cggtgatgtt gtgcgcaatg    5460
tgctaaagag tggtgttgat gcattggtgg aattgaacac tagcaagaat ctgattggca    5520
gtgcaatggc aggtagcttg ggcggattca acgctcacgc atcaaacatt gttactgcaa    5580
tctttctcgc aactggtcaa gaccccgcgc aaaatgtgga gagcagcagc tgcattacca    5640
cgatgaagaa tacaaatggc aatcttcaga tcgctgtgtc tatgccttca attgaggttg    5700
gcactatcgg tggtggtact atcctcgaag cgcagggtgc tatgcttgac ttactaggcg    5760
tccgtggctc tcaccccacc aaccccggcg ataacgcgcg tcagctggct cgtattgtgg    5820
cagccgcagt gcttgctggc gaactgagtc tatgctctgc gcttgcggct ggacatcttg    5880
tcagagcgca catggcccac aaccgcagtg ccgctcccac tcggtcagcg accccggtct    5940
cagcggctgt tggtgctacg cggggactgt ccatgacgtc ttcaagatct aggggagcct    6000
gccagctgtt gaattttgac cttcttaagc tggcgggaga cgtcgagtcc aaccctgggc    6060
ccatggcgca gctttcagtt gaacagtttc tcaacgagca aaaacaggcg gtggaaacag    6120
cgctctcccg ttatatagag cgcttagaag ggccggcgaa gctgaaaaag gcgatggcgt    6180
actcattgga ggccggcggc aaacgaatcc gtccgttgct gcttctgtcc accgttcggg    6240
cgctcggcaa agacccggcg gtcggattgc ccgtcgcctg cgcgattgaa atgatccata    6300
cgtactcttt gatccatgat gatttgccga gcatggacaa cgatgatttg cggcgcggca    6360
agccgacgaa ccataaagtg ttcggcgagg cgatggccat cttggcgggg gacgggttgt    6420
tgacgtacgc gtttcaattg atcaccgaaa tcgacgatga gcgcatccct ccttccgtcc    6480
ggcttcggct catcgaacgg ctggcgaaag cggccggtcc ggaagggatg gtcgccggtc    6540
aggcagccga tatggaagga gaggggaaaa cgctgacgct ttcggagctc gaatacattc    6600
atcggcataa aaccgggaaa atgctgcaat acagcgtgca cgccggcgcc ttgatcggcg    6660
gcgctgatgc ccggcaaacg cgggagcttg acgaattcgc cgcccatcta ggccttgcct    6720
ttcaaattcg cgatgatatt ctcgatattg aaggggcaga agaaaaaatc ggcaagccgg    6780
tcggcagcga ccaaagcaac aacaaagcga cgtatccagc gttgctgtcg cttgccggcg    6840
cgaaggaaaa gttggcgttc catatcgagg cggcgcagcg ccatttacgg aacgccgacg    6900
```

```
ttgacggcgc cgcgctcgcc tatatttgcg aactggtcgc cgcccgcgac cattctagcc    6960
accaccacca ccaccacgtg tgaattacag gtgaccgagc tcgaatttcc ccgatcgttc    7020
aaacatttgg caataaagtt tcttataaga ttgaatcctg ttgccggtct tgcgatgatt    7080
atcatataat ttctgttgaa ttacgttaag catgtaataa ttaacatgta atgcatgacg    7140
ttatttatga gatgggtttt tatgattaga gtcccgcaat tatacattta atacgcgata    7200
gaaaacaaaa tatagcgcgc aaactaggat aaattatcgc gcgcggtgtc atctatgtta    7260
ctagatcggg gaattcgtaa tcatgtcata gctgtttcct gtgtgaaatt gttatccgct    7320
cacaattcca cacaacatac gagccggaag cataaagtgt aaagcctggg gtgcctaatg    7380
agtgagctaa ctcacattaa ttgcgttgcg ctcactgccc gctttccagt cgggaaacct    7440
gtcgtgccag ctgcattaat gaatcggcca acgcgcgggg aaaaggcggt ttgcgtattg    7500
gagcttgagc ttggatcaga ttgtcgtttc ccgccttcag tttaaactat cagtgtttga    7560
caggatatat tggcgggtaa acctaagaga aaagagcgtt tattagaata atcggatatt    7620
taaaagggcg tgaaaaggtt tatccgttcg tccatttgta tgtgcatgcc aaccacaggg    7680
ttcccctcgg gatcaaagta ct                                            7702
```

TRANSGENIC GUAYULE FOR ENHANCED ISOPRENOID PRODUCTION

REFERENCE TO RELATED APPLICATIONS

This application claims priority to U.S. Provisional Patent Application Ser. No. 61/724,244, filed Nov. 8, 2012, which is incorporated herein by reference in its entirety.

FIELD OF THE INVENTION

The invention relates to transgenic guayule plants (*Parthenium argentatum* Gray) and uses thereof.

BACKGROUND OF THE INVENTION

Natural rubber, cis-1,4 polyisoprene, a biobased elastomer, is produced primarily in tropical climates by the Brazilian rubber tree, *Hevea brasiliensis* (*Hevea*). Natural rubber is essential in many industrial applications and in many of its most significant applications, natural rubber cannot be replaced by synthetic alternatives. Because of its desirable properties and heavy demand, the price of natural rubber is rising, making natural rubber increasingly more precious as an industrial material. Indeed, in 2011, 10 million MT of natural rubber (NR) valued over $10B USD was harvested for use in commerce.

Unfortunately, users of natural rubber not only face rising prices, but also the potential for shortage. Indeed, the demand for *Hevea* rubber is expected to exceed supply by 25% by 2020.

Natural rubber is unique in that for many applications it has no synthetic equivalent. Indeed, its unique properties of resilience, elasticity, abrasion- and impact-resistance, efficient heat dispersion, and malleability at cold temperatures are unmatched by synthetic alternatives (see e.g., Cornish (2001) Phytochemistry 57, 1123-1134). For example airplanes cannot safely land with tires made from synthetic rubber; and only truck tires made from natural rubber are resilient enough to withstand heavy shear and loads. Thus, potential shortages of natural rubber foretell profound consequences for commerce.

Unfortunately, today, *Hevea brasiliensis* is essentially the sole commercial source of natural rubber. But, fortunately, there are alternative plant sources for natural rubber. Chief among the alternatives is guayule (*Parthenium argentatum* Gray). *Parthenium argentatum* Gray commonly known as guayule, is a shrub in the family Asteraceae, native to the southwestern United States and northern Mexico.

On its own, guayule is presently not economical without either greater rubber yields or identification and development of high value coproducts. However, if developed, guayule has great potential as a new or alternative crop for arid and semiarid areas of the southwestern United States, north central Mexico, and regions with similar climates around the world (see e.g., Thompson and Ray 1989; Wright et al. (1991) Guayule economics, p. 351-366. In: J. W. Whitworth and E. E. Whitehead (eds.). Guayule natural rubber. Office of Arid Lands, Univ. of Arizona, Tucson). Thus, development of guayule cultivars capable of producing high yields of natural rubber latex would be invaluable for increasing the quantities of natural latex rubber.

Therefore, what is needed in the art, are methods for improving the quantity and/or quality of natural rubber from guayule, and new guayule cultivars capable of producing high yields of natural rubber latex.

Fortunately, as will be clear from the following disclosure, the present invention provides for these and other needs.

SUMMARY OF THE INVENTION

In one embodiment, the invention provides a transgenic guayule plant which produces increased amounts of rubber wherein the transgenic guayule plant has a dwarf phenotype under field grown conditions, and wherein the transgenic guayule plant comprises a heterologous 3-hydroxy-3-methylglutaryl-coenzyme A reductase (HMGR) nucleic acid operably linked to a promoter nucleic acid, and the transgenic guayule plant expresses the heterologous HMGR nucleic acid. In one exemplary embodiment, the heterologous 3-hydroxy-3-methylglutaryl-coenzyme A reductase (HMGR) nucleic acid operably linked to a promoter nucleic acid is a truncated HMGR gene having genbank accession number AF479817 which encodes a 465 amino acid segment that functions as a catalytic domain.

In another embodiment, the invention provides a transgenic guayule plant which produces increased amounts of rubber wherein the wherein the transgenic guayule plant shows increased regrowth in the field, and wherein the transgenic guayule plant comprises a heterologous 3-hydroxy-3-methylglutaryl-coenzyme A reductase (HMGR) nucleic acid operably linked to a promoter nucleic acid, and the transgenic guayule plant expresses the heterologous HMGR nucleic acid. In one exemplary embodiment, the heterologous 3-hydroxy-3-methylglutaryl-coenzyme A reductase (HMGR) nucleic acid operably linked to a promoter nucleic acid is a truncated HMGR gene having genbank accession number AF479817 which encodes a 465 amino acid segment that functions as a catalytic domain.

In another embodiment, the invention provides a transgenic guayule plant which produces increased amounts of rubber wherein the transgenic guayule plant comprises a heterologous 3-hydroxy-3-methylglutaryl-coenzyme A reductase (HMGR) nucleic acid and a farnesyl pyrophosphate synthase nucleic acid (FPS nucleic acid) operably linked to a cold inducible promoter nucleic acid, and the transgenic guayule plant expresses the heterologous HMGR nucleic acid and the FPS nucleic acid in response to exposure to cold treatment. In one exemplary embodiment the cold inducible promoter is a member selected from the group consisting of cor15a; Cor39; WRKY71; wcs120; RCI2A; RCI2B and CBF2. In another exemplary embodiment, the cold inducible promoter is CBF2. In another exemplary embodiment, the transgenic guayule plant does not exhibit an increase in resin content. In another exemplary embodiment, the amount of rubber is increased at least about 2.5 fold by comparison to an otherwise isogenic guayule plant that does not expresses a heterologous HMGR nucleic acid and an FPS nucleic acid in response to exposure to cold treatment.

In another embodiment, the invention provides a method for producing an increased amount of rubber in a transgenic guayule plant by comparison to the amount of rubber produced by an otherwise isogenic non-transgenic guayule plant without increasing the resin content, the method comprising: (a) transforming a plant cell of a guayule plant with an expression vector comprising a heterologous 3-hydroxy-3-methylglutaryl-coenzyme A reductase (HMGR) nucleic acid and a farnesyl pyrophosphate synthase nucleic acid (FPS nucleic acid) operably linked to a cold inducible promoter nucleic acid to provide a transformed plant cell; (b) regenerating the transformed plant cell to provide a transgenic guayule plant capable of expressing the heterologous 3-hydroxy-3-methylglutaryl-coenzyme A reductase (HMGR) nucleic acid in response to cold stimulus; and (c) expressing the heterologous 3-hydroxy-3-methylglutaryl-coenzyme A reductase (HMGR) nucleic acid the transgenic guayule plant, thereby, producing an increased amount of rubber in a transgenic guayule plant by comparison to the amount of rubber produced by an otherwise isogenic non-transgenic guayule plant without also increasing the resin content.

Other features, objects and advantages of the invention will be apparent from the detailed description which follows.

BRIEF DESCRIPTION OF THE DRAWINGS

FIG. 1A and 1B. SEQ ID NO:1 Complete coding sequence of the 3-hydroxy-3-methylglutaryl-coenzyme A reductase (HMGR) gene from *Aspergillus nidulans*.

FIG. 2. SEQ ID NO:2 465 amino acid catalytic domain encoded by nucleotide 2863-4315 of SEQ ID NO:1. The intron at nucleotides 3921-3976 is spliced out and not translated as part of the catalytic domain.

FIG. 5A. Average height (cm) of guayule field plants, by line, transplanted as seedlings to Field 110 at the University of Arizona Maricopa Agricultural Center in late March/early April 2007. Plant dimensions measured from May 2007 to January 2009. VC=Vector Control, TCC=tissue culture control. FIG. 5B. Plant growth rate, expressed as average change in plant height (cm) by line over a one month period, for guayule field plants, by line, transplanted as seedlings to Field 110 at the University of Arizona Maricopa Agricultural Center in late March/early April 2007. Plant dimensions measured from May 2007 to January 2009. VC=Vector Control, TCC=tissue culture control.

FIG. 10A and FIGS. 10B, 10C, and 10D. FIG. 10A: Schematic view of pND9 T-DNA construct (empty vector control); FIGS. 10B, 10C, and 10D: (SEQ ID NO:11) full pND9 T-DNA sequence (empty vector control) 7413 bp sequence.

7413 bp. This T-DNA is in binary vector pPZP200 (6153 bp).

Figure 11A:
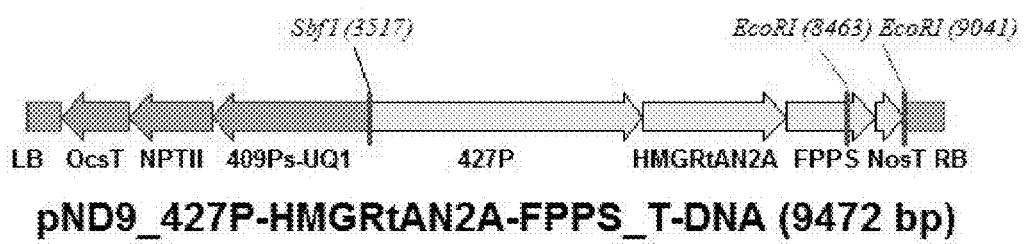

1-333: Left Board
334-1047: Ocs Terminator
1107-1904: NPTII gene
1905-2132: UQ1
2133-3500: 409 Promoter Short
3501-4441: CaMV 2×35S Promoter
4442-4669: UQ1
4670-6694: GUSplus gene from CAMBIA
6714-6987: Nos Terminator
7213-7413: Right Board FIG. 11A and FIGS. 11B, 11C, and 11D. FIG. 11A: Schematic view of pND9_427P-HMGRtAN2A-FPPs_T-DNA construct (designed for overexpression of both HMGR and FPPs by a single constitutive promoter); FIGS. 11B, 11C, and 11D: (SEQ ID NO:12) pND9_427P-HMGRtAN2A-FPPs_T-DNA sequence (designed for overexpression of both HMGR and FPPs by a single constitutive promoter)

This T-DNA is in binary vector pPZP200 backbone.

Figure 12A:
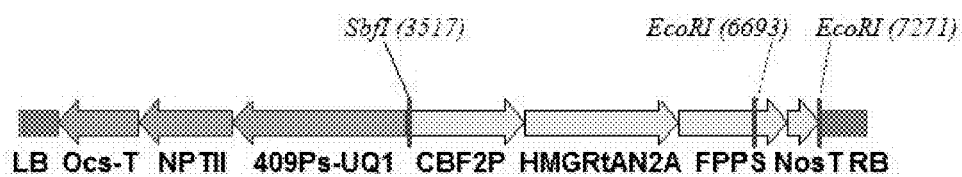

1-333: Left Board
334-1047: Ocs Terminator
1107-1904: NPTII gene
1905-2132: UQ1
2133-3500: 409 Promoter Short
3501-6362: 427 Promoter
6363-7760: HMGR gene from *Aspergillus nidulans*, truncated
7761-7832: 2A Link peptide gene from foot-mouth disease virus
7833-8753: FPPS gene from *B. stearothermophilus*
8773-9046: Nos Terminator
9272-9472: Right Board FIG. 12A and FIGS. 12B, 12C, and 12D. FIG. 12A: Schematic view of pND9_CBF2P-HMGRtAN2A-FPPs_T-DNA construct (designed for overexpression of both HMGR and FPPs by a single cold-inducible promoter); FIGS. 12B, 12C, and 12D: (SEQ ID NO:13) pND9_CBF2P-HMGRtAN2A-FPPs_T-DNA sequence (designed for overexpression of both HMGR and FPPs by a single cold-inducible promoter)

This T-DNA is in binary vector pPZP200 backbone.

1-333: Left Board
334-1047: Ocs Terminator
1107-1904: NPTII gene
1905-2132: UQ1
2133-3500: 409 Promoter Short
3501-4592: CBF2 Promoter
4593-5990: HMGR gene from *Aspergillus nidulans*, truncated
5991-6062: 2A Link peptide gene from foot-mouth disease virus 6063-6983: FPPS gene from *B. stearothermophilus*
7003-7276: Nos Terminator
7502-7702: Right Board

DETAILED DESCRIPTION OF THE INVENTION

Definitions

The term "plant" as used herein refers to whole plants, plant bodies, plant organs (e.g., leaves, stems, flowers, roots, etc.), seeds, plant tissues, plant cells and progeny of same. In an exemplary embodiment, a plant cell includes callus. In another exemplary embodiment, a plant organ includes a root, a leaf, a flower and/or the like. The term "plant" refers to the broad class of higher plants amenable to transformation techniques, (might as well claim monocot crop plants too, in case promoter works there). The term "plant" also includes plants of any variety of ploidy levels, including polyploid, diploid, haploid and hemizygous.

Some exemplary plants include, but are not limited, to guayule (*Parthenium argentatum* Gray), alfalfa (*Medicago saliva*), sunflower (*Helianthus annus*), soybean (*Glycine max*), tobacco (*Nicotiana tabacum*), potato (*Solanum tuberosum*), and laboratory plants, e.g., *Arabidopsis*, etc.

The term "transgenic plant" as used herein refers to a plant comprising at least one heterologous nucleic acid sequence that was introduced into the plant, at some point in its lineage, by genetic engineering techniques. In an exemplary embodiment, a transgenic plant is a guayule plant that is transformed with an expression vector comprising a heterologous 3-hydroxy-3-methylglutaryl-coenzyme A reductase (HMGR) nucleic acid. In another exemplary embodiment, a transgenic plant is a plant that is the progeny or decendant of a plant that is transformed with an expression vector comprising a heterologous HMGR nucleic acid and which comprises the expression vector comprising heterologous HMGR nucleic acid. Thus, the term "transgenic plant" refers to plants which are the direct result of transformation with a heterologous nucleic acid or transgene, and the progeny and decendants of transformed plants which comprise the introduced heterologous nucleic acid or transgene.

The expression "expresses the heterologous HMGR nucleic acid" as used herein, refers to transcription of the heterologous HMGR nucleic acid. In an exemplary embodiment, "expression of the heterologous HMGR nucleic acid" is detected by real time PCR.

The expression "produces increased amounts of rubber" as used herein refers to the rubber content produced by one guayule plant by comparison to the rubber content produced by a control guayule plant. In one exemplary embodiment, an "increased amount of rubber" is produced by a guayule plant which expresses a heterologous HMGR nucleic acid by comparison to an otherwise isogenic guayule plant which does not express a heterologous HMGR nucleic acid. In other exemplary embodiments, an "increased amount of rubber" is produced by a guayule plant which expresses a heterologous HMGR nucleic acid and a farnesyl pyrophosphate nucleic acid under control of a cold inducible promoter, by comparison to an otherwise isogenic guayule plant which does not express a heterologous a heterologous HMGR nucleic acid and a farnesyl pyrophosphate nucleic acid under control of a cold inducible promoter. Rubber content can be measured as disclosed herein below in Example 1, or by any other method known in the art (see e.g., Jasso de Rodriguez et al. (1993) J. Am. Oil Chem. Soc. 70:1229-1234). Typically "increased amounts of rubber" are at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, or more.

The expression "cold treatment" or "exposure to cold" as used herein refers to induction of a cold inducible promoter by exposure to cold temperatures or cold shock. Typically cold temperatures are less than about 20° C. In general "cold treatment" varies with the promoter used. Induction of a cold inducible promoter by exposure to cold temperatures or cold shock is well known in the art see e.g., Ouellet, F., et al. FEBS Letters 423 (1998) 324-328; Kyonoshin Maruyama et al. DNA Res. 2012 February; 19(1): 37-49; Fang, L. et al. (1997) Molecular Microbiology Volume 23, Issue 2, pages 355-364.

The expression "has a dwarf phenotype under field grown conditions" as used herein refers to measured plant dimensions during field cultivation, and measured biomass at harvest, which are statistically significantly lower than corresponding control plants. In exemplary embodiments, a "dwarf phenotype under field grown conditions" refers to a transgenic guayule plant expressing a heterologous HMGR nucleic acid the biomass of which is at least about 35% lower than an otherwise isogenic control plant which does not express a heterologous HMGR nucleic acid and which has a height which is at least about 9% shorter than an otherwise isogenic control plant which does not express a heterologous HMGR nucleic acid. In one exemplary embodiment, a transgenic guayule plant that expresses a heterologous HMGR nucleic acid having a "dwarf phenotype under field grown conditions" is about 23% lower in height and has a biomass that is about 43% lower than an otherwise isogenic control plant which does not express a heterologous HMGR nucleic acid.

The expression "increased regrowth in the field" as used herein refers to the survival rate following harvest by pollarding. As is known in the art, guayule is typically harvested by pollarding. Typically, after a single pollarding, less than 100% of the plants survive and regenerate new growth. Plants pollarded for two consecutive years have an even lower survival rate than plants pollarded the first year (see e.g., D. T. Ray et al. (1992) Industrial Crops and Products 1:11-15). Accordingly, in an exemplary embodiment, increased regrowth in the field is measured by comparing the survival rate after pollarding of transgenic guayule plants comprising a heterologous HMGR nucleic acid which is expressed in the transgenic guayule plant, to the survival rate after pollarding of otherwise isogenic guayule plants which do not express a heterologous HMGR nucleic acid.

The expression "insect resistant plant" or "insect resistant guayule plant" as used herein refers to a guayule plant having qualities such that the plant experiences relatively less damage when exposed to a given insect pest(s) than a guayule plant without the qualities. Thus, in an exemplary embodiment, an "insect resistant guayule plant" is a transgenic guayule plant comprising a heterologous transgene that is less susceptible to insect damage than an otherwise isogenic transgenic guayule plant which does not comprise the heterologous transgene. Thus, insect resistance is relative and is based on comparison with plants lacking the resistance characters. Plant resistance to insects can be measured by any methods known in the art see e.g., *Plant resistance to insects. A fundamental approach.* Smith, C. M.

Author Department of Entomology, Louisiana State University, Baton Rouge, La., USA; *Biological and Biotechnological Control of Insect Pests*, Jack E. Rechcigl, Nancy A. Rechcigl CRC Press, Sep. 24, 1999. Exemplary insect pests of guayule include, but are not limited to *Lygus Hesperus*, scale, grasshoppers, etc.

Thus, in an exemplary embodiment, a transgenic guayule plant that is not insect resistant, is a transgenic guayule plant comprising a heterologous transgene that is equally susceptible to insect damage as an otherwise isogenic transgenic guayule plant which does not comprise the heterologous transgene.

The terms "isolated," "purified," or "biologically pure" as used herein, refer to material that is substantially or essentially free from components that normally accompany it as found in its native state. In an exemplary embodiment, purity and homogeneity are determined using analytical chemistry techniques such as polyacrylamide gel electrophoresis or high performance liquid chromatography. A nucleic acid that is the predominant species present in a preparation is substantially purified. In one exemplary embodiment, an isolated HMGR nucleic acid is separated from open reading frames and/or other nucleic acid sequences that flank the HMGR nucleic acid in its native state. In an exemplary embodiment, the term "purified" denotes that a nucleic acid or protein gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "polypeptide," "peptide" and "protein" are used interchangeably herein to refer to a polymer of amino acid residues. The terms apply to naturally occurring amino acid polymers and non-naturally occurring amino acid polymers as well as amino acid polymers in which one or more amino acid residues is an artificial chemical mimetic of a corresponding naturally occurring amino acid.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids are referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art (see, e.g., Creighton, Proteins (1984)). Such conservatively modified variants are in addition to and do not exclude polymorphic variants, interspecies homologs, and alleles.

The following eight groups illustrate some exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);

6) Phenylalanine (F), Tyrosine (Y), Tryptophan (W);
7) Serine (S), Threonine (T); and
8) Cysteine (C), Methionine (M)

Macromolecular structures such as polypeptide structures are described in terms of various levels of organization. For a general discussion of this organization, see, e.g., Alberts et al., Molecular Biology of the Cell ($3^{rd}$ ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "label" as used herein, refers to a composition detectable by spectroscopic, photochemical, biochemical, immunochemical, or chemical means. Exemplary labels include $^{32}$P, fluorescent dyes, electron-dense reagents, enzymes (e.g., as commonly used in an ELISA), biotin, digoxigenin, or haptens and proteins for which antisera or monoclonal antibodies are available.

As used herein a "nucleic acid probe or oligonucleotide" refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (e.g., 7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. In one exemplary embodiment, probes are directly labeled as with isotopes, chromophores, lumiphores, chromogens etc. In other exemplary embodiments probes are indirectly labeled e.g., with biotin to which a streptavidin complex may later bind. By assaying for the presence or absence of the probe, one can detect the presence or absence of the select sequence or subsequence.

Thus, the term "labeled nucleic acid probe or oligonucleotide" as used herein refers to a probe that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "primer" as used herein, refers to short nucleic acids, typically DNA oligonucleotides of at least about 15 nucleotides in length. In an exemplary embodiment, primers are annealed to a complementary target DNA strand by nucleic acid hybridization to form a hybrid between the primer and the target DNA strand. Annealed primers are then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

PCR primer pairs are typically derived from a known sequence, for example, by using computer programs intended for that purpose such as Primer (Version 0.5 ©1991, Whitehead Institute for Biomedical Research, Cambridge, Mass.). One of skill in the art will appreciate that the specificity of a particular probe or primer increases with its length. Thus, for example, a primer comprising 20 consecutive nucleotides of an HMGR nucleic acid will anneal to a related target sequence with a higher specificity than a corresponding primer of only 15 nucleotides. Thus, in an exemplary embodiment, greater specificity of a nucleic acid primer or probe, is attained with probes and primers selected to comprise 20, 25, 30, 35, 40, 50 or more consecutive nucleotides of a selected sequence.

Nucleic acid probes and primers are readily prepared based on the nucleic acid sequences disclosed herein. Methods for preparing and using probes and primers and for labeling and guidance in the choice of labels appropriate for various purposes are discussed, e.g., in Sambrook et al., Molecular Cloning, A Laboratory Manual 2nd ed. 1989, Cold Spring Harbor Laboratory; and Current Protocols in Molecular Biology, Ausubel et al., eds., 1994, John Wiley & Sons). The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, over expressed, under expressed or not expressed at all.

The term "HMGR nucleic acid" or "HMGR sequence" or "HMGR nucleic acid sequence" or equivalent expressions as used herein, refer to isolated nucleic acid sequences which comprise a nucleotide sequence identical to or substantially identical to base pairs 3471-3920 of AF479817 SEQ ID NO:1 and FIG. 1A and FIG. 1B. In some exemplary embodiments an "HMGR nucleic acid" is a complete HMGR gene which in an exemplary embodiment comprises nucleotide 1-4315 of SEQ ID NO:1. Thus, in an exemplary embodiment, an HMGR nucleic acid is an HMGR gene. In some exemplary embodiments an HMGR nucleic acid comprises nucleotides 2863-4315 of SEQ ID NO:1 and encodes the catalytic domain of HMGR. In other exemplary embodiments, and HMGR nucleic acid comprises nucleotides 3471-4234 of SEQ ID NO:1 and thus encodes the minimal catalytic domain of HMGR. In still other exemplary embodiments, and HMGR nucleic acid comprises nucleotides 798-4315 of SEQ ID NO:1. Thus, in some exemplary embodiments an HMGR nucleic acid encodes the membrane spanning domain plus the catalytic domain.

In some exemplary embodiments, isolated HMGR sequences are derived from the HMGR gene of *Aspergillus nidulans*. However, isolated HMGR nucleic acids can be isolated from any source and/or can be synthetically made, by methods known on the art (see e.g., U.S. Pat. No. 5,942,609) as long as they are substantially identical to HMGR sequences as disclosed herein. Methods for determining nucleotide sequence identity and "substantial identity" are described below. However, in general, two nucleic acid sequences are considered to be substantially identical when the two molecules or their complements hybridize to each other under stringent hybridization conditions, as described below.

The term "capable of hybridizing under stringent hybridization conditions" as used herein, refers to annealing a first nucleic acid to a second nucleic acid under stringent hybridization conditions (defined below). In an exemplary embodiment, the first nucleic acid is a test sample, and the second nucleic acid is the sense or antisense strand of HMGR nucleic acid. Hybridization of the first and second nucleic acids is conducted under standard stringent conditions, e.g., high temperature and/or low salt content, which tend to disfavor hybridization of dissimilar nucleotide sequences.

The term "operably linked" refers to a functional linkage between a nucleic acid expression control sequence such as e.g., a promoter, or array of transcription factor binding sites, and a second nucleic acid sequence e.g., an HMGR nucleic acid, wherein the expression control sequence directs expression e.g., transcription, of the nucleic acid corresponding to the second sequence. In an exemplary embodiment, a promoter that is "operably linked" to a heterologous nucleic acid (e.g., an HMGR nucleic acid) is located upstream of and in-frame with the heterologous nucleic acid.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression cassette" as used herein, refers to a nucleic acid construct, typically generated recombinantly or synthetically, which comprises a series of specified nucleic acid elements that permit transcription of a particular nucleic acid in a host cell. In an exemplary embodiment, an expression cassette comprises a heterologous nucleic acid to be transcribed e.g., an HMGR nucleic acid, operably linked to a promoter.

Typically, an "expression cassette" is part of an "expression vector". The term "vector" as used herein, refers to nucleic acid capable of replicating in a selected host cell or organism. A vector can replicate as an autonomous structure, or alternatively can integrate into the host cell chromosomes and thus replicate along with the host cell genome. Thus, an "expression vector" is a nucleic acids capable of replicating in a selected host cell or organism e.g., a plasmid, virus, artificial chromosome, nucleic acid fragment, or any suitable construct known in the art, which comprises an "expression cassette".

The term "transformation" as used herein encompasses any and all techniques by which a nucleic acid molecule might be introduced into a cell, including but not limited to, transfection with viral vectors, transformation with plasmid vectors, and introduction of naked DNA by electroporation, lipofection, *Agrobacterium* infection, and particle gun acceleration.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length HMGR gene sequence or a nucleic acid sequence given in a sequence listing, or may comprise a complete HMGR sequence or gene sequence.

The terms "identical" or percent "identity," in the context of two or more nucleic acids or polypeptide sequences, refer to two or more sequences or subsequences that are the same or have a specified percentage of amino acid residues or nucleotides that are the same (e.g., 85% identity, 90% identity, 99%, or 100% identity), when compared and aligned for maximum correspondence over a comparison window, or designated region as measured using a sequence comparison algorithm or by manual alignment and visual inspection.

The phrase "substantially identical", in the context of two nucleic acids or polypeptides, refers to two or more sequences or subsequences that have at least about 85%, identity, at least about 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, the substantial identity exists over a region of the sequences that is at least about 50 residues in length. In another exemplary embodiment, the substantial identity exists over a region of the sequences that is at least about 100 residues in length. In still another exemplary embodiment, the substantial identity exists over a region of the sequences that is at least about 150 residues or more, in length. In one exemplary embodiment, the sequences are substantially identical over the entire length of nucleic acid or protein sequence.

For sequence comparison, typically one sequence acts as a reference sequence, to which test sequences are compared. Comparison can be by inspection or may be carried out with the aid of a computer sequence comparison algorithm. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An exemplary algorithm for sequence comparison is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387-395 (1984).

Another example of algorithm that is suitable for determining percent sequence identity and sequence similarity are the BLAST® and BLAST® 2.0 algorithms, which are described in Altschul et al., Nuc. Acids Res. 25:3389-3402 (1977) and Altschul et al., J. Mol. Biol. 215:403-410 (1990), respectively. Software for performing BLAST® analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST® algorithm parameters W, T, and X determine the sensitivity and speed of the alignment. The BLAST® program (for nucleotide sequences) uses as defaults a wordlength (W) of 11, an expectation (E) or 10, M=5, N4 and a comparison of both strands. For amino acid sequences, the BLAST® program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=4, and a comparison of both strands.

The BLAST® algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST® algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA). In general, two nucleic acid sequences are said to be "substantially identical" when the two molecules or their complements selectively or specifically hybridize to each other under stringent conditions.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences "specifically hybridize" at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. However, other high stringency hybridization conditions known in the art can be used.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

I. Introduction:

Natural rubber is unique and valuable material which, in many applications has no synthetic equivalent. Presently, natural rubber is produced primarily from the rubber tree *Hevea brasiliensis*. However, increased demand and diseases that affect *Hevea brasiliensis* require that alternative sources for natural rubber be developed.

Guayule, *Parthenium argentum* Gray, provides the needed alternative plant source for natural rubber. However, to become a truly viable source able to meet commercial demands, rubber yields from guayule must increase. Indeed, the primary objective of all of the breeding programs is to improve rubber yields per unit area. Breeders are also improving rubber quality and reducing postharvest rubber degradation, improving regrowth after clipping, processing quality of the shrub, and disease and insect resistance (see e.g., Thompson and Ray 1989; Estilai and Ray 1991).

Fortunately, as disclosed herein, the inventors have now discovered that transformation of guayule with an HMGR nucleic acid provided guayule plants having inter alia increased rubber content and increased regrowth in the field.

II. Isolating HMGR Nucleic Acids and Constructing Expression Vectors

A. General Recombinant DNA Methods

This invention utilizes routine techniques in the field of recombinant genetics. Basic texts disclosing the general methods of use in this invention include Sambrook et al., Molecular Cloning—A Laboratory Manual (2nd Ed.), Vol. 1-3, Cold Spring Harbor Laboratory, Cold Spring Harbor, N.Y., 1989; Kriegler, Gene Transfer and Expression: A Laboratory Manual (1990); and Current Protocols in Molecular Biology (Ausubel et al., eds., 1994)). Unless otherwise noted, technical terms are used according to conventional usage. Definitions of common terms in molecular biology maybe found in e.g., Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized e.g., according to the solid phase phosphoramidite triester method first described by Beaucage & Caruthers, Tetrahedron Letts. 22:1859-1862 (1981), using an automated synthesizer, as described in Van Devanter et al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

B. Methods for the Isolation of Nucleic Acids Comprising HMGR Sequences

Figure 8:
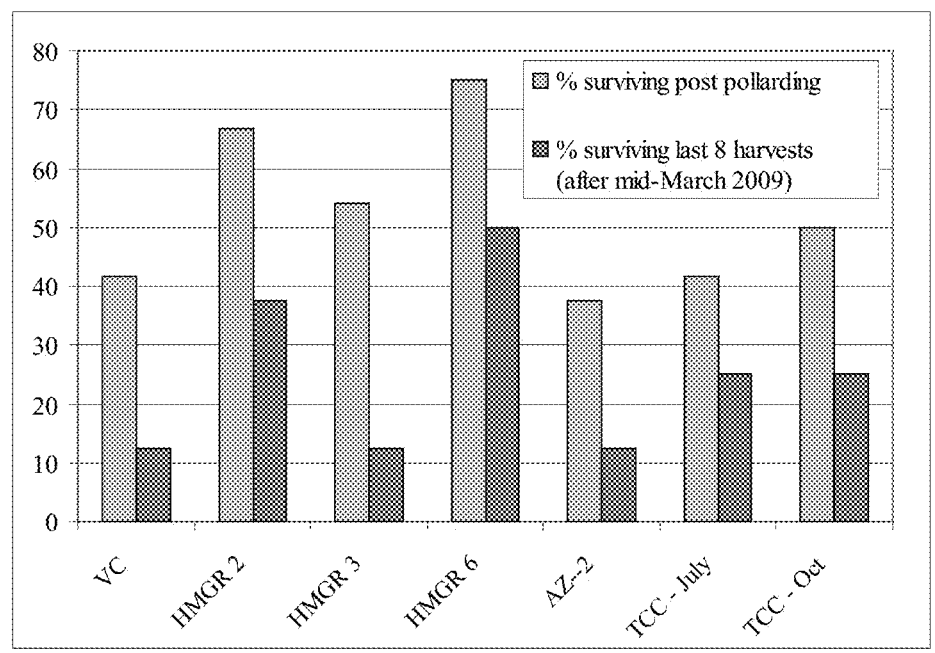
FIG. 8. Plant survival following pollarding harvest, expressed as percentage of guayule plants (by line) surviving post pollarding, measured Jun. 30, 2009, following a series of harvests of two-year old guayule plants from January 2009 to April 2009. VC=Vector Control, TCC=tissue culture control.
Figure 9A:
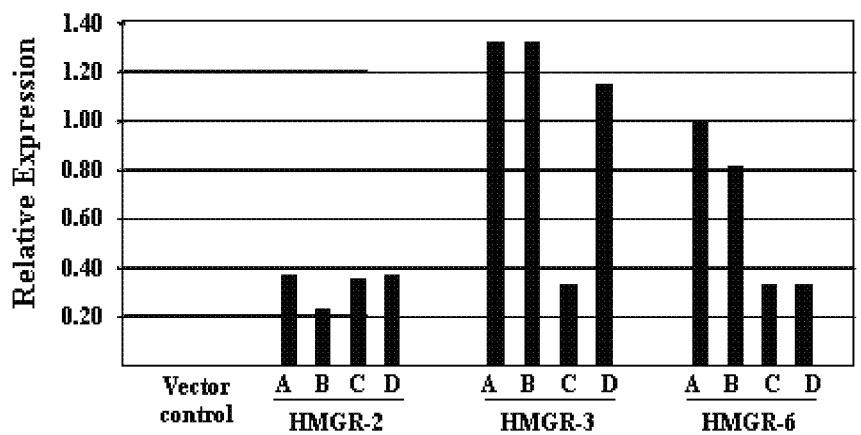
FIG. 9. HMGR transgene expression in guayule: Relative expression, as determined by real-time (qPCR) using the 2-ΔΔCt method in guayule plant tissues. 9a; whole plants from tissue culture 9b: bark parenchyma tissue harvested from ~2 year-old field plants shortly before harvest.
Figure 9B:
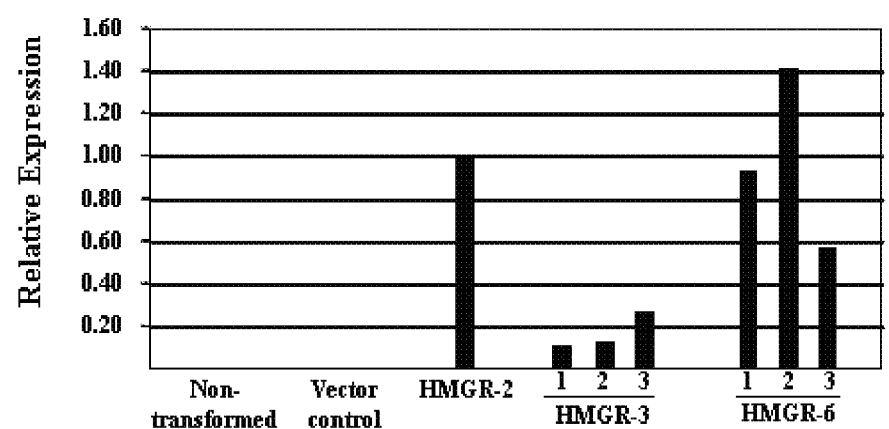
Figure 10A:
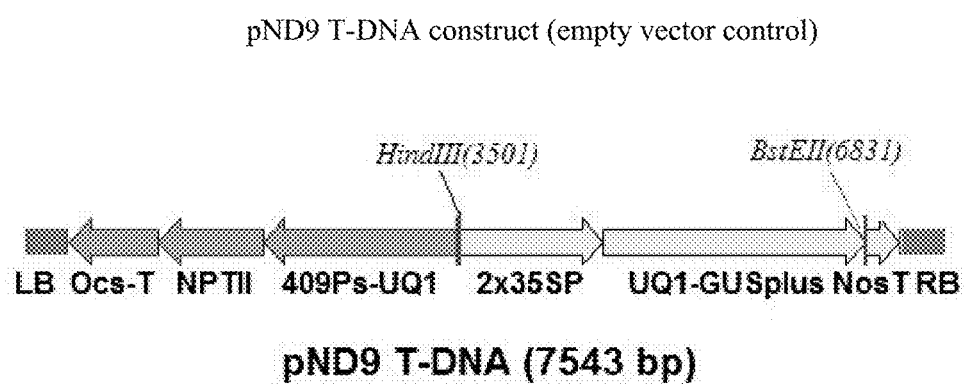

HMGR nucleic acids can be isolated using any of a variety of methods known to those of skill in the art which may be used for isolation of nucleic acids. For example, HMGR nucleic acids can be isolated from genomic DNA fragments encoding an HMGR gene e.g., an HMGR gene from *Aspergillus nidulans*. The term "HMGR gene" as used herein, refers to a plant genomic DNA molecule that comprises the entire HMGR gene. An exemplary "HMGR gene" is shown in FIG. 8. The term "HMGR nucleic acid" or "HMGR sequence" refers to a portion of the plant HMGR gene comprising the catalytic domain of HMGR. In an exemplary embodiment, an HMGR nucleic acid comprises nucleotides 798-4315 of SEQ ID NO:1. In another exemplary embodiment, an HMGR nucleic acid comprises nucleotides 798-4234). In another exemplary embodiment, an HMGR nucleic acid comprises nucleotides 2863-4315 of SEQ ID NO:1. In still another exemplary embodiment, an HMGR nucleic acid comprises nucleotides 3471-4234 of SEQ ID NO:1.

Genomic fragments encoding HMGR genes and HMGR nucleic acids can be prepared as disclosed below.

In an exemplary embodiment, the nucleic acid sequences comprising HMGR sequences are cloned from genomic DNA libraries using labeled oligonucleotide probes. In another exemplary embodiment, the nucleic acid sequences comprising HMGR sequences and related nucleic acid sequences are cloned from genomic DNA libraries using amplification techniques and labeled oligonucleotide primers.

HMGR nucleic acid sequences typically comprise sequences that are identical to, or show substantial sequence identity (as defined above) to nucleotides 3471-3920 of the *Aspergillus nidulans* HMGR gene depicted in SEQ ID NO:1. Thus, HMGR sequences typically hybridize to base pairs 3471-3920 of the nucleic acid sequence of SEQ ID NO:1 under stringent hybridization conditions.

To prepare a genomic library, typically DNA is extracted from plant tissue and either mechanically sheared or enzymatically digested to yield fragments of about 15-20 kb. The fragments are then separated by gradient centrifugation from undesired sizes and are constructed in bacteriophage lambda vectors. These vectors and phage are packaged in vitro, as described e.g., in Sambrook, et al. supra. Recombinant phage are analyzed by plaque hybridization as described in Benton and Davis, Science, 196:180-182 (1977). Colony hybridization is carried out as generally described in M. Grunstein et al. Proc. Natl. Acad. Sci. USA., 72:3961-3965 (1975). DNA encoding HMGR genes and/or HMGR sequence fragments or HMGR nucleic acidsis identified in genomic libraries by its ability to hybridize with labeled nucleic acid probes that comprise HMGR sequences, e.g., on Southern blots. The hybridizing DNA regions are isolated by standard methods familiar to those of skill in the art. See e.g., Sambrook, et al. supra.

In an exemplary embodiment, HMGR sequences are isolated by screening plant DNA libraries with labeled oligonucleotide probes having sequences derived from nucleotides 3400-3498 of the DNA sequence of the *Aspergillus nidulans* HMGR gene shown in FIG. 1A and FIG. 1B, SEQ ID NO:1.

In addition to hybridizing with oligonucleotide probes having sequences derived from nucleotides 3400-3498 of the DNA sequence of the *Aspergillus nidulans* HMGR gene shown in FIG. 1A and FIG. 1B, SEQ ID NO:1, when operably linked to an expression control sequence e.g., a promoter sequence, HMGR nucleic acids encode polypeptides which catalyse the oxidation of NADPH by the catalytic subunit of HMGR in the presence of the substrate HMG-CoA. Kits for conducting HMGR assays are known in the art (e.g., HMG-CoA Reductase Assay Kit (Catalog Number CS1090) from Sigma Aldrich, St Louis Mo., 63103)

Other methods known to those of skill in the art can also be used to isolate and test DNA comprising HMGR sequences. See e.g., Sambrook, et al. for a description of other techniques for the isolation of DNAs related to DNA molecules of known sequence.

Sequence Features of HMGR Nucleic Acids

The full length HMGR gene from *Aspergillus nidulans* is shown in FIG. 8, as SEQ ID NO:1. Typically, HMGR nucleic acids comprise at nucleotides 3471-4234 of SEQ ID NO:1. Without being bound by theory it is believed that nucleotides 798-4315 comprise a membrane-spanning domain plus a catalytic domain; a catalytic domain is located at nucleotides 2863-4315 and functional subdomain of the catalytic domain is located at nucleotides 3471-4234. An intron sequence is present at nucleotides 3921-3976 of the catalytic domain. In some exemplary embodiments, the intron sequence at nucleotides 3921-3976 is removed.

The amino acid sequence corresponding to the 465 amino acid catalytic domain encoded by nucleotides 2863-4315 of SEQ ID NO:1 minus the intron at nucleotides 3921-3976 is shown in FIG. 2. Three cysteine amino acids at positions 94, 95 and 347 of SEQ ID NO:2 play a role in function of the HMGR catalytic domain. Thus, mutations that change the amino acids at these positions will render the catalytic domain non-functional.

Furthermore, there are 8 alpha helix domains and 8 beta sheet domains that play a role in function of the HMGR catalytic domain. Mutations which break up or alter these tertiary structures may eliminate or reduce function of the catalytic domain. The alpha helices are found at amino acids 128-143, 167-178, 183-190, 225-243, 284-291, 295-313, 380-387 and 399-443. In particular, the largest alpha helix domain in the protein, at amino acids 399-443 right before the C terminus of the protein, would be a likely target for wiping out function should the structure be altered.

C. Construction of Vectors Comprising HMGR Sequences

Once an HMGR nucleic acid has been isolated, various methods may be used to construct expression cassettes, vectors and other DNA constructs. Expression cassettes comprising HMGR sequences can be constructed in a variety of ways. The skilled artisan is well aware of the genetic elements that must be present on an expression construct/vector in order to successfully transform, select and propagate the expression construct in host cells. Techniques for manipulation of nucleic acids encoding HMGR sequences such as subcloning nucleic acid sequences into expression vectors, labeling probes, DNA hybridization, and the like are described generally in Sambrook, et al., supra.

In an exemplary embodiment, the HMGR sequence operably linked to a control sequence e.g., a promoter are cloned into an expression vector via suitable restriction endonuclease sites such that the promoter is upstream of and in-frame with the HMGR sequence. In another exemplary embodiment, various procedures, such as site directed mutagenesis are used to introduce a restriction site in a HMGR sequence. In another exemplary embodiment, various procedures, such as site directed mutagenesis are used to introduce a restriction site into a heterologous HMGR sequence such that the sequence can be cloned into an expression vector downstream and in-frame with a promoter sequence.

DNA constructs comprising HMGR nucleic acid operably linked to promoter sequence can be inserted into a variety of vectors. Typically, the vector chosen is an expression vector that is useful in the transformation of plants and/or plant cells. The expression vector may be a plasmid, virus, cosmid, artificial chromosome, nucleic acid fragment, or the like. Such vectors can be constructed by the use of recombinant DNA techniques well known to those of skill in the art. The expression vector comprising an HMGR sequence may then be transfected/transformed into the target host cells. Successfully transformed cells are then selected based on the presence of a suitable marker gene as disclosed below.

A number of recombinant vectors are available to those of skill in the art for use in the stable transfection of plant cells or for the establishment of transgenic plants (see e.g., Weissbach and Weissbach, (1989) *Methods for Plant Molecular Biology*, Academic Press; Gelvin et al., (1990) *Plant Molecular Biology Manual; Genetic Engineering of Plants, an Agricultural Perspective*, A. Cashmore, Ed.; Plenum: NY, 1983; pp 29 38; Coruzzi, G. et al., The Journal of Biological Chemistry, 258:1399 (1983); and Dunsmuir, P. et al., Journal of Molecular and Applied Genetics, 2:285 (1983). As is known in the art, the choice of a vector is influenced by the method that will be used to transform host plants, and appropriate vectors are readily chosen by one of skill in the art. In an exemplary embodiment, known vectors are used to create expression constructs comprising HMGR sequences.

Typically, plant transformation vectors include one or more cloned plant genes (or cDNAs) e.g., HMGR sequences, operably linked to a promoter sequence and a selectable marker. Such plant transformation vectors also typically include a transcription initiation start site, a heterologous nucleic acid the control of whose expression is desired, a ribosome binding site, an RNA processing signal, a transcription termination site, and/or a polyadenylation signal.

In some exemplary embodiments, plant transformation vectors may also include additional regulatory sequences from the 3'-untranslated region of plant genes, e.g., a 3' terminator region to increase mRNA stability of the mRNA, such as the PI-II terminator region of potato or the octopine or nopaline synthase (NOS) 3' terminator regions.

D. Guayule Plant Transformation and Selection and Regeneration Techniques

DNA constructs containing an HMGR nucleic acid operably linked to a promoter sequence can be used to transform plant cells and produce transgenic guayule plants with increased rubber production and increased regrowth in the field.

Exemplary plants for transformation with expression constructs comprising HMGR nucleic acids include, but are not limited to; guayule (*Parthenium argentum* Gray).

Transformation and regeneration of monocotyledonous and dicotyledonous plant cells is well known in the art, see e.g., Weising et al. Ann. Rev. Genet. 22:421-477 (1988); U.S. Pat. No. 5,679,558; *Agrobacterium Protocols* Kevan M. A. Gartland ed. (1995) Humana Press Inc. and Wang, M., et al. (1998) Acta Hort. (ISHS) 461:401-408. The choice of method varies with the type of plant to be transformed, the particular application and/or the desired result. The appropriate transformation technique is readily chosen by the skilled practitioner.

Exemplary transformation/transfection methods available to those skilled in the art include, but are not limited to: direct uptake of foreign DNA constructs (see e.g., EP 295959); techniques of electroporation (see e.g., Fromm et al., (1986) Nature (London) 319:791) high-velocity ballistic bombardment with metal particles coated with the nucleic acid constructs (see e.g., Kline et al., Nature (London) 327:70 (1987), and U.S. Pat. No. 4,945,050); methods to transform foreign genes into commercially important crops, such as rapeseed (see De Block et al., Plant Physiol. 91:694 701 (1989)), sunflower (Everett et al., Bio/Technology 5:1201 (1987)), soybean (McCabe et al., Bio/Technology 6:923 (1988); Hinchee et al., Bio/Technology 6:915 (1988); Chee et al., Plant Physiol. 91:1212 1218 (1989); Christou et al., Proc. Natl. Acad. Sci USA 86:7500 7504 (1989); EP 301749), rice (Hiei et al., Plant J. 6:271282 (1994)), corn (Gordon-Kamm et al., Plant Cell 2:603 618 (1990); Fromm et al., Biotechnology 8:833 839 (1990)), and *Hevea* (Yeang, H. Y., et al., In, Engineering Crop Plants for Industrial End Uses. Shewry, P. R., Napier, J. A., David, P. J., Eds.; Portland: London, 1998; pp 55 64). Other known methods are disclosed in e.g., U.S. Pat. Nos. 5,597,945; 5,589,615; 5,750,871; 5,268,526; 5,262,316; and 5,569,831.

Another exemplary method includes: transformation with DNA employing *Agrobacterium tumefaciens* or *Agrobacterium rhizogenes* as the transforming agent, electroporation, particle acceleration, etc. (see, e.g., EP 295959 and EP 138341). In one exemplary embodiment, Ti-derived vectors are used to transform a wide variety of higher plants, including dicotyledonous plants, such as e.g., potato, soybean, cotton, rape, tobacco, and rice (see e.g., Pacciofti et al., Bio/Technology 3:241 (1985); Byme et al., Plant Cell, Tissue and Organ Culture 8:3 (1987); Sukhapinda et al., Plant Mol. Biol. 8:209 216 (1987); Lorz et al., Mol. Gen. Genet. 199:178 (1985); Potrykus, (1985) supra; Park et al., J. Plant Biol. 38(4):365 71 (1995); and Hiei et al., Plant J. 6:271 282 (1994)).

*Agrobacterium tumefaciens*-meditated transformation techniques are well described in the scientific literature. See, e.g., Horsch et al. Science (1984) 233:496-498, and Fraley et al. (1983) Proc. Natl. Acad. Sci. USA 80:4803. Typically, a plant cell, an explant, a meristem or a seed is infected with *Agrobacterium tumefaciens* transformed with the expression vector/construct which comprises a Bul409 promoter sequence. Under appropriate conditions known in the art, the transformed plant cells are grown to form shoots, roots, and develop further into plants. The nucleic acid segments can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al., (1984) "Inheritance of Functional Foreign Genes in Plants," Science, 233:496-498; Fraley et al., (1983) Proc. Nat'l. Acad. Sci. U.S.A. 80:4803.

All plant cells which can be transformed by *Agrobacterium* and whole plants regenerated from the transformed cells can also be transformed so as to produce transformed whole plants which contain the transferred expression vector/construct which comprises a HMGR sequence.

There are various ways to transform plant cells with *Agrobacterium*, including:

(1) co-cultivation of *Agrobacterium* with cultured isolated protoplasts,
(2) transformation of cells or tissues with *Agrobacterium*, or
(3) transformation of seeds, apices or meristems with *Agrobacterium*.

Method (1) requires an established culture system that allows culturing protoplasts and plant regeneration from cultured protoplasts. Method (2) requires (a) that the plant cells or tissues can be transformed by *Agrobacterium* and (b) that the transformed cells or tissues can be induced to regenerate into whole plants. Method (3) requires micropropagation.

In the binary system, to have infection, two plasmids are needed: a T-DNA containing plasmid and a vir plasmid. Any one of a number of T-DNA containing plasmids can be used, the only requirement is that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and may also be used.

Transformed plant cells which are derived by any of the above transformation techniques can be cultured to regenerate a whole plant which possesses the desired transformed phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillan Publishing Company, New York, 1983; and Binding, Regeneration of Plants, Plant Protoplasts, pp. 21-73, CRC Press, Boca Raton, 1985, all of which are incorporated herein by reference. Regeneration can also be obtained from plant callus, explants, organs, or parts thereof. Such regeneration techniques are described generally in Klee et al. Ann. Rev. of Plant Phys. 38:467-486 (1987).

One of skill will recognize that, after an expression cassette comprising an HMGR sequence is stably incorporated in a transgenic guayule plant and confirmed to be expressed, it can be introduced into other plants by sexual crossing. Any of a number of standard breeding techniques can be used, depending upon the species to be crossed.

The skilled artisan will recognize that different independent transformation events will result in different levels and patterns of expression (Jones et al., EMBO J. 4:2411 2418 (1985); De Almeida et al., Mol. Gen. Genetics 218:78 86 (1989)), and thus that multiple events will likely need to be screened in order to obtain lines displaying the desired expression level and pattern. Exemplary method for screening transformation events may be accomplished e.g., by Southern analysis of DNA blots (Southern, (1975) J. Mol. Biol. 98: 503), Northern analysis of mRNA expression (Kroczek, J., (1993) Chromatogr. Biomed. Appl., 618(1 2): 133 145), Western analysis of protein expression, and/or phenotypic analysis e.g., resistance to an herbicide can be detected by treatment with the herbicide. Expression of the heterologous HMGR nucleic acid can also be detected by measurement of the specific RNA transcription product. This can be done by, for example, RNAse protection or Northern blot procedures.

Once transgenic guayule plants have been obtained, they may be grown to produce plant tissues or parts having the desired phenotype. The plant tissue or plant parts may be harvested, and/or the seed collected. The seed may serve as a source for growing additional plants with tissues or parts having the desired characteristics e.g., increased rubber production.

E. Measuring Increased Rubber Content and Increased Regrowth in Transformed Guayule Plants Rubber yield can be expressed as a product of rubber content (% rubber) and biomass (dry weight/unit area). Thus, rubber yield may be improved by increasing either biomass and/or rubber content. In an exemplary embodiment, an increase in rubber content increases the processing efficiency of the guayule shrub.

Methods for determining dry weight, rubber, and resin content are known in the art (see e.g., Jasso de Rodriguez et al. (1993) J. Am. Oil Chem. Soc. 70:1229-1234).

Increased regrowth in the field is measured as disclosed in Example 1 hereinbelow. In general, increased regrowth in the field refers to the survival rate following harvest by pollarding. As is known in the art, guayule is typically harvested by pollarding, that is harvesting the branches by cutting leaving the root-crown to regrow new branches. Typically, after a single pollarding, less than 100% of the plants survive and regenerate new growth. Plants pollarded two consecutive years have an even lower survival rate than the first year (see e.g., D. T. Ray et al. (1992) Industrial Crops and Products 1:11-15). Regrowth can be influenced by the time and season of harvest. Indeed, plants harvested in hot months typically have lower survival rate/lower regrowth in the field than due plants harvested in cooler months.

Accordingly, in an exemplary embodiment, increased regrowth in the field is measured by comparing the survival rate after pollarding of transgenic guayule plants comprising a heterologous HMGR nucleic acid which is expressed in the transgenic guayule plant to the survival rate after pollarding of otherwise isogenic guayule plants which do not express a heterologous HMGR nucleic acid.

The following examples are offered to illustrate, but not to limit the invention.

EXAMPLES

Example 1

The following example illustrates development and testing of transgenic guayule plants having increased rubber production and increased regrowth.

Materials and Methods for Example 1

Maintenance of Guayule Plants In Vitro

Guayule line G7-11 was established as described previously (Castillón and Cornish 2000). A shoot tip 10 mm or longer was excised and transferred to a Magenta box containing 80 ml fresh ½MS-I0.1 [half-strength MS medium (Murashige and Skoog 1962) plus 2.5 mM CaCl2, 2.0 mM Mg(NO3)2, and 0.1 mg/l IBA, 15 g/l sucrose and 8 g/l agar, pH 5.8, MS vitamin was replaced with B5 (Gamborg et al. 1968) vitamin]. The cultures were maintained at 25° C. under cool-white fluorescent light (~50 µmol/m2/s, 16/8-h day/night photoperiod). Roots developed 1-2 weeks after the shoot tips were transferred to this medium.

Plasmid Construction

Plasmid pND4 (FIG. 1A and FIG. 1B) was constructed based on pPZP200 (Hajdukiewicz et al. 1994). It contained a double 35S promoter (Datla et al. 1991) driven BAR gene (Christensen and Quail 1996) and a potato ubiquitin-3 promoter (Garbarino and Belknap 1994) driven intron containing GUS gene (Vancanneyt el al. 1990). Plasmid pND4-HMGR(tAN) was constructed by replacing the GUS gene with a truncated HMGR gene (AF479817). Plasmid pND4 and Plasmid pND4-HMGR(tAN) were used to transform *Agrobacterium* EHA101 (Hood et al. 1986) competent cells. The transformed *Agrobacterium* EHA101 either harboring pND4 or pND4-HMGR(tAN) were used to transform the guayule G7-11.

*Agrobacterium* overnight culture were prepared by inoculating 50 µl long-term glycerol stock into a 50 ml Falcon tube containing 5 ml LB medium plus 20 mg/l rifampicin and 200 mg/l spectinomycin, and shaking at 200 rpm at 28° C. The suspension then was centrifuged for 15 min at 1,600×g at room temperature. The supernatant was discarded and the pellet was re-suspended in 25 ml of Inoculation Solution (1/10MS salts plus BA 2 mg/l, NAA 0.5 mg/l, glucose 10 g, acetosyringone 200 µM, pluronic F68 0.05%, pH 5.2).

Leaf Tissue Transformation

Leaf tissue transformation was followed Dong et al. (2006) with some modifications. Leaves were cut from the plants in the Magenta boxes. Each leaf was placed in a Petri dish containing 5 ml *Agrobacterium* suspension. The adaxial side (upper side) was up. The leaf was cut into 10 mm strips and immediately transferred to an empty Petri dish. The leaf strips were set one by one but not overlapped. When this Petri dish was full, all leaf strips were blotted with the filter paper and placed in an empty Petri dish. The Petri dish was sealed by parafilm and left in dark. The co-cultivation was replaced by this co-desiccation according to Cheng et al (2003). Three days later, leaf strips were transferred to NDB1T (MS medium without NH4NO3 but with 8 g/l KNO3, 1 mg/l BA, 30 g/l sucrose, 8 g/l agar, and 400 mg/l timentin (Cheng et al. 1998) for recovery at low light for 5 days. The leaf strips were then transferred to (½NH4) MSB1TG1 (MS medium lowered NH4NO3 to 10.36 mM but increased KNO3 to 39.44 mM, 1 mg/l BA, 30 g/l sucrose, 8 g/l agar, 400 mg/l timentin, and 1 mg/l glufosinate-ammonium) for selection under low light. Two weeks later, the leaf strips were transferred to MSB1TG1 (MS medium plus 1 mg/l BA, 30 g/l sucrose, 8 g/l agar, 400 mg/l timentin, and 1 mg/l glufosinate-ammonium) and subcultured every 2 weeks under high light until green shoots emerged. Green shoots 10 mm and longer were transferred to ½MSI0.1TG1 (same as ½MSI0.1 but with 200 mg/l timentin and 1 mg/l glufosinate) for rooting for 2-4 weeks. Shoot tips of the rooted plantlets were transferred to half-strength MS medium for maintenance or inserted into a sterile cellulose plug in liquid ½MSI0.1 medium for rooting and then transplanted into soil.

PCR Analysis

DNA was extracted using Sigma Kit (Sigma-Aldrich USA). Approximately 150 mg leaf tissue was frozen in liquid nitrogen and ground to a fine powder using a mortar and pestle, following the procedures of the manual.

PCR was carried out in 50 μl of a mixture containing 5 units of Taq DNA polymerase (New England Biolabs, USA) and 5 μl of 10×ThermoPol Reaction Buffer (supplied with the enzyme), 4 μl of dNTP (2.5 mM each), 200 ng genomic DNA or 20 pg plasmid DNA, and 100 ng of HMGR specific forward (5'-AGAACGTTATTGGCACCCTG-3', SEQ ID NO:3) and reverse (5'-GTGCTTTCTCAACGCCTTTC-3' SEQ ID NO:4) primers. After heating the samples to 94° C. for 2 min, the reaction proceeded with 35 cycles of 94° C. for 30 s, 58° C. for 45 s and 72° C. for 15 s. A final elongation step was carried out at 72° C. for 10 min. PCR products were separated by electrophoresis on 0.9% (w/v) agarose gels.

Quantitative Real Time RT-PCR Analysis

Stem (10 mm diameter) bark tissue from three field-grown shrubs, or whole stem and leaves from 2 month-old tissue cultured plants, of each transgenic and control guayule was the source of total RNA (2 μg) used as template for cDNAs using the SuperScript III First-Strand Synthesis System for Reverse Transcriptase (RT)-PCR (Invitrogen USA). Quantitative PCR (qPCR) on cDNAs of HMGRtAN (transgene from *Aspergillus nidulans*) and PaEIF4A (endogenous guayule control gene) was carried out using Applied Biosystems 7500 Fast Real Time PCR System and the SYBR® Green chemistry (Applied Biosystems USA). The following combinations of forward/reverse primers and probes were used for the qPCR reactions: for HMGRtAN 5'-GAGGAGGGTAAGAGCGTCATGA-3' SEQ ID NO:5)/5'-GTACCGGCAAGGGCAGTCT-3' SEQ ID NO:6), and for PaEIF4A 5'-TTGAATGCCAGGCTTTGGTT-3+ SEQ ID NO:7)/5'-GCGCGCATGACCTTCTCA-3' SEQ ID NO:8) Fast SYBR® Green PCR Master Mix (2×) (Applied Biosystems USA) was used in each qPCR reaction in combination with 50 nM of each primer with the following temperature regime: 95° C. for 20 s, followed by 40 cycles of 95° C. for 3 s and 60° C. for 30 s. Data were analyzed using the 7500 Fast System Detection Software (Applied Biosystems USA) with manually set baseline and threshold. The relative expression values were calculated using the 2-ΔΔCt method as known in the art (see e.g., Livak and Schmittgen, (2001) Livak, K. J., and Schmittgen, T. D., Methods 25, 402-408). The amplification efficiencies of AnHMGR and eIF4a genes were determined to be equal.

Protein Analysis

Stem (10 mm diameter) bark tissue from field-grown shrubs, or whole stems and leaves from tissue cultured plants, of each transgenic and control guayule was ground to fine powder with liquid nitrogen and homogenized with 10 mM Tris-HCl, pH 7.0 protein extraction buffer supplemented with 350 mM sucrose, 30 mM EDTA, 10 mM 2-mercaptoethanol, 3.5% Polyvinylpyrrolidone, and Halt™ protease inhibitor cocktail (Thermo Scientific USA). Homogenate was centrifuged at 5,000 g for 10 min at 4° C., the resulting supernatant filtered through one layer of Miracloth (Millipore USA), and the filtrate centrifuged at 100,000 g for 1 h at 4° C. The supernatant (soluble proteins) was transferred to a clean tube, and the pellet (microsomal proteins) was resuspended in 200 mM potassium phosphate, pH 6.9 buffer supplemented with 25 mM DTT and Halt™ protease inhibitor cocktail. Denatured soluble and microsomal proteins (10-20 μg) were separated on NuPAGE® Novex® 4-12% gradient gels (Invitrogen USA) with MOPS-SDS running buffer (50 mM MOPS, 50 mM Tris Base, pH 7.7, 0.1% SDS, 1 mM EDTA), then electroblotted to nitrocellulose membrane with Towbin buffer (25 mM Tris Base, pH 8.3, 192 mM glycine, 10% methanol). Membranes for western blot were blocked overnight with SuperBlock® TBS blocking buffer (Thermo Scientific USA) supplemented with 0.05% Tween-20, incubated overnight with 100 ng/ml of anti-human HMGR polyclonal antibody (Millipore USA), and for 1 h with 2 ng/ml of anti-rabbit IgG-Horse Radish Peroxidase (HRP) conjugate antibody (BioRad USA). Membrane was washed five times for 5 min each with TBS (50 mM Tris, pH 7.4, 150 mM NaCl) buffer supplemented with 0.05% Tween-20 after membrane blocking step and in between antibody incubations. Antibodies were diluted in SuperBlock® TBS blocking buffer supplemented with 0.05% Tween-20. HRP signal was detected with SuperSignal® West Femto Maximum Sensitivity Substrate (Thermo Scientific USA) following manufacturer instructions.

Transformed In Vitro Plants

Rooted plantlets from transferred shoot tips were grown on ½MS-I0.1 medium in Magenta boxes for 2-3 months on half-strength MS medium. Plantlets were carefully separated from the medium and lyophilized for 48-72 hours. The dried tissues were hand ground (mortar and pestle) in liquid nitrogen, air dried overnight, then loaded into 11 mL stainless steel extraction cells (Dionex, USA). Three sequential extractions were performed at ambient temperature: 1) acetone, to remove resinous material and the low molecular weight organic solubles, 2) methanol, to remove chlorophyll and other alcohol-soluble materials (following Pearson et al. Industrial Crops and Products 31 469-475 (2010), 3) cyclohexane, to remove rubber. Natural rubber was quantified gravimetrically (from ASE vials) and by determination of the concentration of tetrahydrofuran (THF) resolubilized rubber using High Performance Liquid Chromatogrphy (HPLC), as follows. Three mL filtered THF was placed directly into ASE vials and gently shaken overnight. The solubilized rubber was filtered (0.6 um syringe filters) then injected (50 uL load) into 2 Phenogel 10 um 50A columns (Phenomenex, Torrance, Calif.) in series. Chromatograms were determined using Dawn multiple angle light scattering (Wyatt Technologies, Santa Barbara Calif.) and HP differential refractive index (RID) detectors. Molecular weights were determined from both chromatograms using ASTRA V4 software. The quantity of rubber was calculated by integrating only the high molecular weight rubber peak from the resulting RID chromatogram.

Transplanting and Field Measurements

Shoot tips of rooted plantlets were inserted into a sterile cellulose plug, then placed into glass culture tubes in liquid ½MSI0.1 medium for rooting. Plantlets were removed from the tube when a visible root was showing and placed into a pot with Sunshine Mix potting soil in the greenhouse. Plants were later transplanted into five gallon pots which were used to transplant them into the field between Mar. 21, 2007 and Apr. 2, 2007. The design included 12 replications per line and 2 plants/entry/rep in a randomized complete block design. Plots were irrigated, hand weeded, and fertilized as needed, monitored for pests and diseases (none). Plant height and width were measured monthly and used to calculate plant perimeter (avg. width*3.14159). Growth was determined by height and perimeter changes as a percentage of the initial value. The dormancy break was scored on Mar. 13, 2008 as 0=most dormant=late dormancy break (no leaf buds initiated), and 5=early maturity (first new leaves fully expanded). Flower buds were scored on Apr. 3, 2008 as 0=no flower buds initiated, and 5=a full anthesis of the first flush of flowers. Bloom density was scored visually May 22, 2008 under a protocol from 1 to 9 with: 1=very low incidence of bloom on the plant, and 9=very dense bloom on the plant. The scores were independent of plant size resulting in a density rather than a total bloom number score.

Harvest

Field harvests began in January 2009 when the plants were about 22 months old and took place over about 90 days. Plants were photographed prior to harvest then pollarded approximately 4 inches from the soil surface. The fresh weight was measured and plant descriptors recorded (Table 4) prior to chipping. In addition to descriptors described by Coffelt and Johnson (2011), the following characteristics were recorded: 1) number of secondary stems, 2) distance above the ground to the first side branch, 3) side branch angle, 4) leaf serration size, 5) top shape, 6) paired samples the same 7) tendency to stay green, and 8) presence or absence of cupped leaves. The stem diameter and wood diameter were measured twice for the largest stem of each sampled plant, then used to calculate bark, wood, and total cross sectional areas, as well as the % bark in the cross section. Individual plants were chipped in two stages. First through a large slow revolution hammermill with no screen, for a coarse chop, followed by a high speed hammermill with about an 8 to 10 mm screen for the fine chop that resulted in plant particle sizes suitable for conducting rubber and resin analyses on the ASE. The whole chipped shrub was subsampled for 1) fresh latex quantification and rubber molecular characterization, 2) moisture determination, and 3) drying for rubber and resin quantification.

Shrub Characterization

Freshly chipped shrub was immediately stabilized in an ammoniated antioxidant solution following the method of Coffelt and Nakayama. Latex was quantified following methods known in the art (see e.g., Cornish, K., et al. (1999) Industrial Crops and Products 10, 2, 121-136). Moisture contents were determined using samples of freshly harvested shrub, as weight before and after drying for 48 hours in a forced air oven.

Statistical Analysis

The results of the study were statistically analyzed with PASW Statistics 18 software (version 18.0.3, IBM SPSS, Chicago, Ill., USA) using Dunnett's multiple comparison test (two sided) at a preset significance level of 5% to determine if significant differences existed between genotypes.

Results for Example 1

In Vitro Plants

Figure 3:
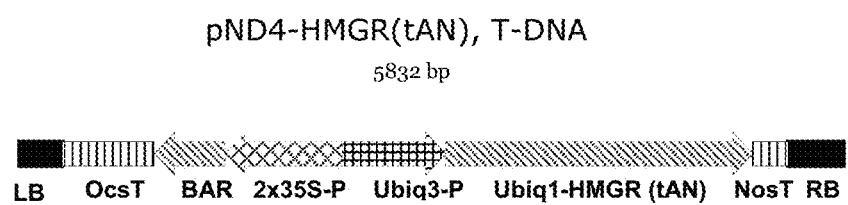
FIG. 3. Map of pND4-HMGR(tAN), T-DNA region. LB: left border; OcsT: octopine synthase gene terminator; BAR: herbicide glufosinate-resistant gene; 2×35-P: double 35S promoter; Ubiq3-P: potato ubiquitin-3 promoter; Ubiq1-HMGR(tAN): the first ubiquitin gene fused to the truncated HMGR gene from *Aspergillus nidulans*; Nos-T: nopaline synthase gene terminator; RB: right border.

The transformation plasmid pND4-HMGR(tAN) was constructed with a modified binary vector (pND4) known in the art (see e.g., Dong et al. (2006) Plant Cell Rep 25:26-34) and the HMGR gene from *Aspergillus nidulans* containing only the 465 amino acid catalytic domain driven by a constitutive promoter (potato Ubiq3). The resulting truncated HMGR1 plasmid construct pND4-HMGR(tAN) is shown schematically in FIG. 3; the T-DNA sequence is in FIG. 1A and FIG. 1B. The BAR gene driven by a double 35S promoter was used as a marker gene for Glufosinate resistance selection.

*Agrobacterium*-mediated transformation of an advanced homozygous inbred line of the AZ-2 cultivar yielded five independently transformed lines. Overall transformation efficiency of this plasmid into guayule using the method described was ~3%. PCR results (FIG. 2) for four of those lines clearly indicate the presence of the HMGRtAN gene inserted into the in vitro plants. As an early indicator of the efficacy of HMGR insertion to increase isoprenoid production, the rubber and resin content of two-month old in vitro plantlets was determined. The natural rubber content of the plantlets was equal to or lower than that of control plants in all cases except that of line HMGR6, which showed up to a 65% increase in rubber over the tissue culture control (Table 1). The resin content of line HMGR2 was lower than that of the other lines. Three of the five transformed lines, including line HMGR6, were successfully grown up and transferred to sorba rods, then to soil, with sufficient replicates and controls (24 plants for each line) to transport to Maricopa, Ariz., for field evaluation.

Field Plants

Field plots included AZ-2 seed controls as border plants and within the plot design, tissue culture (TC) controls, vector controls (VC), and experimental transgenic overexpressed (HMGRoe) plants. Greenhouse stabilized plants were transplanted to Field 110 at the University of Arizona Maricopa Agricultural Center in late March/early April 2007. Plant size was measured ~monthly starting May 2007. From the start of the field trial, and in all cases, the AZ-2 seed control plants were larger than tissue culture (control or experimental) lines (FIG. 3a). Likewise, from the start of the trial, experimental line HMGR6 plants were smaller than vector control plants. Growth of plants was fastest the first few months; from May 2007 to July 2007 plants grew 10-20 cm in height (FIG. 3b) and 40-60 cm in perimeter. There was no significant growth in terms of measured height (FIG. 3a, FIG. 3b) or perimeter (data not shown) during the winter months (November 2007-March 2008) and very little the following winter (October 2008-January 2009, data not shown). Peak growth rates were in the Spring and Fall, as expected. It is noteworthy that growth rates, measured as changes over time in measured height or perimeter, did not vary between lines, whether seed, tissue culture control, vector control, or HMGRoe lines (FIG. 3a).

Dormancy break, flower bud, and bloom density measurements were made on Mar. 13, Apr. 3, and May 22, 2008, respectively, following the first winter, when the plants were ~14 months old. Dormancy break (0-5) is a score of leaf growth initiation to indicate first dormancy break. Flower bud score (0-5) is a measure of flower maturity of first flush of bloom at a time that indicates flower bud dormancy break. Flower buds were scored approximately 1 month after leaf dormancy break, at the time of maximum difference in flower maturity score between early and late maturing plants. A score of 0 indicates that no flower buds have initiated, while a score of 5 indicates that all first flush flowers are fully open (full antithesis). Dormancy break and flower bud scores were highest for the AZ-2 seed controls (Table 2). Overall dormancy break and flower bud score were related in this study, as expected, since they are two different measures of plant maturity on different parts of the plant.

Bloom density is a measure of how heavily the plant blooms once all genotypes are fully flowering. Plants were individually scored for bloom density against a protocol from 1=very low incidence of bloom to 9=very dense bloom, with a focus on flower density independent of plant size. For example, a score of 1 indicates from 1-5% coverage of the plant surface area, and 9 indicates from 40 to 50% coverage of the plant surface area. The average scores for control plants were 7.1 (vector control). HMGRoe lines 2, 3, and 6 scored 7.0, 7.0, and 5.7, respectively, and AZ-2 seed at 7.2, indicating less bloom density for one of three HMGRoe lines (HMGR6). The correlation between flower bud density and flower initiation over all lines was 0.67.

Plants were harvested starting in January 2009 after ~22 months in the field. Comparisons of critical interest here are those of the transgenically modified lines against the vector control. The average dry biomass over all harvests for lines HMGR2 (2.16 kg) and HMGR3 (2.32 kg) were similar to that of the VC (2.24 kg) (Table 3). Line HMGR6 plants were significantly lower in average biomass (1.27 kg). Plant biomass was measured throughout the 90 day harvest period, mid-January to mid-April 2009.

Figure 4:
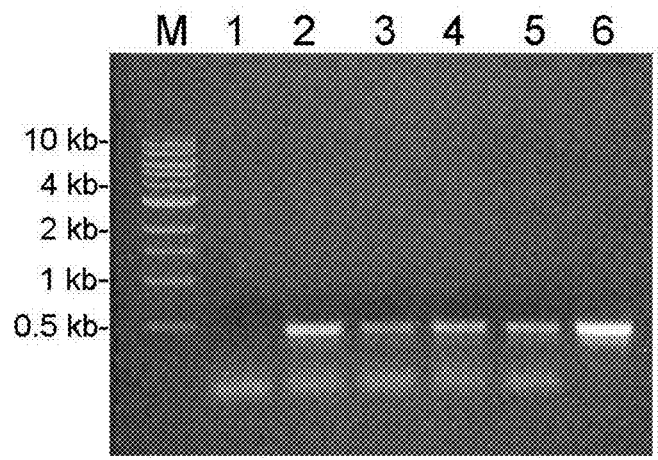
FIG. 4. PCR analysis of in vitro guayule plants. Lane M: 1 kb DNA Marker; Lane 1: Control: advanced homozygous inbred line of the AZ-2 cultivar used as starting material for transformations; Lanes 2, 3, 4, 5: Transgenic plants HMGR2, HMGR3, HMGR6 and HMGR7, respectively; Lane 6: Plasmid pND4'-HMGRtAN.
Figure 5A:
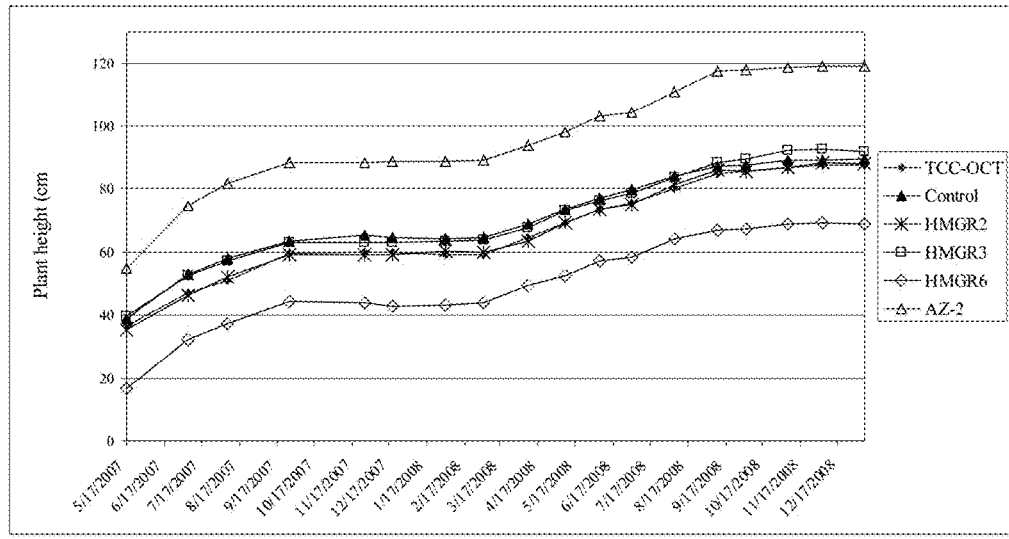
FIGS. 5A and 5B.
Figure 5B:
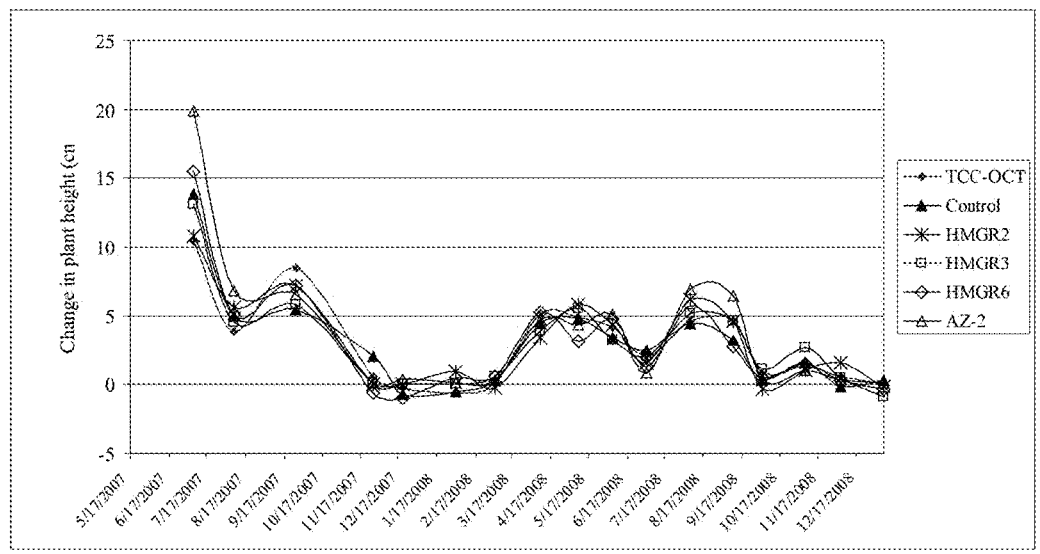

Plant lines HMGR6 and AZ2 had the least changes in biomass during the harvest period; other lines had various dynamic changes. Biomass for the TC plants dropped 46% (2.78 kg (first 4 harvests) to 1.51 kg (last 4 harvests) during the harvest period (FIG. 5). Line HMGR2 first dropped (−50%) then increased (+66%), while line HMGR3 first increased (+5%) then dropped (−52%) over the total harvest period. All other lines remained stable; i.e. neither significant growth nor loss in biomass was observed. These trends, shown in FIG. 5, illustrate particularly the dynamic changes taking place in the plants after mid-March, the time of expected dormancy break (Table 2). Nevertheless, some consistencies were clear throughout harvests. For example, the AZ-2 seed control plants were larger in biomass (by 30% or more), and in plant height and width, All tissue culture plants, whether transgenically modified or not, were accordingly lower in plant biomass (FIG. 4) and dimensions. Metabolite analysis included latex quantification from freshly harvested plants, and % rubber and resin from solvent extraction of dried plant tissues (Table 3). The % latex in wet shrub was lower in HMGRoe lines than in the VC control, only statistically significant for HMGR2. However, natural rubber content, determined as a dry weight percentage following organic solvent extraction was the same, about 3%, for all lines (average of all lines 3.1%, sd 0.05). Similarly, the particle size of extracted latex and the molecular weight (and distribution) of rubber from that latex was equivalent for all experimental and control lines (Table 3). The resin content (% dw acetone extractables) was also the same for transformed and control lines (average of all lines 3.89%, sd 0.10) (Table 3). Rubber and latex content for the seed controls was 30% or more higher than for the transplanted tissue culture plants; resin content was also higher, but less so (3.89% vs. 4.10% dw) (Table 3).

Twenty-two (22) plant descriptors were recorded to characterize shrub phenotypes (Table 4). Quantification of the phenotype descriptors allowed univariate analysis of variance across all 12 harvests and all replicates. In all cases the VC was used as the control plant. Results of that analysis indicate descriptors related to plant size and shape varied consistently, in that the HMGR6 line was smaller and the AZ-2 seed line larger than the VC plants.

All shrubs were pollarded 3-5 inches above the soil, and measurements made to characterize the plant cross-section. The stem and wood diameters, and bark, wood, and total cross sectional areas reflect the plant size and biomass. Indeed, in every case line HMGR6 had the smallest stem size dimensions, the seed control had the largest dimensions, and all other lines were in between and essentially the same. On a percentage basis, the VC dimensions were about 50-70% that of the seed control, and line HMGR6 20-45% that of AZ-2 seed plants. Interestingly, the % of bark in the plant cross section was the highest for line HMGR6 (49%). While that might be expected for a smaller plant, there was no significant difference between the VC (42.5%) and the seed control (41.2%) despite the large differences in size between those plants. Further, bark cross-sectional area was positively correlated to rubber yield (kg/shrub, R2=0.79). However, for line HMGR6 the increased bark thickness did not overcome the biomass differences; yield per shrub was almost half that of the VC.

The number of main branches was dramatically different between the AZ-2 seed line (avg about 1), compared to the experimental lines, about 2.5 except for the HMGR6 line, average almost 4 main branches. The HMGR6 line also had more secondary stems than all controls, and the lowest distance from the ground to the first branch—in other words, more of a compact spreader than upright shrub morphology.

Leaf size and shape varied between control and experimental lines, and in some cases within experimental lines (Table 4). The HMGR6 line was distinguished by the lowest score for 'stay green'. Chlorophyll is an isoprenoid product from the plastidic (MEP) pathway; limited evidence of crosstalk between the MEV (cytosol) and MEP pathways exists, suggesting pools of IPP from one pathway may influence production of that from the other (Lichthentaler, 2007; Kirby and Keasling, 2009).

In brief, insertion of the HMGR gene into guayule produced a higher rubber content phenotype in tissue culture for one line of modified plants and produced a dwarf phenotype in the field for that same line. Three other lines did not yield differentiable phenotypes.

Figure 7:
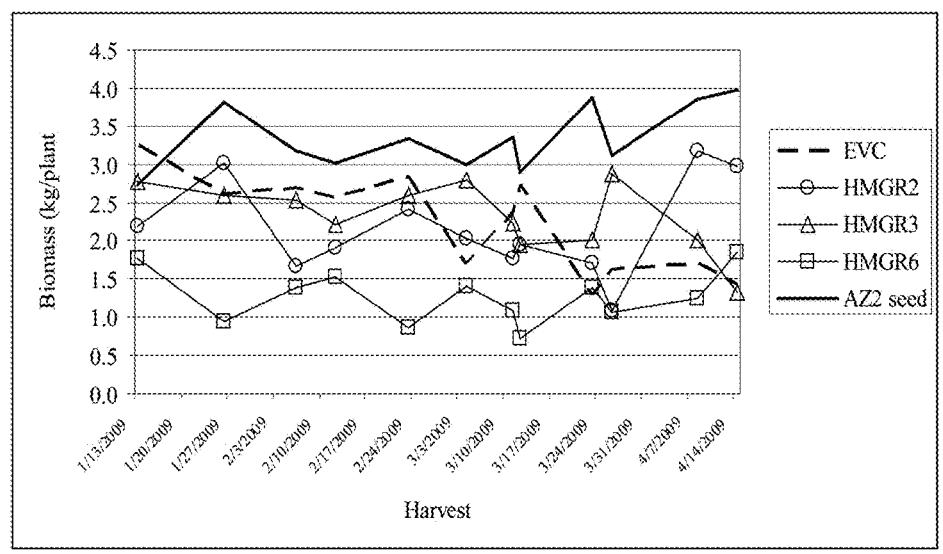
FIG. 7. Changes in average plant dry biomass, expressed as kg dry biomass per plant, during harvests for field grown guayule, over the period January-April 2010. Each data point represents the average of 2 paired plants. EVC=Vector Control.

In order to resolve the discrepancies between laboratory and field results, gene expression was measured by quantitative real-time PCR analysis for both tissue culture and field grown plant tissues. Expression of the inserted HMGR gene in terms of 2-ΔΔCt relative expression (see e.g., Livak and Schmittgen, (2001) Methods 25, 402-408) is shown in FIG. 7a and FIG. 7b, for tissue culture and field plants, respectively. These results confirm expression of the HGMR transgene in modified plants and not in control plants (VC and non-transformed). The relative expression of the 3 HMGRoe tissue culture lines was not statistically different; in the field HMGR6 (mean expression=0.97) was significantly higher than HMGR3 (mean expression=0.17) (two sample T-test, P<0.03). PCR primers used for this analysis did not hybridize to the endogenous guayule HMGR and as a consequence did not amplify.

Plant Regrowth

Figure 6:
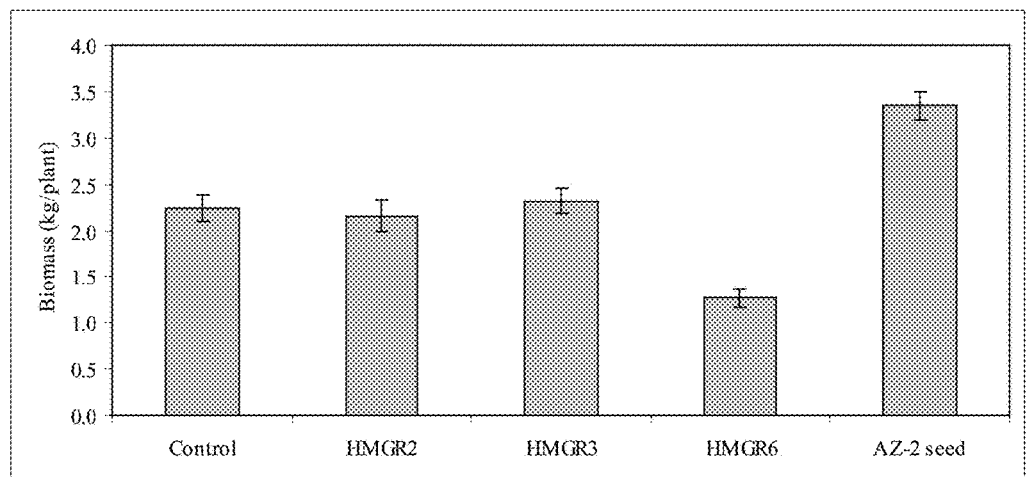
FIG. 6. Plant dry biomass (kg biomass per plant) averaged by line (+/−SE), at harvest for field grown guayule transplanted as seedlings to Field 110 at the University of Arizona Maricopa Agricultural Center in late March/early April 2007. Harvests took place from January to April, 2009. VC=Vector Control, TCC=tissue culture control.

Plants remained in the field following pollarding harvests in Spring 2009. Regrowth was evaluated Jun. 30, 2009. The overall survival rate for the AZ-2 seed control was 38%; for the TC, 42% of the plants survived (FIG. 6). Remarkably, over 50% of the HMGRoe plants survived (FIG. 6), with the highest survival rate 75% for line HMGR6. The increased survival rate was even more dramatic when comparing regrowth following the last 8 harvests (Mar. 17-Apr. 15, 2009). As ambient temperatures rose (high temp 24-40° C.), survival rates fell, down to 13% for the AZ-2 seed and the VC control plants. Two of the three HMGRoe lines showed higher survival rate, HMGR2 at 38% and HMGR6 at 50% (FIG. 6). All surviving plants reached about the same size: 50 cm height and 150 cm perimeter with no differences between lines within the measured variation (data not shown).

Two years later, on Mar. 21-23, 2011, the regrown plants were harvested and evaluated for growth characteristics and metabolite production. Results, shown in Table 5, confirm the enhanced survival rate for line HMGR6, the only line of 7 evaluated to have 100% survival if the initial 24 plants from 2007. Trends with respect to plant size were similar to the first harvest; i.e., line HMGR6 the smallest, and the AZ-2 seed control the largest. Line HMGR3 was the same as the vector control. All regrown plants were smaller in terms of size (plant height, Table 5) and dry weight compared to the original harvest, with the exception of line HMGR6 (+25% in biomass). In all lines, the rubber content was reduced (on a dw basis) by as much as −36% (AZ-2) while, remarkably, the resin content increased dramatically (+103% for AZ-2). Rubber molecular weight was the same for all experimental and control lines (data not shown).

Example 2

The following example illustrates the use of HMGR in a binary construct, combined with farnesyl pyrophosphate synthase (FPPs), a known rubber biosynthesis initiator, to produce a guayule plant with enhanced rubber production and further illustrates the use of a cold-inducible promoter for overexpression of HMGR and FPPs, in plants subjected to cold treatment, to produce a guayule plant with high rubber production.

Materials and Methods for Example 2

Materials and methods for Example 2 are as disclosed above in Example 1.
Plasmid Construction
Plasmid pND9 (FIG. 10A, and FIGS. 10B, 10C, and 10D) was constructed based on pPZP200 (Hajdukiewicz et al. 1994, Plant Mol Biol. 1994 September; 25(6):989-94). It contained a potato polyubiquitin promoter 409Ps (Garbarino et al., 1995. Plant Physiol. 109 (4), 1371-1378.) driven NPTII gene (Beck et al, 1982, Gene 19 (3), 327-336) and a double CaMV 35S promoter (Kay et al, 1987, Science 236 (4806): 1299-1302) driven GUSplus gene (Provided by CAMBIA). Plasmid pND9-P427-HMGR-FPPS (FIG. 11A, and FIGS. 11B, 11C, and 11D) was constructed by replacing the GUSplus gene with a truncated HMGR gene (AF479817) and a FPPS gene (Koyama et al, 1993, J. Biochem. 113 (3), 355-363) linked with a 2A peptide gene (Donnelly et al, 2001, J. General Virology, 82, 1013-1025), driven by another potato polyubiquitin promoter 427 (Rockhold et al, 2008, Am. J. Pot Res: DOI 10.1007/s12230-008-9015-5). Plasmid pND9-$P_{CBF2}$-HMGR-FPPS (FIG. 12A, and FIGS. 12B, 12C, and 12D) was modified from Plasmid pND9-$P_{427}$-HMGR-FPPS by replacing Promoter $P_{427}$ with a cold inducible promoter $P_{CBF2}$ ($P_{CBF2}$ is known in the art see e.g., Kazuko Yamaguchi-Shinozakia, and Kazuo Shinozakic: Trends in Plant Science Volume 10, Issue 2, February 2005, Pages 88-94). Plasmid pND9, Plasmid pND9-$P_{427}$-HMGR-FPPS and Plasmid pND9-$P_{CBF2}$-HMGR-FPPS were used to transform *Agrobacterium* EHA101 (Hood et al. 1986, J. Bact. 168 December 1986, p. 1291-1301) competent cells. The transformed *Agrobacterium* EHA101 either harboring pND9, pND9-$P_{427}$-HMGR-FPPS and pND9-PCBF2-HMGR-FPPS were used to transform the guayule G7-11 leaf tissue.
Although the cold inducible promoter CBF2 was used in the experiments disclosed herein, other cold inducible promoters are expected to give similar results. Exemplary cold inducible promoter useful in the methods disclosed herein include, but are not limited to e.g., corl5a (potato); Cor39 (duram wheat); WRKY71 (rice); wcs120 (wheat); RCI2A (*Arabidopsis*); RCI2B (*Arabidopsis*).
*Agrobacterium* Preparation:
*Agrobacterium* preparations were as described above in Materials and Methods for Example 1.
Leaf Tissue Transformation
Same as Materials and Methods for Example 1, but used 30 mg/l kanamycin instead of 1 mg/l gluforsinate for selection.

PCR Analysis
DNA was extracted using Gen Elute Plant Genomic DNA Miniprep Kit (Sigma-Aldrich USA). Approximately 150 mg leaf tissue was frozen in liquid nitrogen and ground to a fine powder using a mortar and pestle, following the procedures of the manual.
PCR was carried out in 50 µl of a mixture containing 5 units of Taq DNA polymerase (New England Biolabs, USA) and 5 µl of 10×ThermoPol Reaction Buffer (supplied with the enzyme), 4 µl of dNTP (2.5 mM each), 200 ng genomic DNA or 20 pg plasmid DNA, and 100 ng of HMGR specific forward (5'-CATCTTGTCAGAGCGCACAT-3', SEQ ID NO:9) and reverse (5'-CAAATCATCGTTGTCCATGC-3' SEQ ID NO:10) primers. After heating the samples to 94° C. for 2 min, the reaction proceeded with 35 cycles of 94° C. for 30 s, 58° C. for 45 s and 72° C. for 15 s. A final elongation step was carried out at 72° C. for 10 min. PCR products were separated by electrophoresis on 0.9% (w/v) agarose gels.
Determination of Rubber Content for Tissue-Culture Plants.
Rooted plantlets from transferred shoot tips were grown on ½MS-I0.1 medium in Magenta boxes for on half-strength MS medium. The plantlets were placed in a growth chamber (CONVIRON CMP5090) under 25° C. 16 hour day/10° C. 8 hour nights for 77-78 days. Plantlets were carefully separated from the medium and lyophilized for 48-72 h. The dried tissues were hand ground (mortar and pestle) in liquid nitrogen, air dried overnight, then loaded into 11 mL stainless steel cells for extraction by Accelerate Solvent Extraction (Dionex, USA). Three sequential extractions were performed at ambient temperature in acetone, to remove resinous material and the low molecular weight organic solubles, next with methanol, to remove chlorophyll and other alcohol-soluble materials (following Pearson et al., 2010), and finally with cyclohexane, to extract and quantify the natural rubber content. Natural rubber was quantified gravimetrically from the weight of ASE vial cyclohexane extracts.

Results for Example 2

Guayule plants subjected to *Agrobacterium*-mediated transformation in vitro using the target plasmids were grown out on Glufosinate selection media; the presence of the transgenes was confirmed by PCR. Following cold treatment, the extractable content of terpene resins and sterols (acetone extract, see e.g., Schloman et al. 1983, J. Agric. Food Chem. 31, 973-976) and natural rubber (cyclohexane extract) was determined gravimetrically (see Methods). Results from extractions appear in Table 6 (for P427, constitutive promoter) and Table 7 (CBF2P, cold-inducible promoter).

TABLE 6

Plant extracts, determined gravimetrically by ASE, for vector control (PND9) and genetically-modified (constitutive P427 promoter driving HMGR + FPP) guayule plants subjected to cold treatment (25 C. day/10 C. night) for 77 days in vitro, following establishment from shoot tips.

| Construct, transformation date event | Solvent | % Dry Weight extract (avg) | % Dry Weight extract (stdev) |
|---|---|---|---|
| PND9, 5/13 E (control) | Acetone (resins, including sterols) | 8.01 | 0.39 |
| P427, 1/16 A | | 6.91 | 0.03 |
| P427, 4/4 C | | 5.59 | 1.59 |

TABLE 6-continued

Plant extracts, determined gravimetrically by ASE, for vector control (PND9) and genetically-modified (constitutive P427 promoter driving HMGR + FPP) guayule plants subjected to cold treatment (25 C. day/10 C. night) for 77 days in vitro, following establishment from shoot tips.

| Construct, transformation date event | Solvent | % Dry Weight extract (avg) | % Dry Weight extract (stdev) |
|---|---|---|---|
| P427, 2/1 E | | 6.53 | 1.37 |
| P427, 4/21 G | | 6.44 | 1.20 |
| P427, 4/30 H | | 7.49 | 0.26 |
| P427, 4/30 I | | 6.50 | 0.13 |
| PND9, 5/13 E (control) | Methanol (pigments, carbohydrates, sugars) | 27.06 | 1.45 |
| P427, 1/16 A | | 23.58 | 1.90 |
| P427, 4/4 C | | 26.10 | 2.36 |
| P427, 2/1 E | | 25.84 | 3.75 |
| P427, 4/21 G | | 24.31 | 0.52 |
| P427, 4/30 H | | 25.05 | 0.97 |
| P427, 4/30 I | | 28.63 | 0.68 |
| PND9, 5/13 E (control) | Cyclohexane (rubber) | 2.15 | 0.15 |
| P427, 1/16 A | | 2.51 | 0.10 |
| P427, 4/4 C | | 1.79 | 0.16 |
| P427, 2/1 E | | 2.19 | 0.10 |
| P427, 4/21 G | | 2.48 | 0.51 |
| P427, 4/30 H | | 2.11 | 0.26 |
| P427, 4/30 I | | 1.47 | 0.20 |

No significant differences were found for resin, rubber, or methanol extracts between the control and 6 lines of genetically-modified (P427 driving HMGR+FPP) plants. This is in contrast to our earlier report of enhanced rubber content in laboratory evaluations of one line of HMGR-overexpressing guayule (Dong et al., 2013, Industrial Crops and Products 46:15-24. 2013) and is probably due to the growth chamber cold treatment. In the Dong et al. 2013 study, HMGR-modified plants did not show enhanced rubber content when field-tested, a result attributed to the temperature extremes during the Arizona field trial. Surprisingly, when HMGR+FPP were driven by the cold-inducible promoter CBF2P, natural rubber production was higher for cold-treated plants (Table 7). In the case of the CBF2P driving HMGR+FPP plants, no significant differences were found for the resin content (terpene resins and sterols) or the methanol extracts, but significantly higher rubber content (+/−2SD, 95% confidence) was detected for 8 of 8 independently transformed lines. Rubber content was increased by (2.7 to 6.5 fold).

TABLE 7

Plant extracts, determined gravimetrically by ASE, for vector control (PND9) and genetically-modified (cold-inducible promoter CBF2P driving HMGR + FPP) guayule plants subjected to cold treatment (25 C. day/10 C. night) for 78 days in vitro, following establishment from shoot tips

| Construct, transformation date event | Solvent | % Dry Weight extract (avg) | % Dry Weight extract (stdev) |
|---|---|---|---|
| PND9, 5/13 E (control) | Acetone (resins, including sterols) | 6.75 | 0.16 |
| CBF2P, 11/3 B | | 6.14 | 0.28 |
| CBF2P, 11/3 C | | 6.27 | 0.04 |
| CBF2P, 6/15 D | | 6.33 | 0.09 |
| CBF2P, 11/3 E | | 7.00 | 0.27 |
| CBF2P, 12/22 I | | 7.02 | 0.04 |
| CBF2P, 11/10 G | | 6.39 | 0.05 |
| CBF2P, 11/22 J | | 6.70 | 0.08 |
| CBF2P, 11/3 K | | 6.74 | 0.13 |
| PND9, 5/13 E (control) | Methanol (pigments, carbohydrates, sugars) | 26.39 | 1.20 |
| CBF2P, 11/3 B | | 26.65 | 1.58 |
| CBF2P, 11/3 C | | 26.91 | 1.16 |
| CBF2P, 6/15 D | | 28.35 | 1.84 |
| CBF2P, 11/3 E | | 28.40 | 1.39 |
| CBF2P, 12/22 I | | 27.25 | 1.01 |
| CBF2P, 11/10 G | | 28.33 | 0.74 |
| CBF2P, 11/22 J | | 28.31 | 0.28 |
| CBF2P, 11/3 K | | 28.09 | 1.85 |
| PND9, 5/13 E (control) | Cyclohexane (rubber) | 0.46 | 0.11 |
| CBF2P, 11/3 B | | 1.33 | 0.16 |
| CBF2P, 11/3 C | | 1.29 | 0.10 |
| CBF2P, 6/15 D | | 1.25 | 0.14 |
| CBF2P, 11/3 E | | 2.65 | 0.07 |
| CBF2P, 12/22 I | | 1.73 | 0.05 |
| CBF2P, 11/10 G | | 2.34 | 0.59 |
| CBF2P, 11/22 J | | 2.49 | 0.06 |
| CBF2P, 11/3 K | | 2.97 | 0.27 |

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A transgenic guayule plant which produces increased amounts of rubber compared to the amount of rubber produced by a wild-type guayule plant, said transgenic guayule plant comprises an expression vector comprising a constitutive promoter operably linked to a heterologous polynucleotide encoding a polypeptide having the amino acid sequence of SEQ ID NO: 2; wherein said transgenic guayule plant produces the polypeptide having the amino acid sequence of SEQ ID NO: 2; and wherein said transgenic guayule plant produces increased amounts of rubber compared to the amount of rubber produced by a wild-type guayule plant.

2. The transgenic guayule plant of claim 1, wherein said heterologous polynucleotide comprises SEQ ID NO: 1.

3. The transgenic guayule plant of claim 1, wherein the heterologous polynucleotide comprises nucleotides 2863 through 4215 of SEQ ID NO: 1.

4. The transgenic guayule plant of claim 1, wherein said transgenic guayule plant has a dwarf phenotype under field grown conditions compared to the size of wild-type guayule plants under field grown conditions.

5. The transgenic guayule plant of claim 1, wherein said transgenic guayule plant has increased survival rate after harvesting compared to the survival rate after harvesting of a wild-type guayule plant.

6. A method for generating a transgenic guayule plant that produces more rubber compared to the amount of rubber produced by a wild-type guayule plant, said method comprising:
   (a) transforming a wild-type guayule plant cell with an expression vector comprising a constitutive promoter operably linked to a heterologous polynucleotide, wherein the heterologous polynucleotide encodes a polypeptide having the amino acid sequence of SEQ ID NO: 2 to provide a transformed guayule plant cell;
   (b) selecting a transformed guayule plant cell that produces said polypeptide having the amino acid sequence of SEQ ID NO: 2 to provide a selected transformed guayule plant cell; and
   (c) regenerating said selected transformed guayule plant cell to provide said transgenic guayule plant; wherein said transgenic guayule plant produces said polypeptide having the amino acid sequence of SEQ ID NO: 2 and produces more rubber compared to the amount of rubber produced by a wild-type guayule plant.

7. A transgenic guayule plant produced according to the method of claim 6.

8. The transgenic guayule plant of claim 7, wherein said transgenic guayule plant has a dwarf phenotype under field grown conditions compared to the size of wild-type guayule plants under field grown conditions.

9. The transgenic guayule plant of claim 7, wherein said transgenic guayule plant has increased regrowth in the field compared to the amount of regrowth of a non-transgenic guayule plant in the field.

10. A cell of said transgenic guayule plant of claim 7.

11. A transgenic guayule plant which produces increased amounts of rubber compared to the amount of rubber produced by a wild-type guayule plant, the transgenic guayule plant comprises an expression vector comprising a cold-inducible promoter operably linked to a heterologous polynucleotide; wherein said heterologous polynucleotide encodes a polypeptide having the amino acid sequence of SEQ ID NO: 2 and encodes Bacillus strearothermophilus farnesyl pyrophosphate synthase (FPPS) having a DNA sequence of nucleotides 7833 through 8753 of SEQ ID NO: 12 or nucleotides 6063 through 6983 of SEQ ID NO: 13; wherein said transgenic guayule plant produces said polypeptide having the amino acid sequence of SEQ ID NO: 2 and said FPPS when exposed to cold temperature; and wherein said transgenic guayule plant produces increased amounts of rubber compared to the amount of rubber produced by a wild-type guayule plant.

12. The transgenic guayule plant of claim 11, wherein said cold inducible promoter is a member selected from the group consisting of cor15a; Cor39; WRKY71; wcs120; RCI2A; RCI2B and CBF2.

13. The transgenic guayule plant of claim 11, wherein said transgenic guayule plant does not exhibit an increase in resin content compared to the amount of resin content in a wild-type guayule plant.

14. The transgenic guayule plant of claim 11, wherein the amount of rubber produced by said transgenic guayule plant when said cold-inducible promoter is active increases about 2.5 fold or more compared to the amount of rubber produced by a non-transgenic guayule plant.

15. The transgenic guayule plant of claim 11, wherein said heterologous polynucleotide encoding said polypeptide having the amino acid sequence of SEQ ID NO: 2 comprises SEQ ID NO: 1.

16. The transgenic guayule plant of claim 11, wherein said heterologous polynucleotide encoding said polypeptide having the amino acid sequence of SEQ ID NO: 2 comprises nucleotides 2863 through 4215 of SEQ ID NO: 1.

17. The transgenic guayule plant of claim 11, wherein said heterologous polynucleotide further comprises a linker sequence between the DNA encoding said polypeptide having the amino acid sequence of SEQ ID NO: 2 and the DNA encoding said FPPS.

18. The transgenic guayule plant of claim 17, wherein said linker sequence is selected from the group consisting of nucleotides 7761 through 7832 of SEQ ID NO: 12 and nucleotides 5991 through 6062 of SEQ ID NO: 13.

19. The transgenic guayule plant of claim 11, wherein DNA encoding said polypeptide having the amino acid sequence of SEQ ID NO: 2 is upstream of DNA encoding said FPPS.

20. The transgenic guayule plant of claim 11, wherein DNA encoding said FPPS is upstream of DNA encoding said polypeptide having the amino acid sequence of SEQ ID NO: 2.

21. The transgenic guayule plant of claim 11, wherein said transgenic guayule plant has increased regrowth in the field compared to the amount of regrowth of a non-transgenic guayule plant in the field.

22. The transgenic guayule plant of claim 11, wherein said transgenic guayule plant has a dwarf phenotype under field grown conditions compared to the size of wild-type guayule plants under field grown conditions.

23. A method for generating a transgenic guayule plant that produces more rubber compared to the amount of rubber produced by a wild-type guayule plant, the method comprising:

(a) transforming a wild-type guayule plant cell with an expression vector comprising a cold-inducible promoter operably linked to a heterologous polynucleotide, wherein the heterologous polynucleotide encodes a polypeptide having the amino acid sequence of SEQ ID NO: 2 and encodes *Bacillus strearothermophilus* farnesyl pyrophosphate synthase (FPPS) having a DNA sequence of nucleotides 7833 through 8753 of SEQ ID NO: 12 or nucleotides 6063 through 6983 of SEQ ID NO: 13 to provide a transformed guayule plant cell;

(b) selecting a transformed guayule plant cell that produces said polypeptide having the amino acid sequence of SEQ ID NO: 2 and said FPPS when said transformed guayule plant cell is exposed to cold treatment to provide a selected transformed guayule plant cell; and (c) regenerating said selected transformed guayule plant cell to provide said transgenic guayule plant that produces said polypeptide having the amino acid sequence of SEQ ID NO: 2 and said FPPS in response to cold treatment; wherein, when said transgenic guayule plant is exposed to said cold treatment, said transgenic guayule plant produces said polypeptide having said amino acid sequence of SEQ ID NO: 2 and said FPPS, and produces more rubber compared to the amount of rubber produced by a wild-type guayule plant.

24. A transgenic guayule plant produced according to the method of claim 23.

25. The transgenic guayule plant of claim 24, wherein said transgenic guayule plant has a dwarf phenotype under field grown conditions compared to the size of wild-type guayule plants under field grown conditions.

26. The transgenic guayule plant of claim 24, wherein said transgenic guayule plant has increased regrowth in the field compared to the amount of regrowth of a non-transgenic guayule plant in the field.

27. A cell of said transgenic guayule plant of claim 24.

\* \* \* \* \*